United States Patent
Seo et al.

(10) Patent No.: US 11,917,882 B2
(45) Date of Patent: *Feb. 27, 2024

(54) LIGHT-EMITTING DEVICE, ELECTRONIC DEVICE, AND LIGHTING DEVICE

(71) Applicant: Semiconductor Energy Laboratory Co., Ltd., Kanagawa-ken (JP)

(72) Inventors: Satoshi Seo, Kanagawa (JP); Toshiki Sasaki, Kanagawa (JP); Tsunenori Suzuki, Kanagawa (JP); Sachiko Kawakami, Kanagawa (JP); Naoaki Hashimoto, Kanagawa (JP)

(73) Assignee: Semiconductor Energy Laboratory Co., Ltd. (JP)

(*) Notice: Subject to any disclaimer, the term of this patent is extended or adjusted under 35 U.S.C. 154(b) by 63 days.

This patent is subject to a terminal disclaimer.

(21) Appl. No.: 17/104,398

(22) Filed: Nov. 25, 2020

(65) Prior Publication Data

US 2021/0104580 A1  Apr. 8, 2021

Related U.S. Application Data

(63) Continuation of application No. 15/866,879, filed on Jan. 10, 2018, now Pat. No. 10,854,682, which is a
(Continued)

(30) Foreign Application Priority Data

Aug. 8, 2014  (JP) .................................. 2014-162532
Aug. 8, 2014  (JP) .................................. 2014-162576
(Continued)

(51) Int. Cl.
C07D 307/77 (2006.01)
C09K 11/06 (2006.01)
(Continued)

(52) U.S. Cl.
CPC ......... H10K 59/351 (2023.02); C07D 307/77 (2013.01); C09K 11/06 (2013.01);
(Continued)

(58) Field of Classification Search
CPC ............. H01L 27/3213; H01L 27/3209; H01L 51/0054; H01L 51/006; H01L 51/0061;
(Continued)

(56) References Cited

U.S. PATENT DOCUMENTS 7,232,619 B2  6/2007  Nomura et al.
7,541,098 B2  6/2009  Nomura et al.
(Continued)

FOREIGN PATENT DOCUMENTS

CN  102040528 A  5/2011
CN  102219774 A  10/2011
(Continued)

OTHER PUBLICATIONS

Wee et al., (2009), The Journal of Organic Chemistry, 74(21), 8472-8475. (Year: 2009).*
(Continued)

Primary Examiner — Dawn L Garrett
(74) Attorney, Agent, or Firm — Husch Blackwell LLP

(57) ABSTRACT

A light-emitting device, an electronic device, or a lighting device with low power consumption and high reliability is provided. The light-emitting device includes a first light-emitting element, a second light-emitting element, a third light-emitting element, and a fourth light-emitting element. The first to fourth light-emitting elements include the same EL layer between an anode and a cathode. The EL layer includes a first light-emitting layer and a second light-emitting layer. The first light-emitting layer contains a fluorescent substance. The peak wavelength of an emission spectrum of the fluorescent substance in a toluene solution
(Continued)

of the fluorescent substance is 440 nm to 460 nm, preferably 440 nm to 455 nm. The second light-emitting layer contains a phosphorescent substance. The first light-emitting element exhibits blue emission. The second light-emitting element exhibits green emission. The third light-emitting element exhibits red emission. The fourth light-emitting element exhibits yellow emission.

19 Claims, 33 Drawing Sheets

Related U.S. Application Data continuation of application No. 14/818,951, filed on Aug. 5, 2015, now Pat. No. 9,876,056.

(30) Foreign Application Priority Data

Nov. 28, 2014 (JP) ................................ 2014-241188
Jun. 30, 2015 (JP) ................................ 2015-131156

(51) Int. Cl.
| | | |
|---|---|---|
| *H01L 51/50* | (2006.01) | |
| *H10K 59/35* | (2023.01) | |
| *H10K 50/11* | (2023.01) | |
| *H10K 50/19* | (2023.01) | |
| *H10K 59/32* | (2023.01) | |
| *H10K 85/60* | (2023.01) | |
| *H10K 50/13* | (2023.01) | |
| *H10K 59/40* | (2023.01) | |
| *H10K 101/10* | (2023.01) | |
| *H10K 101/00* | (2023.01) | |

(52) U.S. Cl.
CPC ............ *H10K 50/11* (2023.02); *H10K 50/19* (2023.02); *H10K 59/32* (2023.02); *H10K 85/622* (2023.02); *H10K 85/633* (2023.02); *H10K 85/636* (2023.02); *H10K 85/6574* (2023.02); *C09K 2211/1007* (2013.01); *C09K 2211/1011* (2013.01); *C09K 2211/1014* (2013.01); *C09K 2211/1088* (2013.01); *H10K 50/131* (2023.02); *H10K 59/40* (2023.02); *H10K 85/626* (2023.02); *H10K 2101/10* (2023.02); *H10K 2101/27* (2023.02)

(58) Field of Classification Search
CPC ............ H01L 51/0073; H01L 51/5016; H01L 51/5278; H01L 27/323; H01L 51/0058; H01L 51/5012; H01L 51/5044; H01L 2251/5376; C07D 307/77; C09K 11/06; C09K 2211/1007; C09K 2211/1011; C09K 2211/1014; C09K 2211/1088
See application file for complete search history.

(56) References Cited

U.S. PATENT DOCUMENTS

| | | | |
|---|---|---|---|
| 7,838,128 B2 | 11/2010 | Kawakami et al. | |
| 7,906,226 B2 | 3/2011 | Matsuura et al. | |
| 8,040,047 B2 | 10/2011 | Ushikubo et al. | |
| 8,251,765 B2 | 8/2012 | Ushikubo et al. | |
| 8,575,631 B2 | 11/2013 | Yamazaki | |
| 8,604,224 B2 | 12/2013 | Suzuki et al. | |
| 8,629,430 B2 | 1/2014 | Kawamura et al. | |
| 8,642,190 B2 | 2/2014 | Ogita et al. | |
| 8,789,968 B2 | 7/2014 | Ohsawa et al. | |
| 8,866,135 B2 | 10/2014 | Kawamura et al. | |
| 8,866,163 B2 | 10/2014 | Toda et al. | |
| 8,883,323 B2 | 11/2014 | Kawamura et al. | |
| 8,941,102 B2 | 1/2015 | Tsuji et al. | |
| 9,000,458 B2 | 4/2015 | Seo et al. | |
| 9,065,066 B2 | 6/2015 | Seo et al. | |
| 9,093,649 B2 | 7/2015 | Kawakami et al. | |
| 9,147,847 B2 | 9/2015 | Kawamura et al. | |
| 9,172,059 B2 | 10/2015 | Seo et al. | |
| 9,287,332 B2 | 3/2016 | Hatano | |
| 9,324,950 B2 | 4/2016 | Kawamura et al. | |
| 9,373,792 B2 | 6/2016 | Kawamura et al. | |
| 9,450,209 B2 | 9/2016 | Seo et al. | |
| 9,691,825 B2 | 6/2017 | Seo et al. | |
| 9,741,967 B2 | 8/2017 | Ohsawa et al. | |
| 9,761,812 B2 | 9/2017 | Osaka et al. | |
| 9,847,379 B2 | 12/2017 | Hatano | |
| 9,876,056 B2 | 1/2018 | Seo et al. | |
| 10,084,156 B2 | 9/2018 | Seo et al. | |
| 10,333,106 B2 | 6/2019 | Ohsawa et al. | |
| 10,570,113 B2 | 2/2020 | Ogita et al. | |
| 10,629,823 B2 | 4/2020 | Osaka et al. | |
| 10,854,682 B2 * | 12/2020 | Seo .................... H01L 51/006 | |
| 11,046,667 B2 | 6/2021 | Ogita et al. | |
| 2004/0124766 A1 | 7/2004 | Nakagawa et al. | |
| 2006/0082295 A1 | 4/2006 | Chin et al. | |
| 2009/0066238 A1 | 3/2009 | Chen et al. | |
| 2009/0247795 A1 | 10/2009 | Kawakami | |
| 2011/0095678 A1 | 4/2011 | Ogita et al. | |
| 2011/0214714 A1 | 9/2011 | Aberle et al. | |
| 2011/0215714 A1 | 9/2011 | Seo et al. | |
| 2011/0248246 A1 | 10/2011 | Ogita et al. | |
| 2012/0098012 A1 | 4/2012 | Kim et al. | |
| 2012/0098417 A1 | 4/2012 | Inoue et al. | |
| 2012/0126205 A1 | 5/2012 | Kawamura et al. | |
| 2012/0206675 A1 | 8/2012 | Seo et al. | |
| 2012/0243219 A1 | 9/2012 | Ohsawa et al. | |
| 2012/0267652 A1 | 10/2012 | Toda et al. | |
| 2012/0273822 A1 | 11/2012 | Ohsawa et al. | |
| 2013/0087773 A1 | 4/2013 | Suzuki et al. | |
| 2013/0240851 A1 | 9/2013 | Seo et al. | |
| 2013/0292656 A1 | 11/2013 | Seo et al. | |
| 2014/0042469 A1 | 2/2014 | Seo et al. | |
| 2014/0061604 A1 | 3/2014 | Seo et al. | |
| 2014/0070198 A1 | 3/2014 | Nowatari et al. | |
| 2014/0131697 A1 | 5/2014 | Ogita et al. | |
| 2014/0145168 A1 | 5/2014 | Ohsawa et al. | |
| 2014/0175470 A1 | 6/2014 | Yokoyama et al. | |
| 2014/0225140 A1 | 8/2014 | Nishido et al. | |
| 2014/0353619 A1 * | 12/2014 | Park .................. H01L 27/3265 438/34 | |
| 2015/0031900 A1 | 1/2015 | Kawakami et al. | |
| 2015/0041792 A1 | 2/2015 | Suzuki et al. | |
| 2015/0102331 A1 | 4/2015 | Seo et al. | |
| 2015/0108462 A1 | 4/2015 | Inoue et al. | |
| 2015/0329514 A1 | 11/2015 | Kawakami et al. | |
| 2016/0254459 A1 | 9/2016 | Kawamura et al. | |
| 2018/0026233 A1 | 1/2018 | Ohsawa et al. | |
| 2018/0108713 A1 | 4/2018 | Hatano | |
| 2022/0106286 A1 | 4/2022 | Ogita et al. | |

FOREIGN PATENT DOCUMENTS

| | | |
|---|---|---|
| CN | 102448945 A | 5/2012 |
| CN | 102456840 A | 5/2012 |
| CN | 102751441 A | 10/2012 |
| CN | 103102277 A | 5/2013 |
| CN | 103168043 A | 6/2013 |
| CN | 103254241 A | 8/2013 |
| CN | 103636289 A | 3/2014 |
| CN | 104471733 A | 3/2015 |
| DE | 11 2011 103 544 B4 | 8/2013 |
| DE | 11 2013 001 439 T5 | 1/2015 |
| EP | 2 051 310 A1 | 4/2009 |
| EP | 2 110 369 A1 | 10/2009 |
| EP | 2 314 565 A1 | 4/2011 |
| EP | 2 366 753 A1 | 9/2011 |
| EP | 2 436 679 A1 | 4/2012 |
| EP | 2 515 616 A1 | 10/2012 |
| JP | 2007-045816 A | 2/2007 |
| JP | 2009-256340 A | 11/2009 |
| JP | 2009-290051 A | 12/2009 |

(56) References Cited

FOREIGN PATENT DOCUMENTS

| | | |
|---|---|---|
| JP | 2010-182699 A | 8/2010 |
| JP | 2011-204673 A | 10/2011 |
| JP | 2012-046478 A | 3/2012 |
| JP | 2012-149030 A | 8/2012 |
| JP | 2012-182127 A | 9/2012 |
| JP | 2012-216519 A | 11/2012 |
| JP | 2012-227133 A | 11/2012 |
| JP | 2013-053158 A | 3/2013 |
| JP | 2013-100293 A | 5/2013 |
| JP | 2013-151537 A | 8/2013 |
| JP | 2013-214523 A | 10/2013 |
| JP | 2013-219024 A | 10/2013 |
| JP | 2013-543250 | 11/2013 |
| JP | 2014-123721 A | 7/2014 |
| JP | 2015-042636 A | 3/2015 |
| JP | 5738459 B2 | 6/2015 |
| JP | 2015-120725 A | 7/2015 |
| JP | 2015-144283 A | 8/2015 |
| JP | 2015-144303 A | 8/2015 |
| KR | 2011-0044159 A | 4/2011 |
| KR | 2011-0099645 A | 9/2011 |
| KR | 2011-0113593 A | 10/2011 |
| KR | 2012-0092510 A | 8/2012 |
| KR | 2012-0109397 A | 10/2012 |
| KR | 2014-0001850 A | 1/2014 |
| KR | 2014-0012769 A | 2/2014 |
| KR | 2014-0136027 A | 11/2014 |
| TW | 201233767 | 8/2012 |
| TW | 201301607 | 1/2013 |
| TW | 201315797 | 4/2013 |
| TW | 201336969 | 9/2013 |
| TW | 201349614 | 12/2013 |
| TW | 201509937 | 3/2015 |
| WO | WO 2007/007885 A1 | 1/2007 |
| WO | WO 2012/053627 A1 | 4/2012 |
| WO | WO 2012/070233 A1 | 5/2012 |
| WO | WO 2012/070234 A1 | 5/2012 |
| WO | WO 2012/086662 A1 | 6/2012 |
| WO | WO 2012/090970 A1 | 7/2012 |
| WO | WO 2013/137088 A1 | 9/2013 |
| WO | WO 2015/011614 A1 | 1/2015 |

OTHER PUBLICATIONS

Chinese Office Action (Application No. 201910024880.9) dated Mar. 23, 2021.
German Office Action (Application No. 112015003690.3) dated Jun. 29, 2021.
International Search Report re Application No. PCT/IB2015/055749, dated Nov. 2, 2015.
Written Opinion re Application No. PCT/IB2015/055749, dated Nov. 2, 2015.
Chinese Office Action re Application No. CN 201580042349.4, dated Apr. 11, 2018.
Taiwanese Office Action re Application No. TW 108142210, dated Dec. 17, 2019.
"The Electromagnetic Spectrum," https://www.uib.no/en/hms-portalen/75292/electromagnetic-spectrum, Dec. 2, 2013.
Chinese Office Action re Application No. CN 201910024880.9, dated Jul. 29, 2020.

* cited by examiner

LIGHT-EMITTING DEVICE, ELECTRONIC DEVICE, AND LIGHTING DEVICE

This application is a continuation of copending U.S. application Ser. No. 15/866,879, filed on Jan. 10, 2018 which is a continuation of U.S. application Ser. No. 14/818,951, filed on Aug. 5, 2015 (now U.S. Pat. No. 9,876,056 issued Jan. 23, 2018) which are all incorporated herein by reference.

TECHNICAL FIELD

The present invention relates to an object, a method, or a manufacturing method. In addition, the present invention relates to a process, a machine, manufacture, or a composition of matter. In particular, one embodiment of the present invention relates to a light-emitting element, a light-emitting device, an electronic device, a lighting device, a driving method thereof, or a manufacturing method thereof.

BACKGROUND ART

A light-emitting element using an organic compound as a luminous body, which has features such as thinness, lightness, high-speed response, and DC drive at low voltage, is expected to be applied to a next-generation flat panel display. In particular, a light-emitting device in which light-emitting elements are arranged in matrix is considered to have advantages in a wide viewing angle and excellent visibility over a conventional liquid crystal display device.

The light emission mechanism of a light-emitting element is said to be as follows: when a voltage is applied between a pair of electrodes with an EL layer including a luminous body provided therebetween, electrons injected from the cathode and holes injected from the anode recombine in the light emission center of the EL layer to form molecular excitons, and energy is released and light is emitted when the molecular excitons return to the ground state. Singlet excitation and triplet excitation are known as excited states, and it is thought that light emission can be achieved through either of the excited states.

In order to improve the characteristics of a light-emitting device including such light-emitting elements, improvement of an element structure, development of materials, and the like have been actively carried out (for example, see Patent Document 1).

REFERENCE

Patent Document

[Patent Document 1] Japanese Published Patent Application No. 2010-182699

DISCLOSURE OF INVENTION

In development of a light-emitting element, a reduction in driving voltage or a reduction in current amount is one of key factors in achieving lower consumption of products. In addition to element structures in which a carrier balance in an EL layer of a light-emitting element can be controlled or the recombination probability of carriers can be improved, the emission characteristics of a light-emitting layer in the EL layer are important factors for a reduction in the driving voltage or a reduction in the current amount of the light-emitting element. Therefore, it is important to reduce the driving voltage or current amount of the light-emitting element with the improved emission characteristics of the light-emitting layer by using the EL layer having a desired structure. The light-emitting element preferably has high reliability in addition to lower driving voltage.

In view of this, one embodiment of the present invention provides a light-emitting device, an electronic device, or a lighting device with low power consumption. Another embodiment of the present invention provides a light-emitting device, an electronic device, or a lighting device with low power consumption and high reliability. Another embodiment of the present invention provides a novel light-emitting element and a novel light-emitting device. Note that the descriptions of these objects do not disturb the existence of other objects. In one embodiment of the present invention, there is no need to achieve all the objects. Other objects will be apparent from and can be derived from the description of the specification, the drawings, the claims, and the like.

One embodiment of the present invention is a light-emitting device including a first light-emitting element, a second light-emitting element, a third light-emitting element, and a fourth light-emitting element. The first light-emitting element includes a first EL layer, a second EL layer, and a charge-generation layer. The second light-emitting element includes the first EL layer, the second EL layer, and the charge-generation layer. The third light-emitting element includes the first EL layer, the second EL layer, and the charge-generation layer. The fourth light-emitting element includes the first EL layer, the second EL layer, and the charge-generation layer. The first EL layer includes a region functioning as part of the first light-emitting element, a region functioning as part of the second light-emitting element, a region functioning as part of the third light-emitting element, and a region functioning as part of the fourth light-emitting element. The second EL layer includes a region functioning as part of the first light-emitting element, a region functioning as part of the second light-emitting element, a region functioning as part of the third light-emitting element, and a region functioning as part of the fourth light-emitting element. The charge-generation layer includes a region functioning as part of the first light-emitting element, a region functioning as part of the second light-emitting element, a region functioning as part of the third light-emitting element, and a region functioning as part of the fourth light-emitting element. The charge-generation layer is between the first EL layer and the second EL layer. The first EL layer contains an organic compound in which each of two benzo[b]naphtho[1,2-d]furanylamine skeletons is independently bonded to a pyrene skeleton. The second EL layer has a function of emitting phosphorescence. The first light-emitting element has a function of emitting blue light. The second light-emitting element has a function of emitting green light. The third light-emitting element has a function of emitting red light.

Another embodiment of the present invention is a light-emitting device including a first light-emitting element, a second light-emitting element, a third light-emitting element, and a fourth light-emitting element. The first light-emitting element includes a first EL layer, a second EL layer, and a charge-generation layer. The second light-emitting element includes the first EL layer, the second EL layer, and the charge-generation layer. The third light-emitting element includes the first EL layer, the second EL layer, and the charge-generation layer. The fourth light-emitting element includes the first EL layer, the second EL layer, and the charge-generation layer. The first light-emitting element includes an anode. The first EL layer is between the anode and the charge-generation layer. The first EL layer includes a region functioning as part of the first light-emitting element, a region functioning as part of the second light-emitting element, a region functioning as part of the third light-emitting element, and a region functioning as part of the fourth light-emitting element. The second EL layer includes a region functioning as part of the first light-emitting element, a region functioning as part of the second light-emitting element, a region functioning as part of the third light-emitting element, and a region functioning as part of the fourth light-emitting element. The charge-generation layer includes a region functioning as part of the first light-emitting element, a region functioning as part of the second light-emitting element, a region functioning as part of the third light-emitting element, and a region functioning as part of the fourth light-emitting element. The charge-generation layer is between the first EL layer and the second EL layer. The first EL layer contains an organic compound in which each of two benzo[b]naphtho[1,2-d]furanylamine skeletons is independently bonded to a pyrene skeleton. The second EL layer has a function of emitting phosphorescence. The first light-emitting element has a function of emitting blue light. The second light-emitting element has a function of emitting green light. The third light-emitting element has a function of emitting red light.

Another embodiment of the present invention is a light-emitting device including a first light-emitting element, a second light-emitting element, a third light-emitting element, and a fourth light-emitting element. The first light-emitting element includes a first EL layer, a second EL layer, and a charge-generation layer. The second light-emitting element includes the first EL layer, the second EL layer, and the charge-generation layer. The third light-emitting element includes the first EL layer, the second EL layer, and the charge-generation layer. The fourth light-emitting element includes the first EL layer, the second EL layer, and the charge-generation layer. The first light-emitting element includes an anode. The first EL layer is between the anode and the charge-generation layer. The first EL layer includes a region functioning as part of the first light-emitting element, a region functioning as part of the second light-emitting element, a region functioning as part of the third light-emitting element, and a region functioning as part of the fourth light-emitting element. The second EL layer includes a region functioning as part of the first light-emitting element, a region functioning as part of the second light-emitting element, a region functioning as part of the third light-emitting element, and a region functioning as part of the fourth light-emitting element. The charge-generation layer includes a region functioning as part of the first light-emitting element, a region functioning as part of the second light-emitting element, a region functioning as part of the third light-emitting element, and a region functioning as part of the fourth light-emitting element. The charge-generation layer is between the first EL layer and the second EL layer. The first EL layer contains an organic compound in which each of two benzo[b]naphtho[1,2-d]furanylamine skeletons is independently bonded to a pyrene skeleton. The second EL layer has a function of emitting yellow phosphorescence. The first light-emitting element has a function of emitting blue light. The second light-emitting element has a function of emitting green light. The third light-emitting element has a function of emitting red light.

In the light-emitting device with any of the above structures, the two benzo[b]naphtho[1,2-d]furanylamine skeletons are respectively bonded to the 1-position and the 6-position of the pyrene skeleton.

In the light-emitting device with any of the above structures, each of nitrogen atoms in the two benzo[b]naphtho[1,2-d]furanylamine skeletons is independently bonded to the 6-position or the 8-position of a benzo[b]naphtho[1,2-d]furanyl group.

Another embodiment of the present invention is a light-emitting device including a first light-emitting element, a second light-emitting element, a third light-emitting element, and a fourth light-emitting element. The first light-emitting element includes a first EL layer, a second EL layer, and a charge-generation layer. The second light-emitting element includes the first EL layer, the second EL layer, and the charge-generation layer. The third light-emitting element includes the first EL layer, the second EL layer, and the charge-generation layer. The fourth light-emitting element includes the first EL layer, the second EL layer, and the charge-generation layer. The first light-emitting element includes an anode. The first EL layer is between the anode and the charge-generation layer. The first EL layer includes a region functioning as part of the first light-emitting element, a region functioning as part of the second light-emitting element, a region functioning as part of the third light-emitting element, and a region functioning as part of the fourth light-emitting element. The second EL layer includes a region functioning as part of the first light-emitting element, a region functioning as part of the second light-emitting element, a region functioning as part of the third light-emitting element, and a region functioning as part of the fourth light-emitting element. The charge-generation layer includes a region functioning as part of the first light-emitting element, a region functioning as part of the second light-emitting element, a region functioning as part of the third light-emitting element, and a region functioning as part of the fourth light-emitting element. The charge-generation layer is between the first EL layer and the second EL layer. The first EL layer contains a first organic compound represented by General Formula (G1) and a second organic compound. The second EL layer has a function of emitting yellow phosphorescence. The first light-emitting element has a function of emitting blue light. The second light-emitting element has a function of emitting green light. The third light-emitting element has a function of emitting red light.

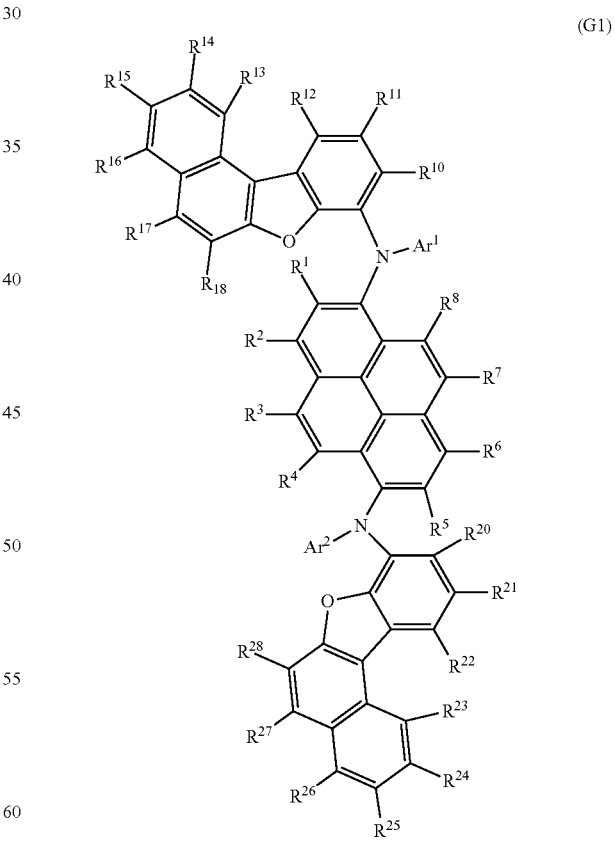

(G1)

In General Formula (G1), each of $Ar^1$ and $Ar^2$ independently represents a substituted or unsubstituted aryl group having 6 to 13 carbon atoms forming a ring, and each of $R^1$ to $R^8$, $R^{10}$ to $R^{18}$, and $R^{20}$ to $R^{28}$ independently represents hydrogen, a substituted or unsubstituted alkyl group having 1 to 6 carbon atoms, a substituted or unsubstituted alkoxy group having 1 to 6 carbon atoms, a cyano group, halogen, a substituted or unsubstituted haloalkyl group having 1 to 6 carbon atoms, or a substituted or unsubstituted aryl group having 6 to 10 carbon atoms.

Another embodiment of the present invention is a light-emitting device including a first light-emitting element, a second light-emitting element, a third light-emitting element, and a fourth light-emitting element. The first light-emitting element includes a first EL layer, a second EL layer, and a charge-generation layer. The second light-emitting element includes the first EL layer, the second EL layer, and the charge-generation layer. The third light-emitting element includes the first EL layer, the second EL layer, and the charge-generation layer. The fourth light-emitting element includes the first EL layer, the second EL layer, and the charge-generation layer. The first light-emitting element includes an anode. The first EL layer is between the anode and the charge-generation layer. The first EL layer includes a region functioning as part of the first light-emitting element, a region functioning as part of the second light-emitting element, a region functioning as part of the third light-emitting element, and a region functioning as part of the fourth light-emitting element. The second EL layer includes a region functioning as part of the first light-emitting element, a region functioning as part of the second light-emitting element, a region functioning as part of the third light-emitting element, and a region functioning as part of the fourth light-emitting element. The charge-generation layer includes a region functioning as part of the first light-emitting element, a region functioning as part of the second light-emitting element, a region functioning as part of the third light-emitting element, and a region functioning as part of the fourth light-emitting element. The charge-generation layer is between the first EL layer and the second EL layer. The first EL layer contains a first organic compound represented by General Formula (G2) and a second organic compound. The second EL layer has a function of emitting yellow phosphorescence. The first light-emitting element has a function of emitting blue light. The second light-emitting element has a function of emitting green light. The third light-emitting element has a function of emitting red light.

stituted alkyl group having 1 to 6 carbon atoms, a substituted or unsubstituted alkoxy group having 1 to 6 carbon atoms, a cyano group, halogen, a substituted or unsubstituted haloalkyl group having 1 to 6 carbon atoms, or a substituted or unsubstituted aryl group having 6 to 10 carbon atoms.

Another embodiment of the present invention is a light-emitting device including a first light-emitting element, a second light-emitting element, a third light-emitting element, and a fourth light-emitting element. The first light-emitting element includes a first EL layer, a second EL layer, and a charge-generation layer. The second light-emitting element includes the first EL layer, the second EL layer, and the charge-generation layer. The third light-emitting element includes the first EL layer, the second EL layer, and the charge-generation layer. The fourth light-emitting element includes the first EL layer, the second EL layer, and the charge-generation layer. The first light-emitting element includes an anode. The first EL layer is between the anode and the charge-generation layer. The first EL layer includes a region functioning as part of the first light-emitting element, a region functioning as part of the second light-emitting element, a region functioning as part of the third light-emitting element, and a region functioning as part of the fourth light-emitting element. The second EL layer includes a region functioning as part of the first light-emitting element, a region functioning as part of the second light-emitting element, a region functioning as part of the third light-emitting element, and a region functioning as part of the fourth light-emitting element. The charge-generation layer includes a region functioning as part of the first light-emitting element, a region functioning as part of the second light-emitting element, a region functioning as part of the third light-emitting element, and a region functioning as part of the fourth light-emitting element. The charge-generation layer is between the first EL layer and the second EL layer. The first EL layer contains a first organic compound represented by Structural Formula (132) and a second organic compound. The second EL layer has a function of emitting yellow phosphorescence. The first light-emitting element has a function of emitting blue light. The second light-emitting element has a function of emitting green light. The third light-emitting element has a function of emitting red light.

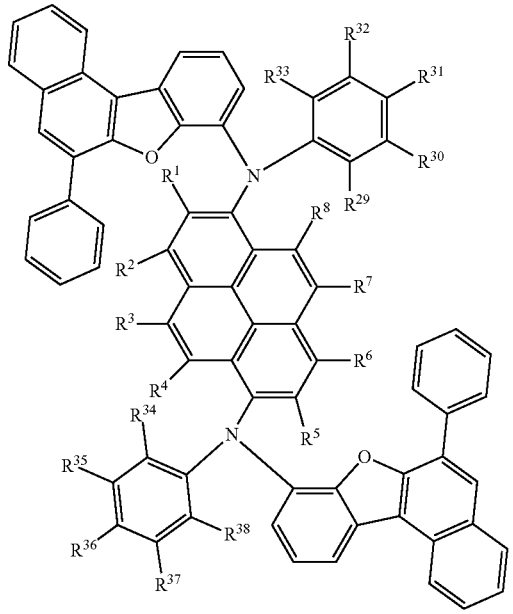

(G2)

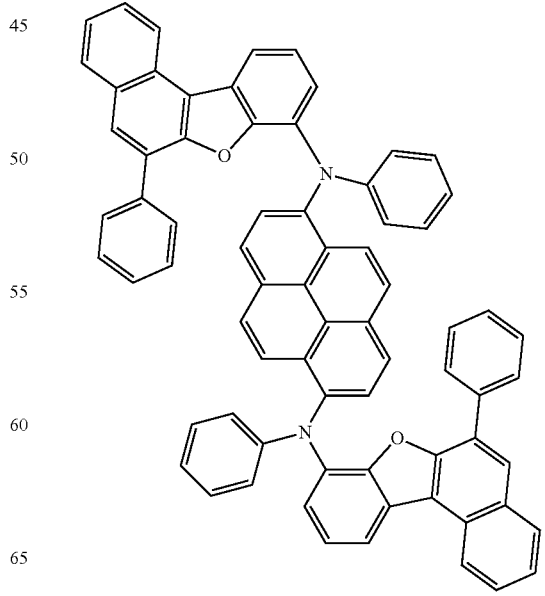

(132)

In General Formula (G2), each of $R^1$ to $R^8$ and $R^{29}$ to $R^{38}$ independently represents hydrogen, a substituted or unsub- Another embodiment of the present invention is a light-emitting device including a first light-emitting element, a second light-emitting element, a third light-emitting element, and a fourth light-emitting element. The first light-emitting element, the second light-emitting element, the third light-emitting element, and the fourth light-emitting element include the same EL layer between an anode and a cathode. The EL layer includes a first light-emitting layer and a second light-emitting layer. The first light-emitting layer contains a fluorescent substance. The peak wavelength of an emission spectrum of the fluorescent substance in a toluene solution of the fluorescent substance is 440 nm to 460 nm, preferably 440 nm to 455 nm. The second light-emitting layer contains a phosphorescent substance. The first light-emitting element exhibits blue emission. The second light-emitting element exhibits green emission. The third light-emitting element exhibits red emission. The fourth light-emitting element exhibits yellow emission.

Another embodiment of the present invention is a light-emitting device including a first light-emitting element, a second light-emitting element, a third light-emitting element, and a fourth light-emitting element. The first light-emitting element, the second light-emitting element, the third light-emitting element, and the fourth light-emitting element include, between an anode and a cathode, the same first EL layer and the same second EL layer between which the same charge-generation layer is. The first EL layer includes a first light-emitting layer. The second EL layer includes a second light-emitting layer. The first light-emitting layer contains a fluorescent substance. The peak wavelength of an emission spectrum of the fluorescent substance in a toluene solution of the fluorescent substance is 440 nm to 460 nm, preferably 440 nm to 455 nm. The second light-emitting layer contains a phosphorescent substance. The first light-emitting element exhibits blue emission. The second light-emitting element exhibits green emission. The third light-emitting element exhibits red emission. The fourth light-emitting element exhibits yellow emission.

Another embodiment of the present invention is the light-emitting device in which the half-width of the emission spectrum is greater than or equal to 20 nm and less than or equal to 50 nm.

Another embodiment of the present invention is the light-emitting device in which the first light-emitting element has an x-coordinate greater than or equal to 0.13 and less than or equal to 0.17 and a y-coordinate greater than or equal to 0.03 and less than or equal to 0.08 on the xy chromaticity diagram. Preferably, the first light-emitting element has a y-coordinate greater than or equal to 0.03 and less than or equal to 0.07 on the xy chromaticity diagram.

Another embodiment of the present invention is the light-emitting device in which light emission from the first light-emitting element is emitted to the outside of the light-emitting device through a blue color filter.

Another embodiment of the present invention is the light-emitting device in which the power consumption of the light-emitting device except the power consumption of a driving FET (the sum of power consumptions of the first to fourth light-emitting elements) is higher than or equal to 1 mW/cm$^2$ and lower than or equal to 7 mW/cm$^2$ when light having an x-coordinate of 0.313 and a y-coordinate of 0.329 on the xy chromaticity diagram is obtained with a luminance of 300 cd/m$^2$.

Another embodiment of the present invention is the light-emitting device in which the power consumption (power consumption calculated from the product of current consumption and a voltage between an anode and a cathode) of the light-emitting device including the power consumption of the driving FET is higher than or equal to 2 mW/cm$^2$ and lower than or equal to 15 mW/cm$^2$ in the case where light having an x-coordinate of 0.313 and a y-coordinate of 0.329 on the xy chromaticity diagram is obtained with a luminance of 300 cd/m$^2$.

Another embodiment of the present invention is an electronic device including the light-emitting device, and a connection terminal or an operation key.

One embodiment of the present invention includes, in its category, in addition to a light-emitting device including a light-emitting element, an electronic device including the light-emitting element or the light-emitting device (specifically, an electronic device including the light-emitting element or the light-emitting device and a connection terminal or an operation key) and a lighting device including the light-emitting element or the light-emitting device (specifically, a lighting device including the light-emitting element or the light-emitting device and a housing). The light-emitting device in this specification therefore refers to an image display device or a light source (e.g., a lighting device). In addition, the light-emitting device includes, in its category, a module in which a light-emitting device is connected to a connector such as a flexible printed circuit (FPC) or a tape carrier package (TCP), a module in which a printed wiring board is provided on the tip of a TCP, and a module in which an integrated circuit (IC) is directly mounted on a light-emitting element by a chip on glass (COG) method.

According to one embodiment of the present invention, a novel light-emitting device, a novel electronic device, and a novel lighting device can each be provided. Furthermore, a light-emitting device, an electronic device, and a lighting device with low power consumption can each be provided. Furthermore, a light-emitting device, an electronic device, and a lighting device with low power consumption and high reliability can each be provided. Note that the description of these effects does not disturb the existence of other effects. One embodiment of the present invention does not necessarily achieve all the effects listed above. Other effects will be apparent from and can be derived from the description of the specification, the drawings, the claims, and the like.

BEST MODE FOR CARRYING OUT THE INVENTION

Embodiments of the present invention will be described below in detail with reference to the drawings. Note that the present invention is not limited to the following description, and various changes and modifications can be made without departing from the spirit and scope of the present invention. Therefore, the present invention should not be construed as being limited to the description in the following embodiments.

Note that the terms "film" and "layer" can be interchanged with each other depending on the case or circumstances. For example, in some cases, the term "conductive film" can be used instead of the term "conductive layer," and the term "insulating layer" can be used instead of the term "insulating film."

Embodiment 1

In a light-emitting device of one embodiment of the present invention, a light-emitting element in which an EL layer including a light-emitting layer is provided between a pair of electrodes is used. For the light-emitting element, various structures can be employed; for example, a structure in which one EL layer is provided between a pair of electrodes (single structure) or a structure in which a plurality of EL layers are stacked with a charge-generation layer therebetween (tandem structure) can be employed. As one example of an element structure of the light-emitting element, a light-emitting element with a tandem structure including two EL layers will be described below with reference to FIG. 1A.

Figure 1A:
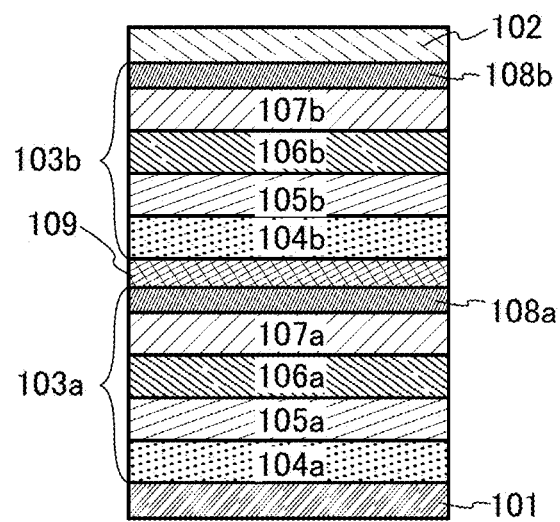
FIGS. 1A and 1B each illustrate a light-emitting element.

The light-emitting element illustrated in FIG. 1A has a structure in which two EL layers (103a and 103b) each including a light-emitting layer are provided between a pair of electrodes (a first electrode 101 and a second electrode 102). In the EL layer 103a, a hole-injection layer 104a, a hole-transport layer 105a, a light-emitting layer 106a, an electron-transport layer 107a, an electron-injection layer 108a, and the like are sequentially stacked over the first electrode 101. In the EL layer 103b, a hole-injection layer 104b, a hole-transport layer 105b, a light-emitting layer 106b, an electron-transport layer 107b, an electron-injection layer 108b, and the like are sequentially stacked over the first electrode 101. A charge-generation layer 109 is provided between the EL layer 103a and the EL layer 103b.

The light-emitting layers (106a and 106b) each contain a plurality of substances such as light-emitting substances in appropriate combination, and can emit fluorescent light or phosphorescent light of a desired emission color. Note that a light-emitting layer containing a different light-emitting substance from the light-emitting layer 106a or 106b may be further provided on the light-emitting layer 106a or 106b.

The charge-generation layer 109 has a function of injecting electrons into one of the EL layers (103a or 103b) and injecting holes into the other of the EL layers (103b or 103a) when a voltage is applied between the first electrode 101 and the second electrode 102. Thus, in FIG. 1A, when a voltage is applied such that the potential of the first electrode 101 is higher than that of the second electrode 102, the charge-generation layer 109 injects electrons into the EL layer 103a and injects holes into the EL layer 103b.

Note that in terms of light extraction efficiency, the charge-generation layer 109 preferably has a light-transmitting property with respect to visible light (specifically, the charge-generation layer 109 has a visible light transmittance of 40% or more). The charge-generation layer 109 functions even if it has lower conductivity than the first electrode 101 or the second electrode 102.

In the light-emitting element illustrated in FIG. 1A, light emitted in all directions from the light-emitting layers (106a and 106b) included in the EL layers (103a and 103b) can be resonated by the first electrode (reflective electrode) 101 and the second electrode (semi-transmissive and semi-reflective electrode) 102 which function as a micro optical resonator (microcavity). Light is emitted through the second electrode 102. The first electrode 101 is a reflective electrode, which has a stacked structure of a reflective conductive material and a transparent conductive material. Optical adjustment thereof is performed by controlling the thickness of the transparent conductive film. The optical adjustment may be performed by controlling the thickness of the hole-injection layer 104a included in the EL layer 103a.

As described above, the optical adjustment is performed by controlling the thickness of the first electrode 101 or the hole-injection layer 104a, whereby spectra of a plurality of rays of monochromatic light obtained from the light-emitting layers (106a and 106b) can be narrower, and light emission with high color purity can be obtained.

In the light-emitting element illustrated in FIG. 1A, the optical path length between the second electrode 102 functioning as a semi-transmissive and semi-reflective electrode and a light-emitting region in the EL layer 103b which is the nearest to the second electrode 102 is preferably smaller than $\lambda/4$ where $\lambda$ is the wavelength of light emitted from the light-emitting region. Here, the light-emitting region means a region where holes and electrons are recombined. With such a structure, light of standard white color can be obtained by a combination of a plurality of rays of monochromatic light from the light-emitting layers (106a and 106b) of the light-emitting element illustrated in FIG. 1A. The light-emitting layers (106a and 106b) emit, for example, blue light (e.g., with an emission spectrum peak in the range of 400 nm to 480 nm, preferably in the range of 450 nm to 470 nm), green light (e.g., with an emission spectrum peak in the range of 500 nm to 560 nm, preferably in the range of 520 nm to 555 nm), red light (e.g., with an emission spectrum peak in the range of 580 nm to 680 nm, preferably in the range of 600 nm to 620 nm), orange light (e.g., with an emission spectrum in the range of 580 nm to 610 nm, preferably in the range of 600 nm to 610 nm), or yellow light (e.g., with an emission spectrum peak in the range of 555 nm to 590 nm, preferably in the range of 570 nm to 580 nm). Further, as specific combinations of the emission colors of the light-emitting layers 106a and 106b (106a/106b), the following can be given: blue/green, blue/yellow, blue/red, green/blue, green/yellow, green/red, red/blue, red/green, and red/yellow.

Next, a specific example in manufacturing the above light-emitting element will be described.

The first electrode 101 is a reflective electrode and thus is formed using a conductive material having reflectivity, and a film whose visible light reflectivity is greater than or equal to 40% and less than or equal to 100%, preferably greater than or equal to 70% and less than or equal to 100%, and resistivity is $1\times10^{-2}$ Ωcm or lower is used. The second electrode 102 is formed using a conductive material having reflectivity and a conductive material having a light-transmitting property, and a film whose visible light reflectivity is greater than or equal to 20% and less than or equal to 80%, preferably greater than or equal to 40% and less than or equal to 70%, and whose resistivity is $1\times10^{-2}$ Ωcm or lower is used.

The optical path length between the first electrode 101 and the second electrode 102 is adjusted for each light having a desired wavelength so that light having a desired wavelength from the light-emitting layers (106a and 106b) is resonated and can be intensified. Specifically, the thickness of the transparent conductive film used for part of the first electrode 101 is changed so that the distance between the electrodes is $m\lambda/2$ (m is a natural number) where $\lambda$ is the desired wavelength of light.

Further, the optical path lengths between the first electrode 101 and the light-emitting layers (106a and 106b) emitting light having a desired wavelength are adjusted in order to intensify the light having a desired wavelength. Specifically, the thickness of the transparent conductive film that can be used for part of the first electrode 101 or the thickness of an organic film forming the hole-injection layer 104a is changed so that the optical path length is $(2m'+1)\lambda/4$ (m' is a natural number) where $\lambda$ is the desired wavelength of light.

In that case, the optical path length between the first electrode 101 and the second electrode 102 is, to be exact, represented by the total thickness from a reflective region in the first electrode 101 to a reflective region in the second electrode 102. However, it is difficult to exactly determine the reflective regions in the first electrode 101 and the second electrode 102; thus, it is assumed that the above effect can be sufficiently obtained wherever the reflective regions may be set in the first electrode 101 and the second electrode 102. Further, the optical path length between the first electrode 101 and the light-emitting layer emitting desired light is, to be exact, the optical length between the reflective region in the first electrode 101 and the light-emitting region in the light-emitting layer emitting desired light. However, it is difficult to exactly determine the reflective region in the first electrode 101 and the light-emitting region in the light-emitting layer emitting desired light; thus, it is assumed that the above effect can be sufficiently obtained wherever the reflective region and the light-emitting region may be set in the first electrode 101 and the light-emitting layer emitting desired light.

For the first electrode 101 and the second electrode 102, any of metals, alloys, electrically conductive compounds, mixtures thereof, and the like can be used as appropriate. Specific examples are indium oxide-tin oxide (indium tin oxide), indium oxide-tin oxide containing silicon or silicon oxide, indium oxide-zinc oxide (indium zinc oxide), indium oxide containing tungsten oxide and zinc oxide, gold (Au), platinum (Pt), nickel (Ni), tungsten (W), chromium (Cr), molybdenum (Mo), iron (Fe), cobalt (Co), copper (Cu), palladium (Pd), and titanium (Ti). In addition, an element belonging to Group 1 or Group 2 of the periodic table, for example, an alkali metal such as lithium (Li) or cesium (Cs), an alkaline earth metal such as calcium (Ca) or strontium (Sr), magnesium (Mg), an alloy containing such an element (MgAg, AlLi), a rare earth metal such as europium (Eu) or ytterbium (Yb), an alloy containing such an element, graphene, and the like can be used. The first electrode 101 and the second electrode 102 can be formed by, for example, a sputtering method or an evaporation method (including a vacuum evaporation method).

The hole-injection layers (104a and 104b) inject holes into the light-emitting layers (106a and 106b) through the hole-transport layers (105a and 105b) having a high hole-transport property, and can be formed using an acceptor material such as molybdenum oxide, vanadium oxide, ruthenium oxide, tungsten oxide, or manganese oxide. Alternatively, the hole-injection layers (104a and 104b) can be formed using a phthalocyanine-based compound such as phthalocyanine (abbreviation: H$_2$Pc) or copper phthalocyanine (abbreviation: CuPc), an aromatic amine compound such as 4,4'-bis[N-(4-diphenylaminophenyl)-N-phenylamino]biphenyl (abbreviation: DPAB) or N,N'-bis{4-[bis (3-methylphenyl)amino]phenyl}-N,N'-diphenyl-(1,1'-biphenyl)-4,4'-diamine (abbreviation: DNTPD), a compound containing an electron-withdrawing group (halogen or a cyano group) such as 7,7,8,8-tetracyano-2,3,5,6-tetrafluoro-quinodimethane (abbreviation: $F_4$-TCNQ), chloranil, or 2,3,6,7,10,11-hexacyano-1,4,5,8,9,12-hexaazatriphenylene (abbreviation: HAT-CN), or an organic acceptor material such as poly(3,4-ethylenedioxythiophene)/poly(styrenesulfonic acid) (abbreviation: PEDOT/PSS).

The hole-injection layers (104a and 104b) may contain a hole-transport material and an acceptor substance. When the hole-injection layers (104a and 104b) contain a hole-transport material and an acceptor substance, electrons are extracted from the hole-transport material by the acceptor substance to generate holes and the holes are injected into the light-emitting layers (106a and 106b) through the hole-transport layers (105a and 105b). The hole-transport layers (105a and 105b) are formed using a hole-transport material.

Specific examples of the hole-transport material, which is used for the hole-injection layers (104a and 104b) and the hole-transport layers (105a and 105b), include aromatic amine compounds such as 4,4'-bis[N-(1-naphthyl)-N-phenylamino]biphenyl (abbreviation: NPB or α-NPD), N,N'-bis(3-methylphenyl)-N,N-diphenyl-[1,1'-biphenyl]-4,4'-diamine (abbreviation: TPD), 4,4',4"-tris(carbazol-9-yl) triphenylamine (abbreviation: TCTA), 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), and 4,4'-bis[N-(spiro-9,9'-bifluoren-2-yl)-N-phenylamino]biphenyl (abbreviation: BSPB); 3-[N-(9-phenylcarbazol-3-yl)-N-phenylamino]-9-phenylcarbazole (abbreviation: PCzPCA1); 3,6-bis[N-(9-phenylcarbazol-3-yl)-N-phenylamino]-9-phenylcarbazole (abbreviation: PCzPCA2); and 3-[N-(1-naphthyl)-N-(9-phenylcarbazol-3-yl)amino]-9-phenylcarbazole (abbreviation: PCzPCN1). Other examples include carbazole derivatives such as 4,4'-di(N-carbazolyl)biphenyl (abbreviation: CBP), 1,3,5-tris[4-(N-carbazolyl)phenyl]benzene (abbreviation: TCPB), and 9-[4-(10-phenyl-9-anthracenyl)phenyl]-9H-carbazole (abbreviation: CzPA). The substances listed here are mainly ones that have a hole mobility of $10^{-6}$ $cm^2/Vs$ or higher. Note that any substance other than the substances listed here may be used as long as the hole-transport property is higher than the electron-transport property.

Other examples include high molecular compounds such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N-phenylamino}phenyl)methacrylamide] (abbreviation: PTPDMA), and poly[N,N'-bis(4-butylphenyl)-N,N'-bis(phenyl)benzidine] (abbreviation: Poly-TPD).

Examples of the acceptor substance used for the hole-injection layers (105a and 105b) include the above acceptor material and an organic acceptor material. Among them, an oxide of a metal belonging to any of Groups 4 to 8 of the periodic table is preferably used; in particular, molybdenum oxide is preferably used.

The light-emitting layers (106a and 106b) each contain a light-emitting substance. The light-emitting layers (106a and 106b) each contain an electron-transport material that is an organic compound and/or a hole-transport material in addition to the light-emitting substance; in the light-emitting element of one embodiment of the present invention, one of the light-emitting layers (106a and 106b) contains a fluorescent substance whose emission spectrum in a toluene solution of the fluorescent substance has a peak wavelength of 440 nm to 460 nm, preferably 440 nm to 455 nm or an organic compound in which two benzo[b]naphtho[1,2-d] furanylamine skeletons are bonded to a pyrene skeleton. The emission spectrum of the fluorescent substance preferably has a half-width greater than or equal to 20 nm and less than or equal to 50 nm.

As the fluorescent substance whose emission spectrum in a toluene solution has a peak wavelength of 440 nm to 460 nm, for example, a substance having an aromatic diamine skeleton is preferably used. More preferably, a substance having a pyrenediamine skeleton is used. As the substance having a pyrenediamine skeleton, to be more specific, an organic compound in which two benzo[b]naphtho[1,2-d] furanylamine skeletons are bonded to a pyrene skeleton and which is represented by General Formula (G1) below is preferably used. Note that the fluorescent substance that can be used in this embodiment is not limited to the following example.

As the organic compound in which two benzo[b]naphtho [1,2-d]furanylamine skeletons are bonded to a pyrene skeleton, an organic compound represented by General Formula (G1) below can be used. Note that the organic compound represented by General Formula (G1) below exhibits blue fluorescence.

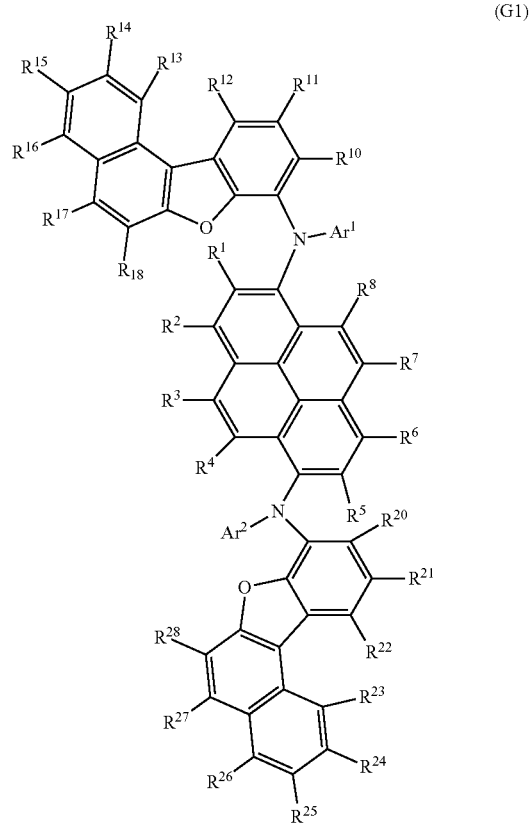

(G1)

In General Formula (G1), each of $Ar^1$ and $Ar^2$ independently represents a substituted or unsubstituted aryl group having 6 to 13 carbon atoms forming a ring; and each of $R^1$ to $R^8$, $R^{10}$ to $R^{18}$, and $R^{20}$ to $R^{28}$ independently represents hydrogen, a substituted or unsubstituted alkyl group having 1 to 6 carbon atoms, a substituted or unsubstituted alkoxy group having 1 to 6 carbon atoms, a cyano group, halogen, a substituted or unsubstituted haloalkyl group having 1 to 6 carbon atoms, or a substituted or unsubstituted aryl group having 6 to 10 carbon atoms.

For specific examples of the organic compound represented by General Formula (G1), Embodiment 2 can be referred to.

There is no particular limitation on a material that can be used as a light-emitting substance for the other of the light-emitting layers (106a and 106b), and a light-emitting material which converts singlet excitation energy into light emission in a visible light region or a light-emitting material which converts triplet excitation energy into light emission in a visible light region can be used.

As an example of the light-emitting material which converts singlet excitation energy into light emission in a visible light region, a substance emitting fluorescence can be given. Examples of the substance emitting fluorescence include a pyrene derivative, an anthracene derivative, a triphenylene derivative, a fluorene derivative, a carbazole derivative, a dibenzothiophene derivative, a dibenzofuran derivative, a dibenzoquinoxaline derivative, a quinoxaline derivative, a pyridine derivative, a pyrimidine derivative, a phenanthrene derivative, and a naphthalene derivative. A pyrene derivative is particularly preferable because it has a high emission quantum yield. Specific examples of the pyrene derivative include N,N'-bis(3-methylphenyl)-N,N'-bis[3-(9-phenyl-9H-fluoren-9-yl)phenyl]pyrene-1,6-diamine (1,6mMemFLPAPrn), N,N'-bis[4-(9-phenyl-9H-fluoren-9-yl)phenyl]-N,N-diphenylpyrene-1,6-diamine (1,6FLPAPrn), N,N'-bis(dibenzofuran-2-yl)-N,N-diphenylpyrene-1,6-diamine (1,6FrAPrn), and N,N'-bis(dibenzothiophen-2-yl)-N,N-diphenylpyrene-1,6-diamine (1,6ThAPrn).

Examples of the light-emitting material which converts triplet excitation energy into light emission in a visible light region include a substance emitting phosphorescence and a thermally activated delayed fluorescence (TADF) material. Note that the TADF material is a material that can up-convert a triplet excited state into a singlet excited state (i.e., reverse intersystem crossing is possible) using a little thermal energy and efficiently exhibits light emission (fluorescence) from the singlet excited state. The TADF is efficiently obtained under the condition where the difference in energy between the triplet excited level and the singlet excited level is greater than or equal to 0 eV and less than or equal to 0.2 eV, preferably greater than or equal to 0 eV and less than or equal to 0.1 eV. Note that "delayed fluorescence" exhibited by the TADF material refers to light emission having the same spectrum as normal fluorescence and an extremely long lifetime. The lifetime is $10^{-6}$ seconds or longer, preferably $10^{-3}$ seconds or longer.

As the substance emitting phosphorescence, an iridium-, rhodium-, or platinum-based organometallic complex or metal complex can be used; in particular, an organoiridium complex such as an iridium-based ortho-metalated complex is preferable. As an ortho-metalated ligand, a 4H-triazole ligand, a 1H-triazole ligand, an imidazole ligand, a pyridine ligand, a pyrimidine ligand, a pyrazine ligand, an isoquinoline ligand, and the like can be given. As the metal complex, a platinum complex having a porphyrin ligand and the like can be given. Examples of the substance emitting phosphorescence include bis[2-(3',5'bistrifluoromethylphenyl)pyridinato-N,$C^{2'}$]iridium(III)picolinate (abbreviation: Ir(CF$_3$ppy)$_2$(pic)), bis[2-(4',6'-difluorophenyl)pyridinato-N,$C^{2'}$]iridium(III) acetylacetonate (abbreviation: FIracac), tris(2-phenylpyridinato)iridium(III) (abbreviation: Ir(ppy)$_3$), bis(2-phenylpyridinato)iridium(III) acetylacetonate (abbreviation: Ir(ppy)$_2$(acac)), tris(acetylacetonato) (monophenanthroline)terbium(III) (abbreviation: Tb(acac)$_3$(Phen)), bis(benzo[h]quinolinato)iridium(III) acetylacetonate (abbreviation: Ir(bzq)$_2$(acac)), bis(2,4-diphenyl-1,3-oxazolato-N,$C^{2'}$)iridium(III) acetylacetonate (abbreviation: Ir(dpo)$_2$(acac)), bis{2-[4'-(perfluorophenyl)phenyl]pyridinato-N,$C^{2'}$}iridium(III) acetylacetonate (abbreviation: Ir(p-PF-ph)$_2$(acac)), bis(2-phenylbenzothiazolato-N,$C^{2'}$)iridium(III) acetylacetonate (abbreviation: Ir(bt)$_2$(acac)), bis[2-(2'-benzo[4,5-a]thienyl)pyridinato-N,$C^{3'}$]iridium(III) acetylacetonate (abbreviation: Ir(btp)$_2$(acac)), bis(1-phenylisoquinolinato-N,$C^{2'}$)iridium(III) acetylacetonate (abbreviation: Ir(piq)$_2$(acac)), (acetylacetonato)bis[2,3-bis(4-fluorophenyl)quinoxalinato]iridium(III) (abbreviation: Ir(Fdpq)$_2$(acac)), (acetylacetonato)bis(3,5-dimethyl-2-phenylpyrazinato)iridium(III) (abbreviation: [Ir(mppr-Me)$_2$(acac)]), (acetylacetonato)bis(5-isopropyl-3-methyl-2-phenylpyrazinato)iridium(III) (abbreviation: [Ir(mppr-iPr)$_2$(acac)]), (acetylacetonato)bis(2,3,5-triphenylpyrazinato)iridium(III) (abbreviation: Ir(tppr)$_2$(acac)) bis(2,3,5-triphenylpyrazinato) (dipivaloylmethanato)iridium(III) (abbreviation: [Ir(tppr)$_2$(dpm)]) (acetylacetonato)bis(6-tert-butyl-4-phenylpyrimidinato)iridium(III) (abbreviation: [Ir(tBuppm)$_2$(acac)]), (acetylacetonato)bis(4,6-diphenylpyrimidinato)iridium(III) (abbreviation: [Ir(dppm)$_2$(acac)]), 2,3,7,8,12,13,17,18-octaethyl-21H,23H-porphyrin platinum (II) (abbreviation: PtOEP), tris(1,3-diphenyl-1,3-propanedionato) (monophenanthroline)europium(III) (abbreviation: Eu(DBM)$_3$(Phen)), and tris[1-(2-thenoyl)-3,3,3-trifluoroacetonato] (monophenanthroline)europium(III) (abbreviation: Eu(TTA)$_3$(Phen)).

Specific examples of the TADF material include fullerene, a derivative thereof, an acridine derivative such as proflavine, and eosin. Other examples include a metal-containing porphyrin, such as a porphyrin containing magnesium (Mg), zinc (Zn), cadmium (Cd), tin (Sn), platinum (Pt), indium (In), or palladium (Pd). Examples of the metal-containing porphyrin include a protoporphyrin-tin fluoride complex (SnF$_2$(Proto IX)), a mesoporphyrin-tin fluoride complex (SnF$_2$(Meso IX)), a hematoporphyrin-tin fluoride complex (SnF$_2$(Hemato IX)), a coproporphyrin tetramethyl ester-tin fluoride complex (SnF$_2$(Copro III-4Me)), an octaethylporphyrin-tin fluoride complex (SnF$_2$(OEP)), an etioporphyrin-tin fluoride complex (SnF$_2$(Etio I)), and an octaethylporphyrin-platinum chloride complex (PtCl$_2$OEP). Alternatively, a heterocyclic compound including a π-electron rich heteroaromatic ring and a π-electron deficient heteroaromatic ring can be used, such as 2-(biphenyl-4-yl)-4,6-bis(12-phenylindolo[2,3-a]carbazol-11-yl)-1,3,5-triazine (PIC-TRZ). Note that a material in which the π-electron rich heteroaromatic ring is directly bonded to the π-electron deficient heteroaromatic ring is particularly preferable because both the donor property of the π-electron rich heteroaromatic ring and the acceptor property of the π-electron deficient heteroaromatic ring are increased and the energy difference between the S$_1$ level and the T$_1$ level becomes small.

As a material that can be used as the light-emitting substance for the other of the light-emitting layers (106a and 106b), a light-emitting material which converts triplet excitation energy into light emission in a visible light region is preferably used. More preferably, a phosphorescent substance which exhibits yellow phosphorescence is used. With such a structure, a light-emitting element with low power consumption can be obtained. With the use of such a light-emitting element as a display element of a light-emitting device, power consumption for obtaining white emission can be effectively reduced.

In the case where an electron-transport material is used as the organic compound for the light-emitting layers (106a and 106b), a π-electron deficient heteroaromatic compound such as a nitrogen-containing heteroaromatic compound is preferable, examples of which include quinoxaline derivatives and dibenzoquinoxaline derivatives such as 2-[3-(dibenzothiophen-4-yl)phenyl]dibenzo[f;h]quinoxaline (abbreviation: 2mDBTPDBq-II), 2-[3'-(dibenzothiophen-4-yl)biphenyl-3-yl]dibenzo[f;h]quinoxaline (abbreviation: 2mDBTBPDBq-II), 2-[4-(3,6-diphenyl-9H-carbazol-9-yl)phenyl]dibenzo[f;h]quinoxaline (abbreviation: 2CzPDBq-III), 7-[3-(dibenzothiophen-4-yl)phenyl]dibenzo[f;h]quinoxaline (abbreviation: 7mDBTPDBq-II), and 6-[3-(dibenzothiophen-4-yl)phenyl]dibenzo[f;h]quinoxaline (abbreviation: 6mDBTPDBq-II).

In the case where a hole-transport material is used as the organic compound for the light-emitting layers (106a and 106b), π-electron rich heteroaromatic compound (e.g., a carbazole derivative or an indole derivative) or an aromatic amine compound is preferable, examples of which include 4-phenyl-4'-(9-phenyl-9H-carbazol-3-yl)triphenylamine (abbreviation: PCBA1BP), 4,4'-di(1-naphthyl)-4''-(9-phenyl-9H-carbazol-3-yl)triphenylamine (abbreviation: PCBNBB), 3-[N-(1-naphthyl)-N-(9-phenylcarbazol-3-yl)amino]-9-phenylcarbazole (abbreviation: PCzPCN1), 4,4',4''-tris[N-(1-naphthyl)-N-phenylamino]triphenylamine (abbreviation: 1'-TNATA), 2,7-bis[N-(4-diphenylaminophenyl)-N-phenylamino]-spiro-9,9'-bifluorene (abbreviation: DPA2SF), N,N'-bis(9-phenylcarbazol-3-yl)-N,N'-diphenylbenzene-1,3-diamine (abbreviation: PCA2B), N-(9,9-dimethyl-2-diphenylamino-9H-fluoren-7-yl)diphenylamine (abbreviation: DPNF), N,N',N''-triphenyl-N,N',N''-tris(9-phenylcarbazol-3-yl)benzene-1,3,5-triamine (abbreviation: PCA3B), 2-[N-(9-phenylcarbazol-3-yl)-N-phenylamino]spiro-9,9'-bifluorene (abbreviation: PCASF), 2-[N-(4-diphenylaminophenyl)-N-phenylamino]spiro-9,9'-bifluorene (abbreviation: DPASF), N,N'-bis[4-(carbazol-9-yl)phenyl]-N,N'-diphenyl-9,9-dimethylfluorene-2,7-diamine (abbreviation: YGA2F), 4,4'-bis[N-(3-methylphenyl)-N-phenylamino]biphenyl (abbreviation: TPD), 4,4'-bis[N-(4-diphenylaminophenyl)-N-phenylamino]biphenyl (abbreviation: DPAB), N-(9,9-dimethyl-9H-fluoren-2-yl)-N-{9,9-dimethyl-2-[N'-phenyl-N'-(9,9-dimethyl-9H-fluoren-2-yl)amino]-9H-fluoren-7-yl}phenylamine (abbreviation: DFLADFL), 3-[N-(9-phenylcarbazol-3-yl)-N-phenylamino]-9-phenylcarbazole (abbreviation: PCzPCA1), 3-[N-(4-diphenylaminophenyl)-N-phenylamino]-9-phenylcarbazole (abbreviation: PCzDPA1), 3,6-bis[N-(4-diphenylaminophenyl)-N-phenylamino]-9-phenylcarbazole (abbreviation: PCzDPA2), 4,4'-bis(N-{4-[N'-(3-methylphenyl)-N'-phenylamino]phenyl}-N-phenylamino)biphenyl (abbreviation: DNTPD), 3,6-bis[N-(4-diphenylaminophenyl)-N-(1-naphthyl)amino]-9-phenylcarbazole (abbreviation: PCzTPN2), and 3,6-bis[N-(9-phenylcarbazol-3-yl)-N-phenylamino]-9-phenylcarbazole (abbreviation: PCzPCA2).

In the case where the light-emitting substance used for the light-emitting layer is a substance emitting phosphorescence, examples of the organic compound used for the light-emitting layer include an aromatic amine and a carbazole derivative in addition to a zinc- or aluminum-based metal complex, an oxadiazole derivative, a triazole derivative, a benzimidazole derivative, a quinoxaline derivative, a dibenzoquinoxaline derivative, a dibenzothiophene derivative, a dibenzofuran derivative, a pyrimidine derivative, a triazine derivative, a pyridine derivative, a bipyridine derivative, and a phenanthroline derivative.

In the case where the light-emitting substance used for the light-emitting layer is a substance emitting fluorescence, an anthracene derivative or a tetracene derivative whose $S_1$ level is high and $T_1$ level is low is preferably used. Specific examples include 9-phenyl-3-[4-(10-phenyl-9-anthryl)phenyl]-9H-carbazole (PCzPA), 9-[4-(10-phenyl-9-anthracenyl)phenyl]-9H-carbazole (CzPA), 7-[4-(10-phenyl-9-anthryl)phenyl]-7H-dibenzo[c,g]carbazole (cgDBCzPA), 6-[3-(9,10-diphenyl-2-anthryl)phenyl]-benzo[b]naphtho[1,2-d]furan (2mBnfPPA), 9-phenyl-10-{4-(9-phenyl-9H-fluoren-9-yl)biphenyl-4'-yl}anthracene (FLPPA), 5,12-diphenyltetracene, and 5,12-bis(biphenyl-2-yl)tetracene.

The electron-transport layers (107a and 107b) are layers containing a substance with a high electron-transport property. For the electron-transport layers (107a and 107b), a metal complex such as $Alq_3$, tris(4-methyl-8-quinolinolato)aluminum (abbreviation: $Almq_3$), bis(10-hydroxybenzo[h]quinolinato)beryllium(II) (abbreviation: $BeBq_2$), BAlq, $Zn(BOX)_2$, or bis[2-(2-hydroxyphenyl)benzothiazolato]zinc (II) (abbreviation: $Zn(BTZ)_2$) can be used. Moreover, a heteroaromatic compound such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-tert-biphenylyl)-4-phenyl-5-(4-butylphenyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), or 4-4'-bis(5-methylbenzoxazol-2-yl)stilbene (abbreviation: BzOs) can be used, as well. Further alternatively, it is possible to use a high molecular compound such as poly(2,5-pyridinediyl) (abbreviation: PPy), poly[(9,9-dihexylfluorene-2,7-diyl)-co-(pyridine-3,5-diyl)] (abbreviation: PF-Py) or poly[(9,9-dioctylfluorene-2,7-diyl)-co-(2,2'-bipyridine-6,6'-diyl)] (abbreviation: PF-BPy). The substances mentioned here are mainly ones that have an electron mobility of $1 \times 10^{-6}$ $cm^2/Vs$ or higher. However, any substance other than the above substances may also be used for the electron-transport layers (107a and 107b) as long as the electron-transport property is higher than the hole-transport property.

Each of the electron-transport layers (107a and 107b) is not limited to a single layer, and may be a stack including two or more layers containing any of the above substances.

The electron-injection layers (108a and 108b) are layers containing a substance with a high electron-injection property. For the electron-injection layers (108a and 108b), an alkali metal, an alkaline earth metal, or a compound thereof such as lithium fluoride (LiF), cesium fluoride (CsF), calcium fluoride ($CaF_2$), or lithium oxide ($LiO_x$) can be used. A rare earth metal compound like erbium fluoride ($ErF_3$) can also be used. An electride may also be used for the electron-injection layers (108a and 108b). Examples of the electride include a substance in which electrons are added at high concentration to calcium oxide-aluminum oxide. Any of the substances for forming the electron-transport layers (107a and 107b), which are listed above, can also be used.

The electron-injection layers (108a and 108b) each may be formed using a composite material in which an organic compound and an electron donor are mixed. The composite material is superior in an electron-injection property and an electron-transport property, since electrons are generated in the organic compound by the electron donor. In this case, the organic compound is preferably a material that is excellent in transporting the generated electrons. Specifically, for example, the substances for forming the electron-transport layers (107a and 107b) (e.g., a metal complex or a heteroaromatic compound), which are given above, can be used. As the electron donor, a substance showing an electron-donating property with respect to the organic compound may be used. Specifically, an alkali metal, an alkaline earth metal, and a rare earth metal are preferable, and lithium, cesium, magnesium, calcium, erbium, ytterbium, and the like are given. In addition, an alkali metal oxide or an alkaline earth metal oxide is preferable, and lithium oxide, calcium oxide, and barium oxide are given. A Lewis base such as magnesium oxide can also be used. An organic compound such as tetrathiafulvalene (abbreviation: TTF) can also be used.

In the light-emitting element described in this embodiment, the optical path length between the second electrode 102 and the light-emitting region in the EL layer 103b which is the nearest to the second electrode 102 is preferably smaller than $\lambda/4$ where $\lambda$ is the wavelength of light emitted from the light-emitting region. For that reason, the total thickness of the electron-transport layer (107b) and the electron-injection layer (108b) is preferably adjusted as appropriate so that the optical path length between the second electrode 102 and the light-emitting region in the EL layer 103b which is the nearest to the second electrode 102 can be smaller than $\lambda/4$.

The charge-generation layer 109 may have either a structure in which an electron acceptor (acceptor) is added to a hole-transport material or a structure in which an electron donor (donor) is added to an electron-transport material. Alternatively, both of these structures may be stacked.

In the case of the structure in which an electron acceptor is added to a hole-transport material, as the hole-transport material, for example, an aromatic amine compound such as NPB, TPD, TDATA, MTDATA, or 4,4'-bis[N-(spiro-9,9'-bifluoren-2-yl)-N-phenylamino]biphenyl (abbreviation: BSPB) can be used. The substances listed here are mainly ones that have a hole mobility of $10^{-6}$ cm$^2$/Vs or higher. Note that any substance other than the above substances may be used as long as the hole-transport property is higher than the electron-transport property.

Examples of the electron acceptor include 7,7,8,8-tetracyano-2,3,5,6-tetrafluoroquinodimethane (abbreviation: F$_4$-TCNQ), chloranil, and HAT-CN. Oxides of metals belonging to Groups 4 to 8 of the periodic table can also be used. Specifically, vanadium oxide, niobium oxide, tantalum oxide, chromium oxide, molybdenum oxide, tungsten oxide, manganese oxide, and rhenium oxide are preferable because of their high electron-accepting properties. Among these, molybdenum oxide is especially preferable because it is stable in the air, has a low hygroscopic property, and is easy to handle.

On the other hand, in the case of the structure in which an electron donor is added to an electron-transport material, as the electron-transport material, for example, a metal complex having a quinoline skeleton or a benzoquinoline skeleton, such as Alq, Almq$_3$, BeBq$_2$, or BAlq can be used. Alternatively, a metal complex having an oxazole-based ligand or a thiazole-based ligand, such as Zn(BOX)$_2$ or Zn(BTZ)$_2$ can be used. Further alternatively, in addition to such a metal complex, PBD, OXD-7, TAZ, BPhen, BCP, or the like can be used. The substances listed here are mainly ones that have an electron mobility of $10^{-6}$ cm$^2$/Vs or higher. Note that any substance other than the substances listed here may be used as long as the electron-transport property is higher than the hole-transport property.

As the electron donor, it is possible to use an alkali metal, an alkaline earth metal, a rare earth metal, a metal belonging to Group 2 or 13 of the periodic table, or an oxide or carbonate thereof. Specifically, lithium (Li), cesium (Cs), magnesium (Mg), calcium (Ca), ytterbium (Yb), indium (In), lithium oxide, cesium carbonate, or the like is preferably used. Alternatively, an organic compound such as tetrathianaphthacene may be used as the electron donor.

Note that by the formation of the charge-generation layer 109 using any of the above materials, it is possible to suppress an increase in driving voltage caused by stacking the EL layers.

Note that each of the hole-injection layers (104a and 104b), the hole-transport layers (105a and 105b), the light-emitting layers (106a and 106b), the electron-transport layers (107a and 107b), the electron-injection layers (108a and 108b), and the charge-generation layer 109 can be formed by a method such as an evaporation method (e.g., a vacuum evaporation method), an ink-jet method, or a coating method.

Although the light-emitting element having two EL layers is described in this embodiment, a light-emitting element in which three or more EL layers are stacked can also be used.

Figure 1B:
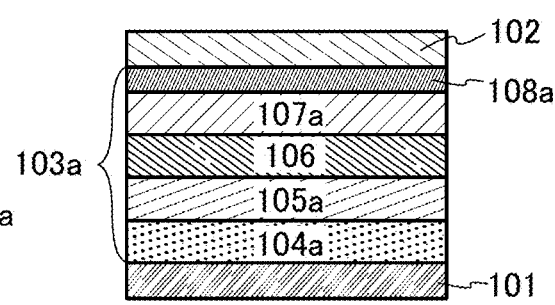

Note that a light-emitting element of the present invention may have a single structure of one EL layer as illustrated in FIG. 1B. In this case, the light-emitting layer 106 includes the first light-emitting layer 106a and the second light-emitting layer 106b. For the structures of the other components, the above description of the layers denoted by the same reference numerals can be referred to.

Figure 27:
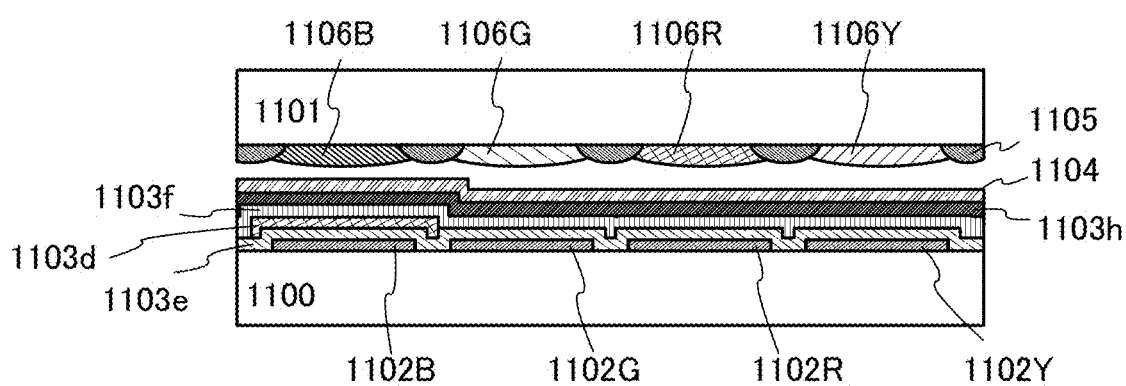
FIG. 27 illustrates a structure of a light-emitting element.

In the case of the single structure, emission efficiency can be improved with a separate coloring structure illustrated in FIG. 27. Even when coloring is performed only once, the emission efficiency of a light-emitting element with the structure illustrated in FIG. 27 can be equivalent to that of a light-emitting element in which light-emitting layers are separately colored (in the case of blue and yellow, coloring is performed twice).

A substrate 1100, first electrodes (1102B, 1102G, 1102R, and 1102Y) provided over the substrate 1100, a second electrode 1104, a black matrix 1105, color filters (1106B, 1106G, 1106R, and 1106Y), and a sealing substrate 1101 in the separate coloring structure are similar to the components in FIGS. 1A and 1B. As for an EL layer, a hole-injection layer and hole-transport layer 1103e, a yellow light-emitting layer 1103f, and an electron-transport layer and electron-injection layer 1103h can be used for all the light-emitting elements; only a blue light-emitting layer 1103d is separately colored and is provided in a portion where a blue light-emitting element is formed.

Here, in the yellow light-emitting layer 1103f and the blue light-emitting layer 1103d, carrier balance is adjusted so that a recombination region can be formed on the electrode side which is closer to the light-emitting layer that is separately colored (in this case, the blue light-emitting layer). In FIG. 27, the blue light-emitting layer 1103d is separately colored and is closer to the first electrode (here, anode) than the yellow light-emitting layer is; thus, host materials and light-emitting materials for the blue light-emitting layer and the yellow light-emitting layer are selected such that the electron-transport property of each of the blue light-emitting layer and the yellow light-emitting layer is higher than the hole-transport property thereof. With such a structure, only blue light emission can be obtained from the light-emitting element including the blue light-emitting layer 1103d, and only yellow light emission can be obtained from the other elements, and the emission efficiency can be equivalent to that of an element in which a blue light-emitting layer and a yellow light-emitting layer are separately colored.

The light emission mechanism of the above light-emitting element depends on the structure of the light-emitting layer, and will be described below with reference to FIG. 2, FIG. 3, and FIG. 4.

(1) First, two kinds of light emission mechanisms in the case where the light-emitting layer (106a or 106b) contains a light-emitting substance (a guest material 121) and a first organic compound (a host material 122) and the light-emitting substance (the guest material 121) is a substance that emits fluorescence will be described.

Note that in the light-emitting layer (106a or 106b), excited states are formed by carrier recombination; the excited states are formed mostly as the excited states of the host material 122 because the host material 122 is present in larger amounts than the guest material 121. Here, the ratio of the singlet excited state to the triplet excited state formed by carrier recombination (hereinafter, exciton generation probability) is approximately 1:3.

(i) When the $T_1$ level of the host material 122 is higher than the $T_1$ level of the guest material 121

Energy is transferred from the host material 122 in the triplet excited state to the guest material 121 (triplet energy transfer); however, since the guest molecule is a fluorescent substance, its triplet excited state does not provide light emission. Further, since the guest molecule is present in small amounts in the light-emitting layer, triplet-triplet annihilation (TTA) is unlikely to occur and thus the triplet excited state of the guest molecule is thermally deactivated. Therefore, a triplet exciton cannot be utilized for light emission; approximately 25% of injected carriers can be utilized for light emission at a maximum.

(ii) When the $T_1$ level of the host material 122 is lower than the $T_1$ level of the guest material 121

Figure 2:
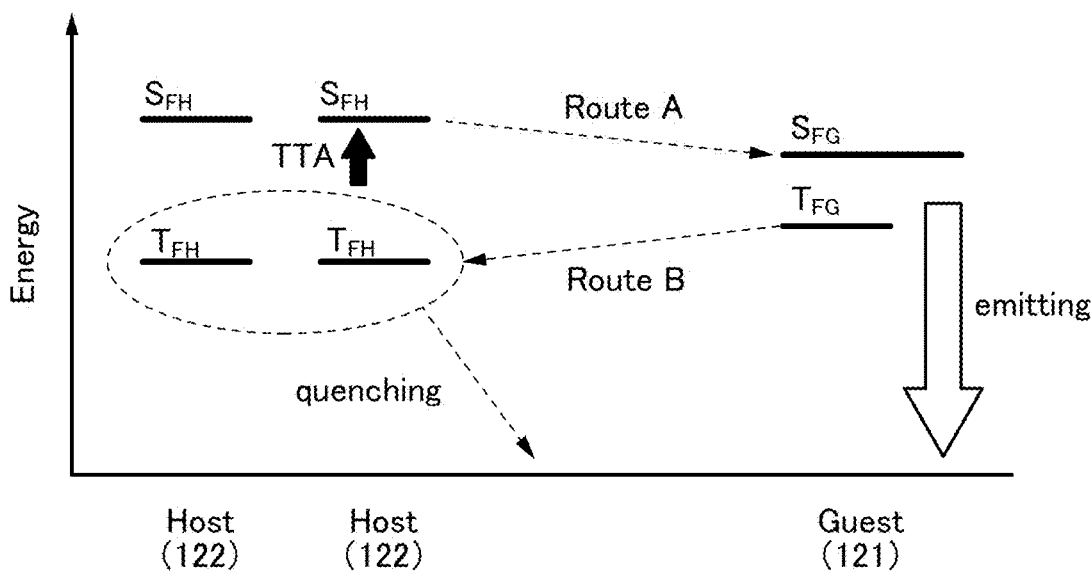
FIG. 2 shows a light emission mechanism of a light-emitting element.

The correlation of energy levels of the host material 122 and the guest material 121 is shown in FIG. 2. The following explains what terms and signs in FIG. 2 represent:

Guest: the guest material 121 (fluorescent material);
Host: the host material 122;
$S_{FH}$: the level of the lowest singlet excited state of the host material 122;
$T_{FH}$: the level of the lowest triplet excited state of the host material 122;
$S_{FG}$: the level of the lowest singlet excited state of the guest material 121 (fluorescent material); and
$T_{FG}$: the level of the lowest triplet excited state of the guest material 121 (fluorescent material).

In this case, the host molecule is present in large amounts in the light-emitting layer, so that triplet-triplet annihilation (TTA) is likely to occur; thus, some of the triplet excitons in the host material 122 are converted into the level of the lowest single excited state of the host material 122 ($S_{FH}$). Then, energy is transferred from the level of the lowest single excited state of the host material 122 ($S_H$) to the level of the lowest singlet excited state of the guest material 121 ($S_{FG}$) (Route A). Consequently, the guest material 121 emits light.

Since the $T_1$ level of the host material 122 ($T_{FH}$) is lower than the $T_1$ level of the guest material 121 ($T_{FG}$), even in the case where carriers are directly recombined in the guest material 121 and the triplet exciton is generated, energy is transferred from the $T_1$ level ($T_{FG}$) to the $T_1$ level of the host material 122 ($T_{FH}$) (Route B) and can be utilized for TTA. As a result, emission efficiency can be improved compared with the above case (i).

(2) Next, a light emission mechanism in the case where the light-emitting layer (106a or 106b) contains a light-emitting substance (a guest material 131), a first organic compound 132, and a second organic compound 133 and the light-emitting substance (the guest material 131) is a substance that emits phosphorescence will be described. Note that the first organic compound 132 serves as a host material, and the weight proportion of the first organic compound 132 in the light-emitting layer is larger than that of the second organic compound 133 in the light-emitting layer.

In the light-emitting layer (106a or 106b), there is no particular limitation on the combination of the first organic compound 132 and the second organic compound 133 as long as they can form an exciplex (excited complex) 134; however, it is preferable that one of them be a material having a hole-transport property and the other be a material having an electron-transport property. In that case, a donor-acceptor excited state is formed easily, which allows the exciplex 134 to be formed efficiently. In the case where the combination of the first organic compound 132 and the second organic compound 133 is a combination of the material having a hole-transport property and the material having an electron-transport property, the carrier balance can be controlled easily by adjusting the mixing ratio. Specifically, the ratio of the material having a hole-transport property to the material having an electron-transport property is preferably 1:9 to 9:1 (weight ratio). Since the carrier balance can be easily controlled with the above-described structure, a recombination region can also be easily controlled.

Figure 3:
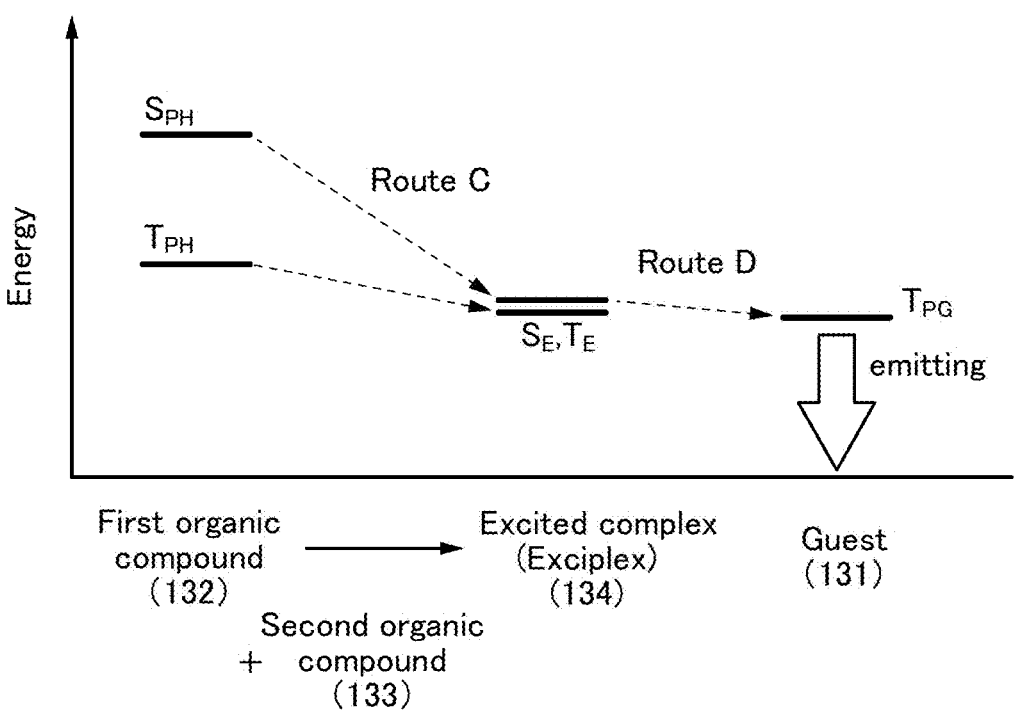
FIG. 3 shows a light emission mechanism of a light-emitting element.
Figure 4:
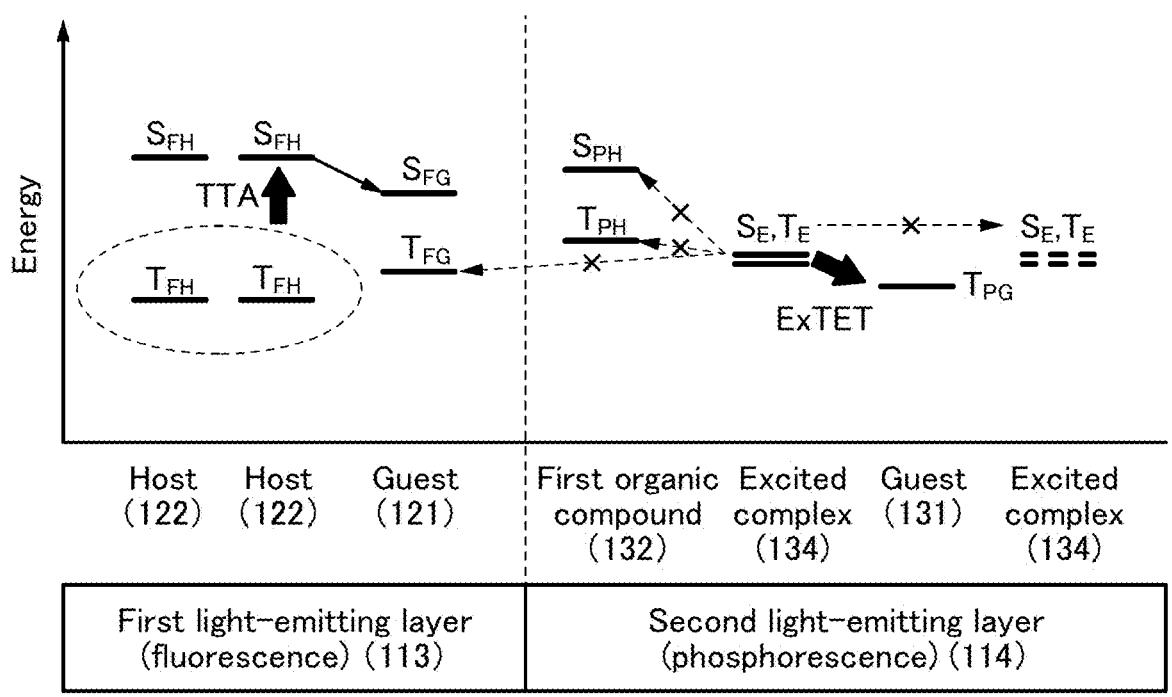
FIG. 4 shows a light emission mechanism of a light-emitting element.

The correlation of energy levels of the light-emitting substance (guest material) 131, the first organic compound 132, and the second organic compound 133 is shown in FIG. 3. The following explains what terms and signs in FIG. 3 represent:

Guest: the guest material (phosphorescent material) 131;
First organic compound: the first organic compound 132;
Second organic compound: the second organic compound 133;
Exciplex: the exciplex (excited complex) 134;
$S_{PH}$: the level of the lowest singlet excited state of the first organic compound 132:
$T_{PH}$: the level of the lowest triplet excited state of the first organic compound 132;
$T_{PG}$: the level of the lowest triplet excited state of the guest material (phosphorescent material) 131;
$S_E$: the level of the lowest singlet excited state of the exciplex 134; and
$T_E$: the level of the lowest triplet excited state of the exciplex 134.

In this case, the first organic compound 132 and the second organic compound 133 form the exciplex 134. The level of the lowest singlet excited state of the exciplex 134 ($S_E$) and the level of the lowest triplet excited state of the exciplex 134 ($T_E$) come close to each other (Route C).

Note that the exciplex 134 is in an excited state formed by two kinds of substances, and is formed by either photoexitation or electrical excitation. In the case of photoexcitation, the exciplex 134 is formed in such a manner that one molecule in an excited state of one substance forms a pair with one molecule in a ground state of the other substance. In the case of electrical excitation, there are two patterns of elementary processes in which the exciplex is formed. One of them is the same as in the case of photoexitation. The other is as follows: a cationic molecule (hole) of one substance comes close to an anionic molecule (electron) of the other substance, and thus the exciplex 134 is formed. At the start of light emission, the latter elementary process is dominant, and thus the exciplex 134 can be formed without the two kinds of substances being in an excited state. Therefore, emission start voltage can be lowered, and in addition, driving voltage can be reduced.

When the exciplex 134 is formed, energy is transferred from the level of the lowest singlet excited state of the exciplex 134 ($S_E$) and the level of the lowest triplet excited state of the exciplex 134 ($T_E$) to the level of the lowest triplet excited state of the guest material (phosphorescent material) 131 ($T_{PG}$) (Route D); thus, the guest material 131 emits light. Note that the process in which the exciplex 134 is formed (Route C) and energy is transferred from the exciplex 134 to the guest material (phosphorescent material) 131 (Route D) is referred to as exciplex-triplet energy transfer (ExTET).

When the exciplex 134 returns to a ground state by losing energy, the two kinds of substances that have formed the exciplex 134 serve as the original different substances.

Depending on the combination of the first organic compound and the second organic compound which form the exciplex, with the use of the fluorescent material as the guest material, the guest material (fluorescent material) can emit light by energy transfer from the exciplex to the guest material (fluorescent material). The fluorescent material includes in its category a thermally activated delayed fluorescence material.

(3) Then, a light emission mechanism in the case where one of the light-emitting layers (106a and 106b) has a stacked structure in which first light-emitting layer with the light emission mechanism (TTA) described in (ii) in (1) above and a second light-emitting layer with the light emission mechanism (ExTET) described in (2) above are in contact with each other will be described. The correlation of energy levels in this case is shown in FIG. 4. The following explains what terms and signs in FIG. 4 represent:

First light-emitting layer (fluorescence) 113: a first light-emitting layer 113;

Second light-emitting layer (phosphorescence) 114: a second light-emitting layer 114;

$S_{FH}$: the level of the lowest singlet excited state of the host material 122;

$T_{FH}$: the level of the lowest triplet excited state of the host material 122;

$S_{FG}$: the level of the lowest singlet excited state of the guest material (fluorescent material) 121;

$T_{FG}$: the level of the lowest triplet excited state of the guest material (fluorescent material) 121;

$S_{PH}$: the level of the lowest singlet excited state of the first organic compound 132;

$T_{PH}$: the level of the lowest triplet excited state of the first organic compound 132;

$T_{PG}$: the level of the lowest triplet excited state of the guest material (phosphorescent material) 131;

$S_E$: the level of the lowest singlet excited state of the exciplex 134; and $T_E$: the level of the lowest triplet excited state of the exciplex 134.

Since the exciplex 134 formed in the second light-emitting layer 114 is present only in an excited state, exciton diffusion between the exciplexes 134 is unlikely to occur. Furthermore, since the excited level ($S_E$) of the exciplex 134 is lower than both the singlet excited level ($S_{PH}$) of the first organic compound 132 and the singlet excited level of the second organic compound in the second light-emitting layer 114, singlet excitation energy is not diffused from the exciplex 134 to the first organic compound 132 and the second organic compound. At the interface between the first light-emitting layer 113 and the second light-emitting layer 114, in the case where energy (in particular, triplet energy) is transferred from the exciplex 134 formed in the second light-emitting layer 114 (the level of the lowest singlet excited state of the exciplex ($S_E$) or the level of the lowest triplet excited state of the exciplex ($T_E$)) to the excited level ($S_{FH}$, $T_{FH}$) of the host material 122 in the first light-emitting layer 113, singlet excitation energy is converted into light emission through a normal route and triplet excitation energy is partly converted into light emission by TTA in the first light-emitting layer 113. As a result, energy loss can be reduced. Furthermore, exciton diffusion between the exciplexes does not occur, and thus the energy transfer from the exciplex to the first light-emitting layer 113 occurs only at the interface.

That most excitons in the second light-emitting layer 114 are present in a state of exciplex and excitation diffusion between the exciplexes 134 is unlikely to occur in the second light-emitting layer 114 means the emission efficiency of the second light-emitting layer 114 can be kept even in the case where the $T_1$ level of the host material 122 in the first light-emitting layer 113 that is a fluorescent layer is lower than the $T_1$ levels of the first organic compound 132 and the second organic compound 133 in the second light-emitting layer 114. That is, in this structure, with the use of, as the host material in the first light-emitting layer 113, a condensed aromatic compound such as an anthracene derivative which is electrochemically stable and highly reliable but has a low triplet excited level, light emission can be efficiently obtained from the phosphorescent layer which is adjacent to the first light-emitting layer 113. Therefore, that the $T_1$ level of the host material 122 in the first light-emitting layer 113 is lower than the $T_1$ levels of the first organic compound 132 and the second organic compound 133 in the second light-emitting layer 114 is one feature of this structure.

In the first light-emitting layer 113, it is preferable that the $S_1$ level (not illustrated) of the host material 122 be higher than the $S_1$ level of the guest material 121 and the $T_1$ level ($T_{FH}$) of the host material 122 be lower than the $T_1$ level ($T_{FG}$) of the guest material 121. With such a structure, even in the case where energy transfer occurs from the level ($T_E$) of the lowest triplet excited state of the exciplex 134 formed in the second light-emitting layer 114 to the level ($T_{FH}$) of the lowest triplet excited state of the host material 122 in the first light-emitting layer 113 at the interface between the first light-emitting layer 113 and the second light-emitting layer 114, the energy can be partly converted into light emission in the first light-emitting layer 113 by TTA. As a result, energy loss can be reduced.

In the case where the above stacked structure of the light-emitting layers is used, light emitted from the first light-emitting layer 113 preferably has a peak on the shorter wavelength side than light emitted from the second light-emitting layer 114. The reason for this is as follows. Since the luminance of a light-emitting element using a phosphorescent material emitting light with a short wavelength tends to be degraded quickly, a light-emitting element with less degradation of luminance can be provided with the use of a fluorescent material emitting light with a shorter wavelength than light emitted from the second light-emitting layer 114.

In the case where the above stacked structure of the light-emitting layers is used, a third layer may be formed between the first light-emitting layer 113 and the second light-emitting layer 114 so that the first light-emitting layer 113 and the second light-emitting layer 114 are not in contact with each other. With such a structure, energy transfer (in particular, triplet energy transfer) from the excited state of the first organic compound 132 or the guest material (phosphorescent material) 131 formed in the second light-emitting layer 114 to the host material 122 or the guest material (fluorescent material) 121 in the first light-emitting layer 113 due to the Dexter mechanism can be prevented. Note that the third layer in such a structure may be formed with a thickness of several nanometers.

The third layer may be formed using a single material (hole-transport material or electron-transport material) or both a hole-transport material and an electron-transport material. In the case of a single material, a bipolar material may be used. The bipolar material here refers to a material in which the ratio between the electron mobility and the hole mobility is 100 or less. The third layer can be formed using the same material as the first light-emitting layer or the second light-emitting layer. Such a structure facilitates the fabrication of the light-emitting element and reduces the driving voltage.

The light-emitting element described in this embodiment preferably has a microcavity structure. With this, light (monochromatic light rays) with different wavelengths can be extracted even if the same EL layer is employed. In comparison with a separate coloring structure (for example, R, G, and B are separately colored), the above structure is advantageous for full color display owing to easiness in achieving higher resolution display or the like. Note that a combination with coloring layers (color filters) is also possible. With the microcavity structure, the intensity of light with a specific wavelength in the front direction can be increased, whereby power consumption can be reduced. The above structure is particularly effective in the case of being used for a backlight or a front light in a color display (image display device) including pixels of three or more colors but may also be used for a lighting device or the like.

As a light-emitting device including the above light-emitting element, a passive matrix light-emitting device and an active matrix light-emitting device can be fabricated. Each of the light-emitting devices is one embodiment of the present invention.

Note that there is no particular limitation on the structure of the transistor (FET) in the case of fabricating the active matrix light-emitting device. For example, a staggered FET or an inverted staggered FET can be used as appropriate. A driver circuit formed over an FET substrate may be formed using both an n-type FET and a p-type FET or only either an n-type FET or a p-type FET. Furthermore, there is no particular limitation on the crystallinity of a semiconductor film used for the FET. For example, either an amorphous semiconductor film or a crystalline semiconductor film may be used. Examples of a semiconductor material include Group 13 semiconductors (e.g., gallium), Group 14 semiconductors (e.g., silicon), compound semiconductors (including oxide semiconductors), and organic semiconductors.

Further, the light-emitting element described in this embodiment can be formed over a variety of substrates. There is no particular limitation on the type of substrate. Examples of the substrate include a semiconductor substrate (e.g., a single crystal substrate or a silicon substrate), an SOI substrate, a glass substrate, a quartz substrate, a plastic substrate, a metal substrate, a stainless steel substrate, a substrate including stainless steel foil, a tungsten substrate, a substrate including tungsten foil, a flexible substrate, an attachment film, paper including a fibrous material, and a base material film. Examples of a glass substrate include a barium borosilicate glass substrate, an aluminoborosilicate glass substrate, and a soda lime glass substrate. Examples of a flexible substrate, an attachment film, and a base material film include plastics typified by polyethylene terephthalate (PET), polyethylene naphthalate (PEN), and polyether sulfone (PES); a synthetic resin of acrylic or the like; polypropylene; polyester; polyvinyl fluoride; polyvinyl chloride; polyamide; polyimide; aramid; epoxy; an inorganic vapor deposition film; and paper.

When a transistor is formed together with the light-emitting element over any of these substrates, the use of a semiconductor substrate, a single crystal substrate, an SOI substrate, or the like enables the manufacture of small-sized transistors with a small variation in characteristics, size, shape, or the like and with high current capability. A circuit using such transistors achieves lower power consumption of the circuit or higher integration of the circuit.

When the above-described flexible substrate is used as a substrate over which a light-emitting element or a transistor is formed, the light-emitting element or the transistor may be directly formed over the flexible substrate. Alternatively, part of or the entire light-emitting element or transistor may be formed over a base substrate with a separation layer provided therebetween and then the light-emitting element or the transistor may be separated from the base substrate and transferred to another substrate. When the light-emitting element or the transistor is transferred to another substrate by using a separation layer as described above, the light-emitting element or the transistor can be formed over a substrate having low heat resistance or a flexible substrate over which the light-emitting element or the transistor is directly formed with difficulty. Examples of the above separation layer include a stack including inorganic films, e.g., a tungsten film and a silicon oxide film, and an organic resin film of polyimide or the like formed over a substrate. Examples of a substrate to which a transistor is transferred include, in addition to the above-described substrates over which a transistor can be formed, a paper substrate, a cellophane substrate, an aramid film substrate, a polyimide film substrate, a stone substrate, a wood substrate, a cloth substrate (including a natural fiber (e.g., silk, cotton, or hemp), a synthetic fiber (e.g., nylon, polyurethane, or polyester), a regenerated fiber (e.g., acetate, cupra, rayon, or regenerated polyester), or the like), a leather substrate, and a rubber substrate. With the use of any of these substrates, an increase in durability or heat resistance and a reduction in weight or thickness can be achieved.

Note that the structure described in this embodiment can be used as appropriate in combination with any of the structures described in the other embodiments.

Embodiment 2

In this embodiment, an organic compound represented by General Formula (G1) will be described in detail.

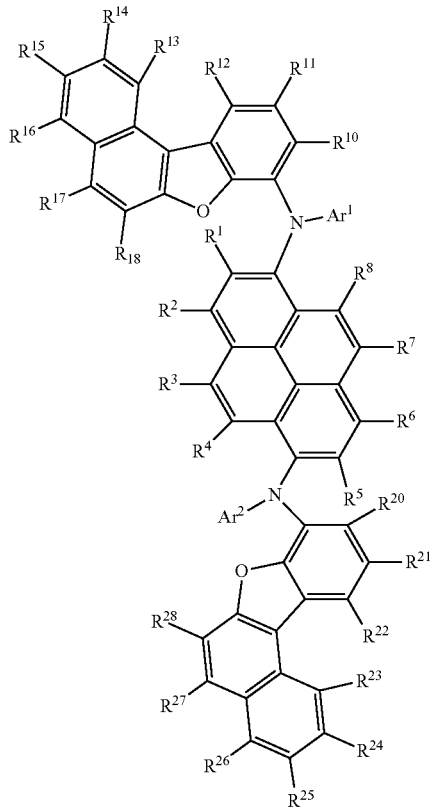

(G1)

In General Formula (G1), each of Ar$^1$ and Ar$^2$ independently represents a substituted or unsubstituted aryl group having 6 to 13 carbon atoms forming a ring; and each of R$^1$ to R$^8$, R$^{10}$ to R$^{18}$, and R$^{20}$ to R$^{28}$ independently represents hydrogen, a substituted or unsubstituted alkyl group having 1 to 6 carbon atoms, a substituted or unsubstituted alkoxy group having 1 to 6 carbon atoms, a cyano group, halogen, a substituted or unsubstituted haloalkyl group having 1 to 6 carbon atoms, or a substituted or unsubstituted aryl group having 6 to 10 carbon atoms. In a substance represented by General Formula (G1), each of R$^{18}$ and R$^{28}$ is preferably a substituted or unsubstituted phenyl group, in which case the emission wavelength of the substance can be short. The substance in which R$^{18}$ and R$^{28}$ are substituted or unsubstituted phenyl groups is preferably used for a light-emitting element, in which case the light-emitting element has an emission spectrum with a narrow half-width, high emission efficiency, and high reliability. In order to prevent distortion of a stereostructure, R$^{18}$ and R$^2$ are further preferably unsubstituted phenyl groups. In the case where R$^{18}$ and R$^{28}$ are each a phenyl group having a substituent, the substituent is preferably an alkyl group having 1 to 6 carbon atoms or a phenyl group.

As the organic compound represented by General Formula (G1), an organic compound represented by General Formula (G2) is preferably used because an emission wavelength can be shorter.

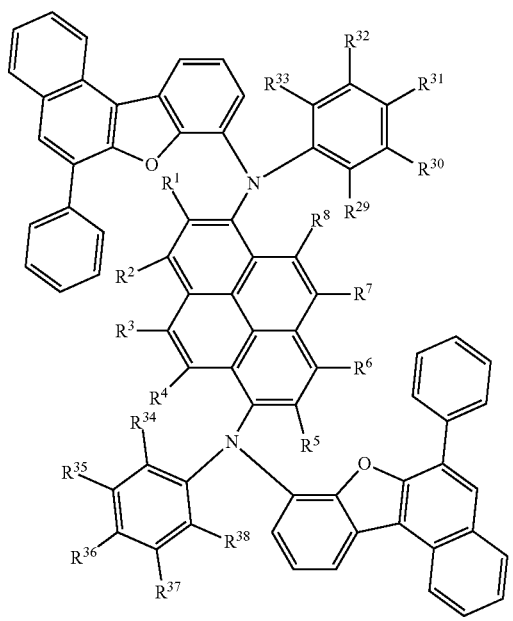

(G2)

In General Formula (G2), each of R$^1$ to R$^8$ and R$^{29}$ to R$^{38}$ independently represents hydrogen, a substituted or unsubstituted alkyl group having 1 to 6 carbon atoms, a substituted or unsubstituted alkoxy group having 1 to 6 carbon atoms, a cyano group, halogen, a substituted or unsubstituted haloalkyl group having 1 to 6 carbon atoms, or a substituted or unsubstituted aryl group having 6 to 10 carbon atoms.

Specific examples of the substituted or unsubstituted aryl group having 6 to 13 carbon atoms forming a ring in General Formula (G1) and the substituted or unsubstituted aryl group having 6 to 10 carbon atoms in General Formula (G2) include a phenyl group, a 1-naphthyl group, a 2-naphthyl group, an ortho-tolyl group, a meta-tolyl group, a para-tolyl group, an ortho-biphenyl group, a meta-biphenyl group, a para-biphenyl group, a 9,9-dimethyl-9H-fluoren-2-yl group, a 9,9-diphenyl-9H-fluoren-2-yl group, a 9H-fluoren-2-yl group, a para-tert-butylphenyl group, and a mesityl group.

Specific examples of the substituted or unsubstituted alkyl groups having 1 to 6 carbon atoms in General Formulae (G1) and (G2) include a methyl group, an ethyl group, an n-propyl group, an isopropyl group, a n-butyl group, a sec-butyl group, an isobutyl group, a tert-butyl group, an n-pentyl group, an isopentyl group, a sec-pentyl group, a tert-pentyl group, a neopentyl group, an n-hexyl group, an isohexyl group, a sec-hexyl group, a tert-hexyl group, a neo-hexyl group, a cyclohexyl group, a 3-methylpentyl group, a 2-methylpentyl group, a 2-ethylbutyl group, a 1,2-dimethylbutyl group, and a 2,3-dimethylbutyl group.

Specific examples of the substituted or unsubstituted alkoxy groups having 1 to 6 carbon atoms, the cyano group, the halogen, and the substituted or unsubstituted haloalkyl group having 1 to 6 carbon atoms in General Formulae (G1) and (G2) include a methoxy group, an ethoxy group, an n-propoxy group, an isopropoxy group, an n-butoxy group, a sec-butoxy group, an isobutoxy group, a tert-butoxy group, an n-pentyloxy group, an isopentyloxy group, a sec-pentyloxy group, a tert-pentyloxy group, a neo-pentyloxy group, an n-hexyloxy group, an isohexyloxy group, a sec-hexyloxy group, a tert-hexyloxy group, a neo-hexyloxy group, a cyclohexyloxy group, a 3-methylpentyloxy group, a 2-methylpentyloxy group, a 2-ethylbutoxy group, a 1,2-dimethylbutoxy group, a 2,3-dimethylbutoxy group, a cyano group, fluorine, chlorine, bromine, iodine, and a trifluoromethyl group.

In the organic compound, benzonaphthofuranylamine is bonded to each of the 1-position and the 6-position of a pyrene skeleton, and each of nitrogen atoms in benzonaphthofuranylamine is independently bonded to the 6-position or the 8-position of a benzo[b]naphtho[1,2-d]furanyl group. The structure in which benzonaphthofuranylamine is bonded to each of the 1-position and the 6-position of the pyrene skeleton enables the effective conjugation length from the pyrene skeleton to benzonaphthofuranylamine to be increased. Consequently, the emission peak wavelength can be shifted to the long wavelength side in comparison with that in the case of monocyclic pyrene. Furthermore, with this structure, a molecular structure is stabilized by a benzonaphthofuranyl group; thus, reliability is expected to be improved. Since the 6-position or the 8-position of the benzo[b]naphtho[1,2-d]furanyl group is bonded to an amine skeleton, the color purity of blue can be further increased.

In the case where the 8-position of the benzo[b]naphtho[1,2-d]furanyl group is bonded to the amine skeleton, light emission with a shorter wavelength can be obtained than in the case where the 6-position of the benzo[b]naphtho[1,2-d]furanyl group is bonded to the amine skeleton. This is because the effective conjunction length is shorter in the case where the 8-position of the benzo[b]naphtho[1,2-d]furanyl group is bonded to the amine skeleton. When the 6-position of the benzo[b]naphtho[1,2-d]furanyl group has an aryl group and the 8-position of the benzo[b]naphtho[1,2-d]furanyl group is bonded to the amine skeleton, the color purity of blue can be increased by steric hindrance of the aryl group. Furthermore, intermolecular interaction can be reduced in this structure; thus, high color purity can be kept even when the concentration of the organic compound is high.

With the use of the above organic compound as a light-emitting substance in a light-emitting element of one embodiment of the present invention, driving voltage for obtaining desired luminance can be reduced. Furthermore, a highly reliable light-emitting element can be obtained.

Specific examples of the above organic compounds (General Formulae (G1) and (G2)) that can be used in a light-emitting element of one embodiment of the present invention are shown (Structural Formulae (100) to (133)). Note that the present invention is not limited thereto.

(100)
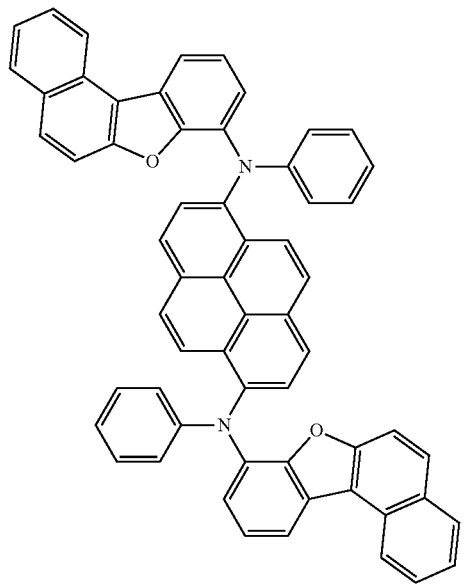

(101)
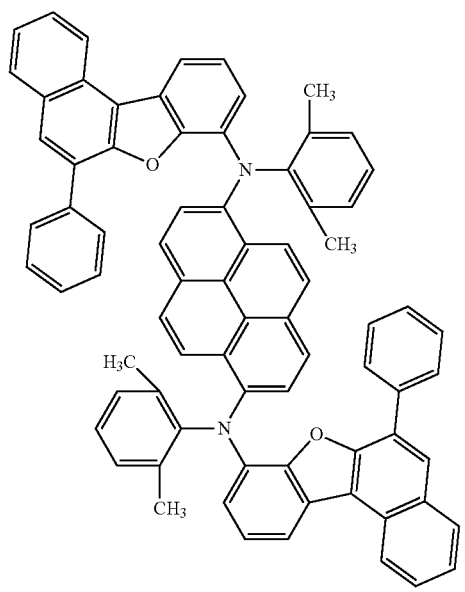

(102)
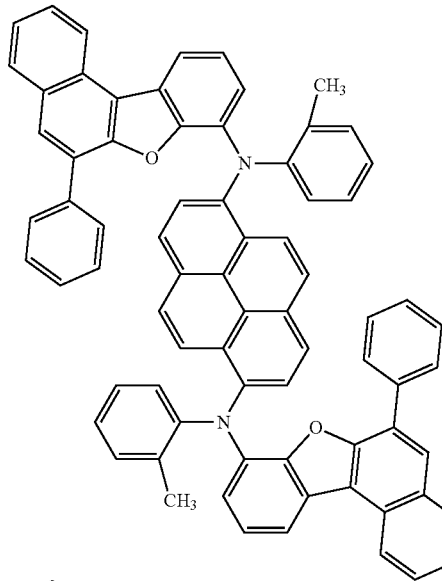

(103)
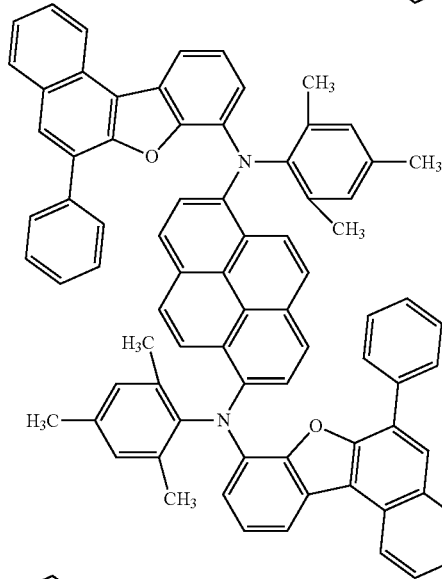

(104)
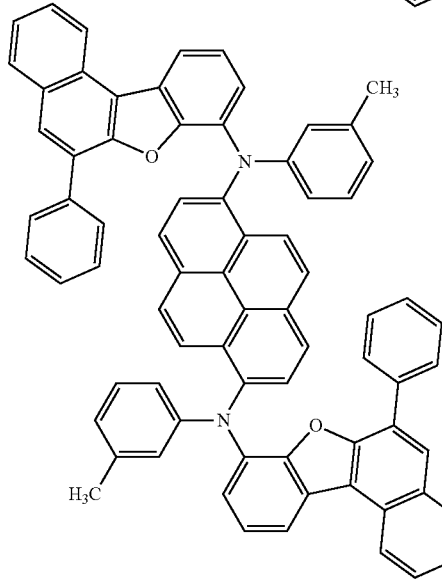

(105)
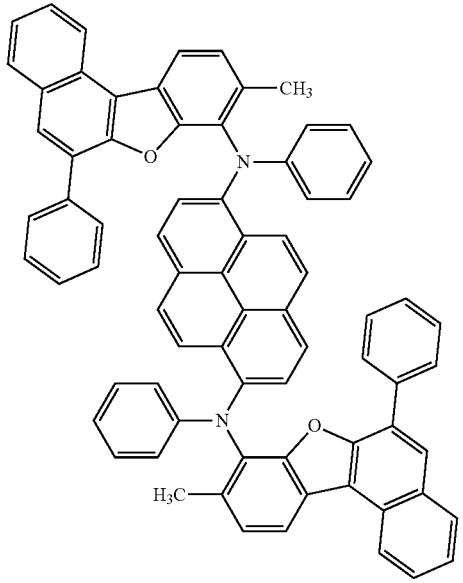
(106)
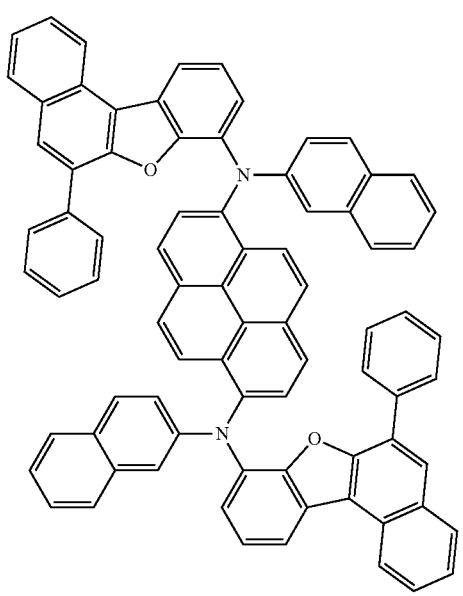
(107)
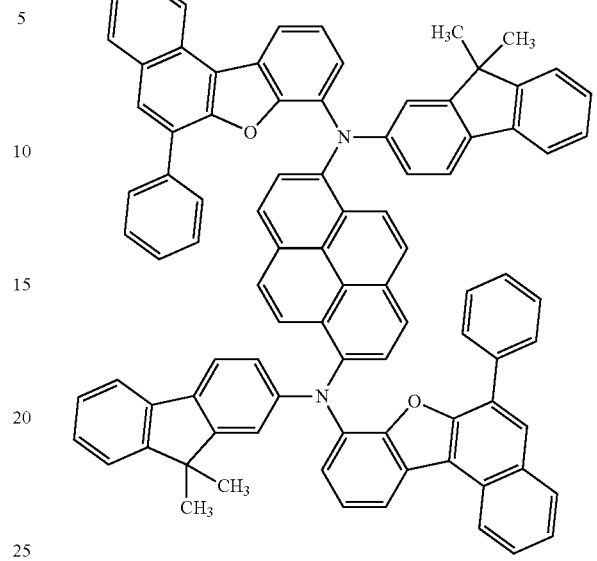
(108)
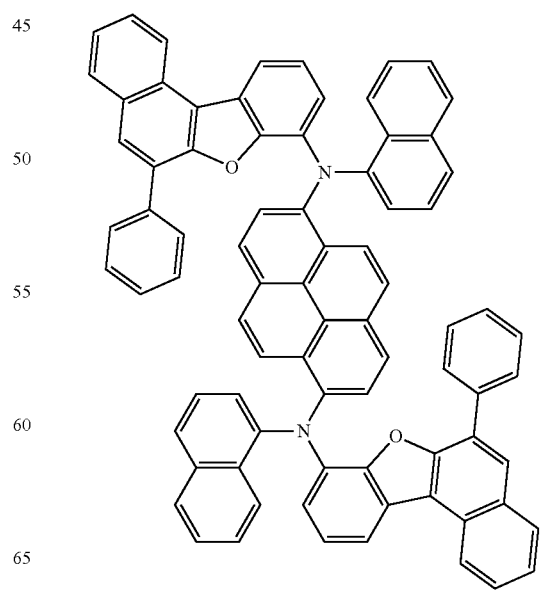

-continued
(109)
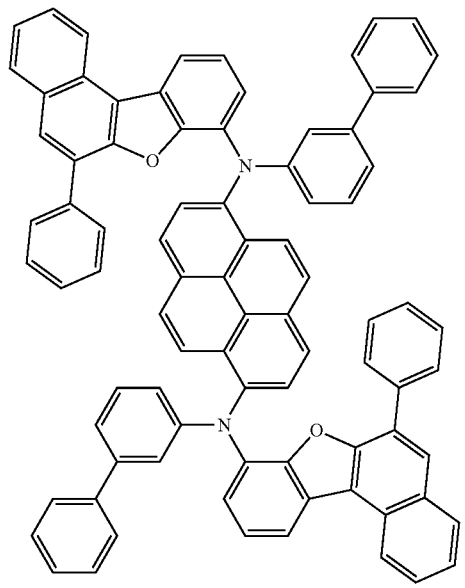
(110)
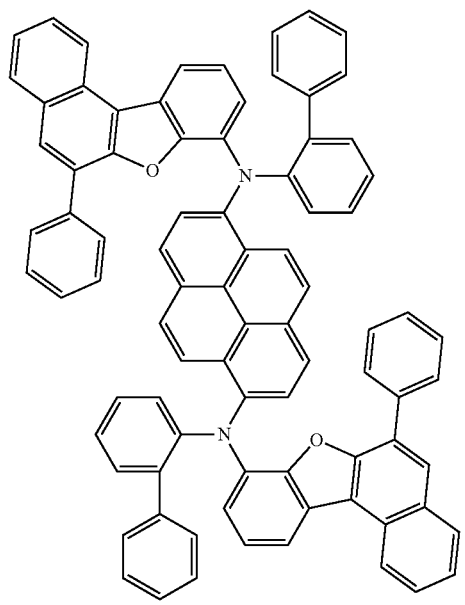
(111)
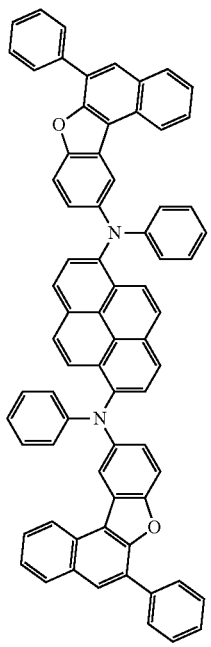
(112)
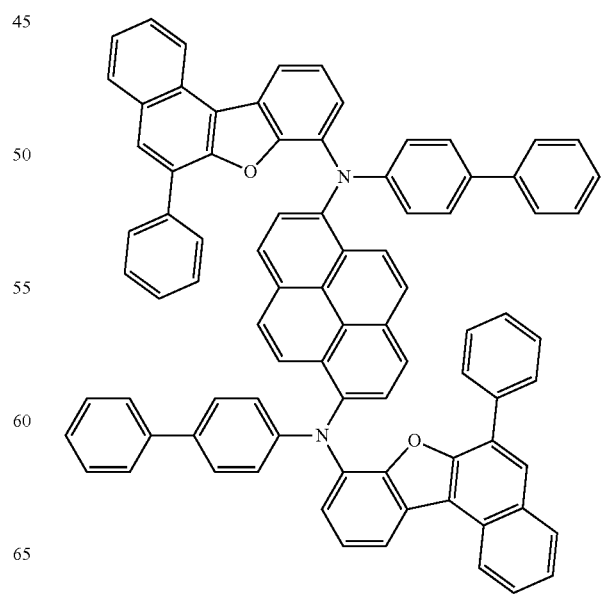

(113)
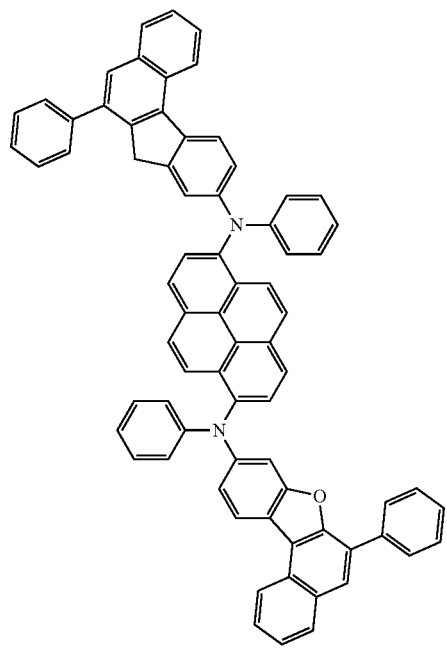
(114)
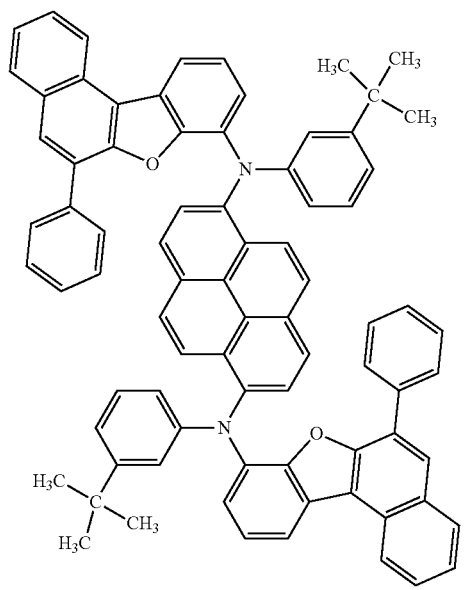
(115)
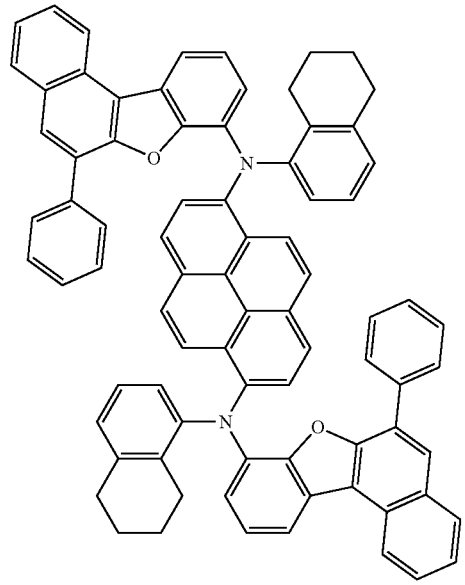
(116)
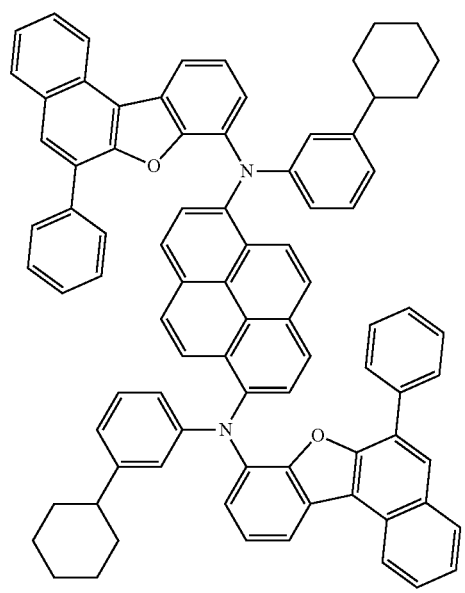

-continued
(117)
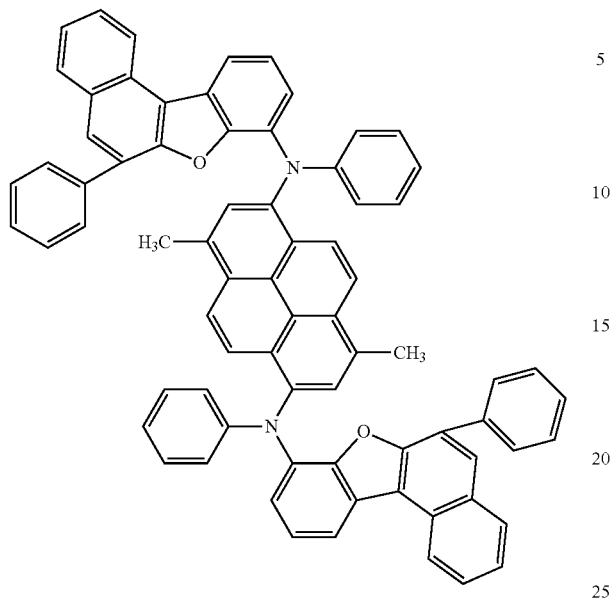
(118)
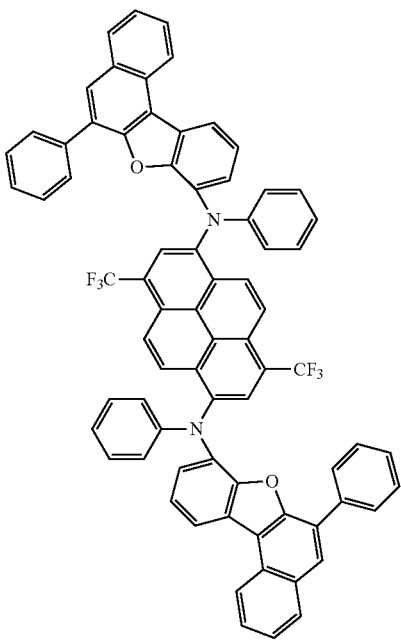
(119)
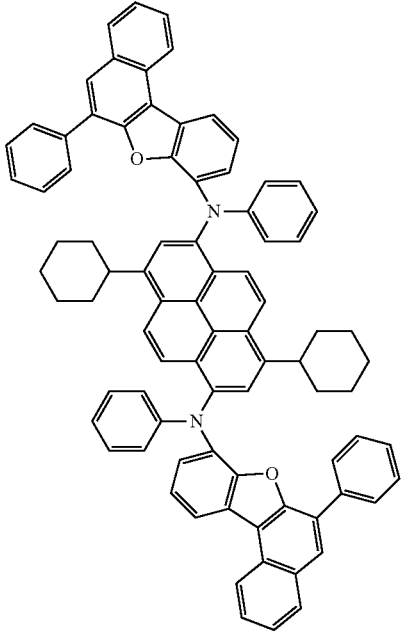
(120)
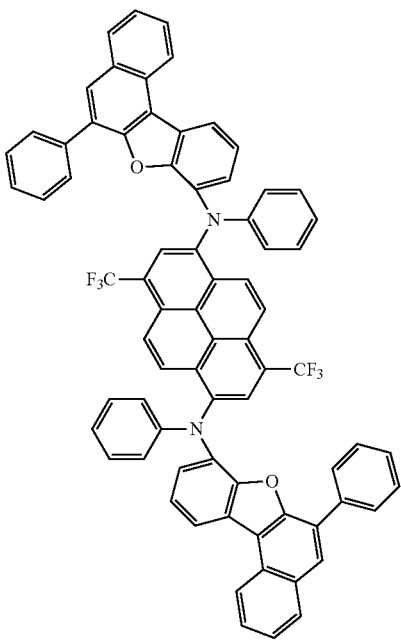

(121)
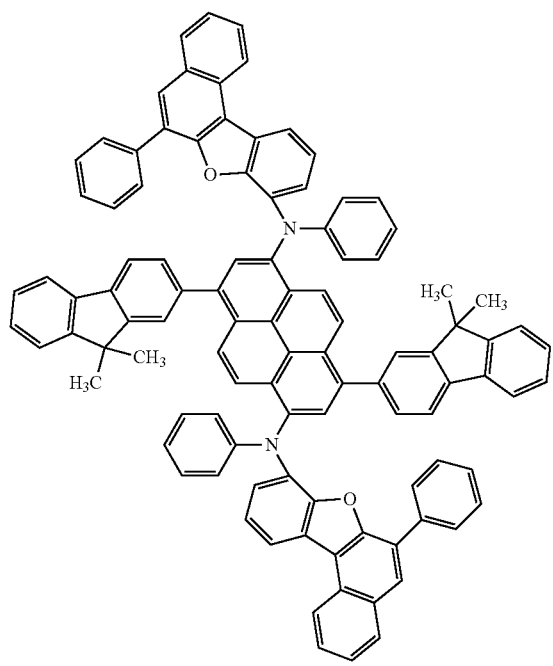
(123)
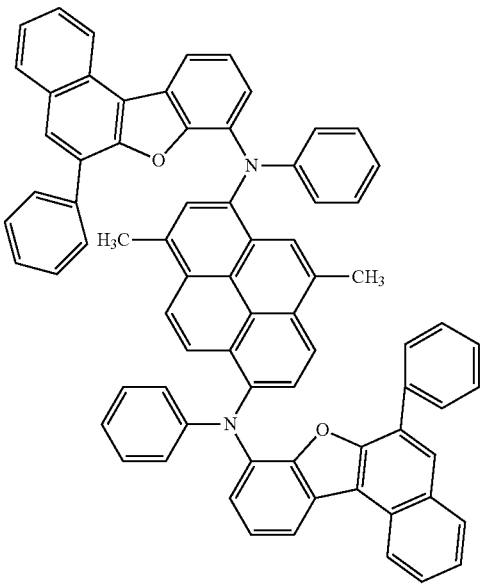
(122)
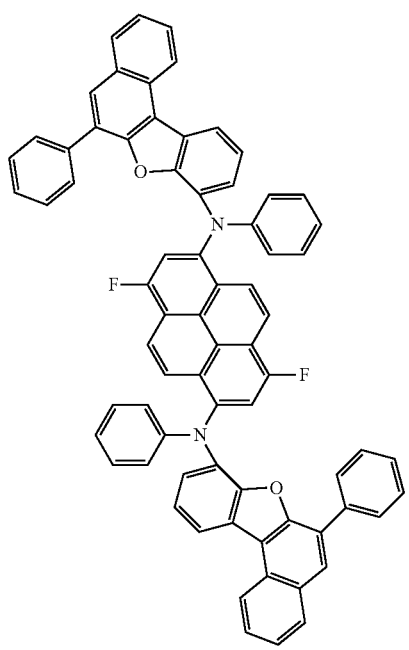
(124)
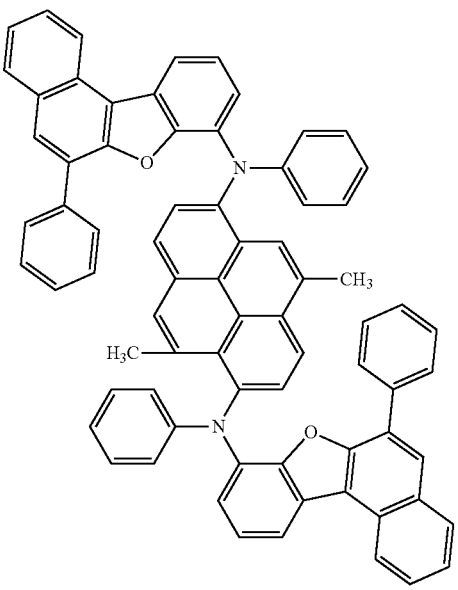

(125)
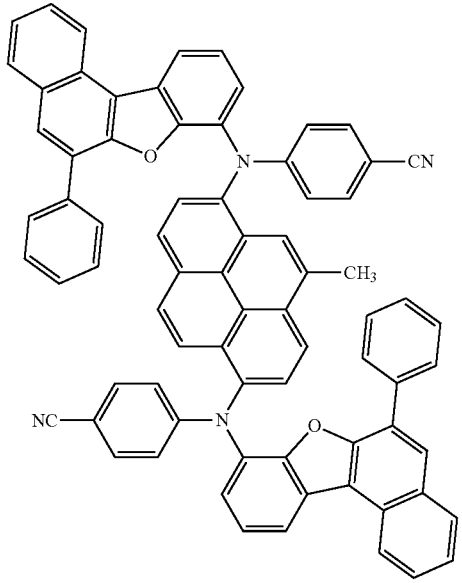
(127)
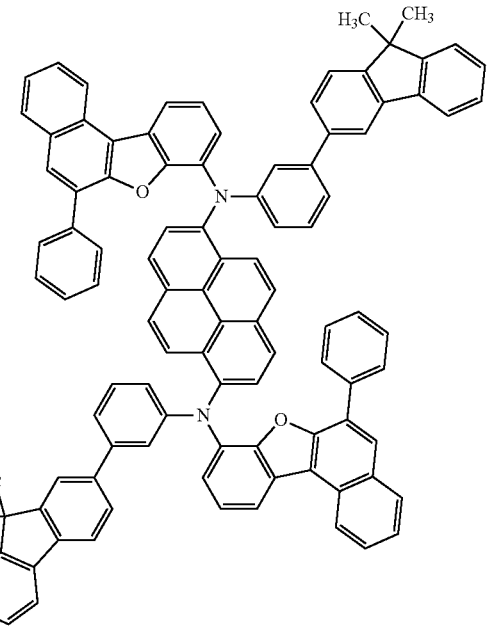
(126)
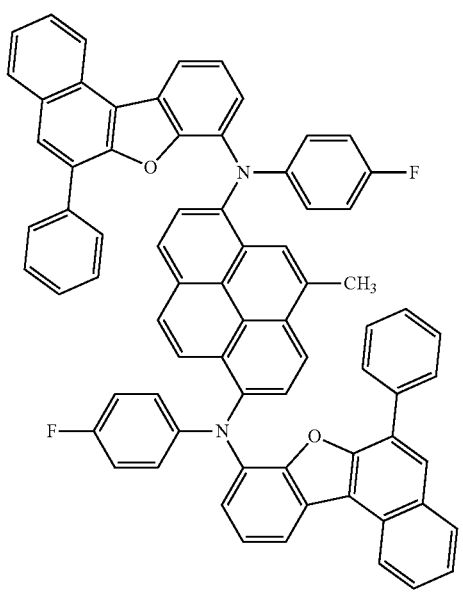
(128)
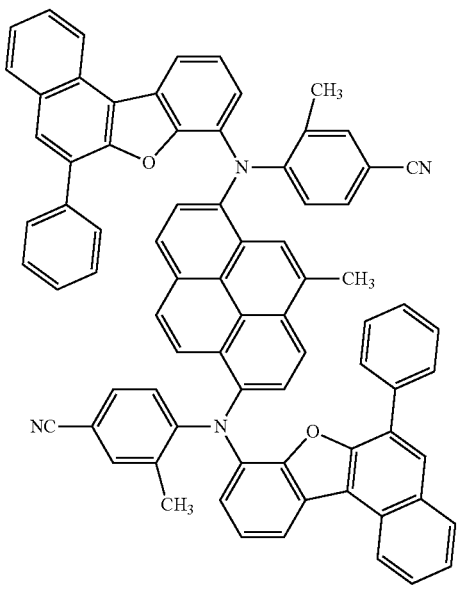

(129)
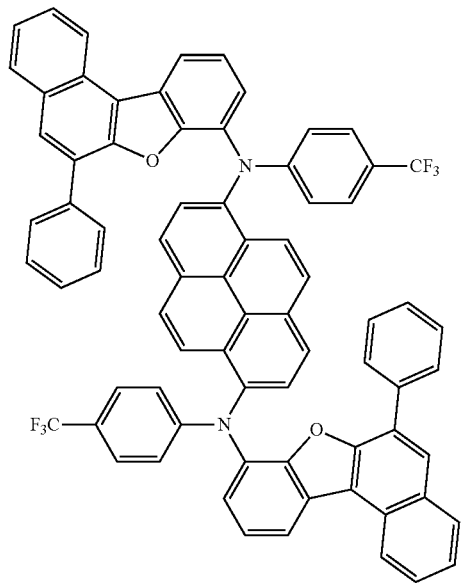
(130)
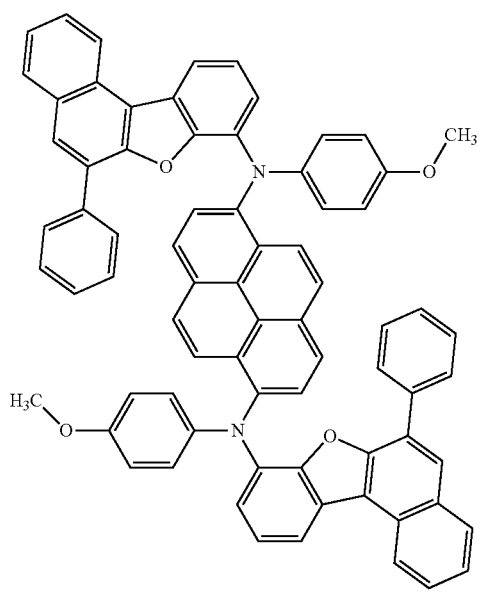
(131)
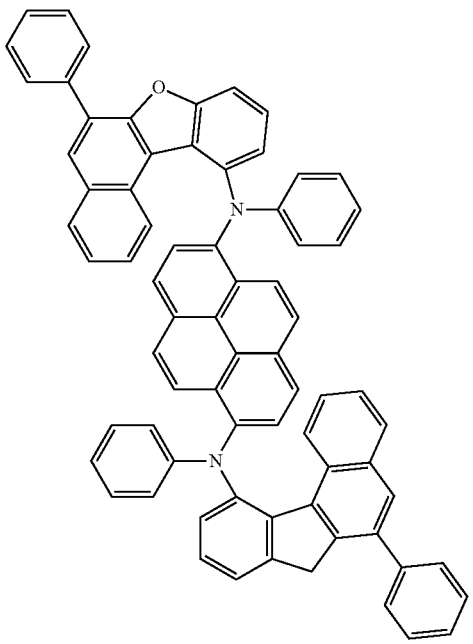
(132)
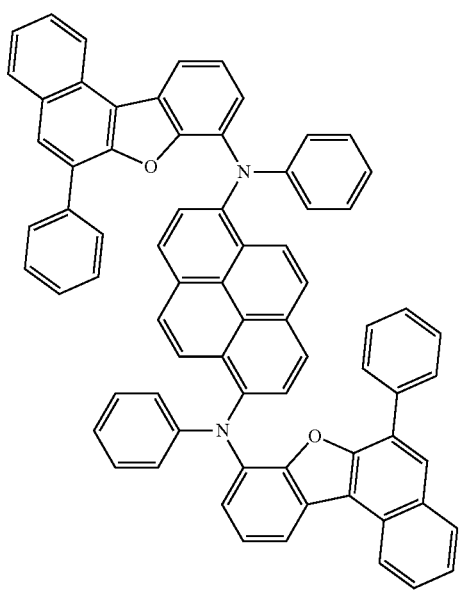

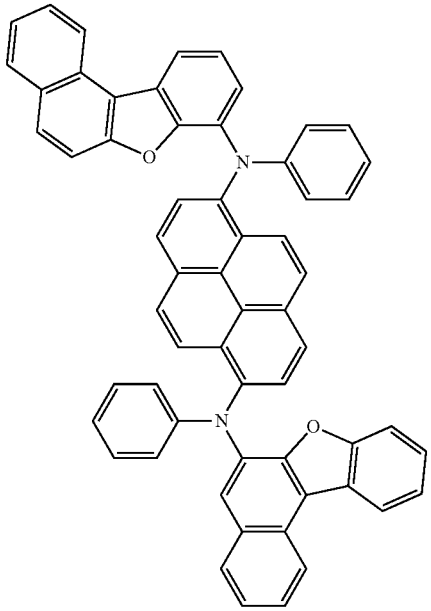

(133)

The above organic compound emits blue light with high color purity. Blue light emission having the chromaticity coordinates defined by the national television standards committee (NTSC), i.e., (x, y)=(0.14, 0.08) or near that or light emission of blue deeper than that can be obtained. Therefore, with the use of such an organic compound for a light-emitting element, the driving voltage of the light-emitting element can be low and the reliability thereof can be high. Furthermore, with the use of such a light-emitting element, the power consumption of a light-emitting device, an electronic device, and a lighting device of embodiments of the present invention can be reduced, and the lifetime thereof can be prolonged.

Note that the structure described in this embodiment can be used as appropriate in combination with any of the structures described in the other embodiments.

Embodiment 3

In this embodiment, one embodiment of a light-emitting device in which the light-emitting element described in Embodiment 1 is combined with a coloring layer (color filter or the like) will be described. In this embodiment, the structure of a pixel portion of the light-emitting device will be described with reference to FIG. 5.

Figure 5:
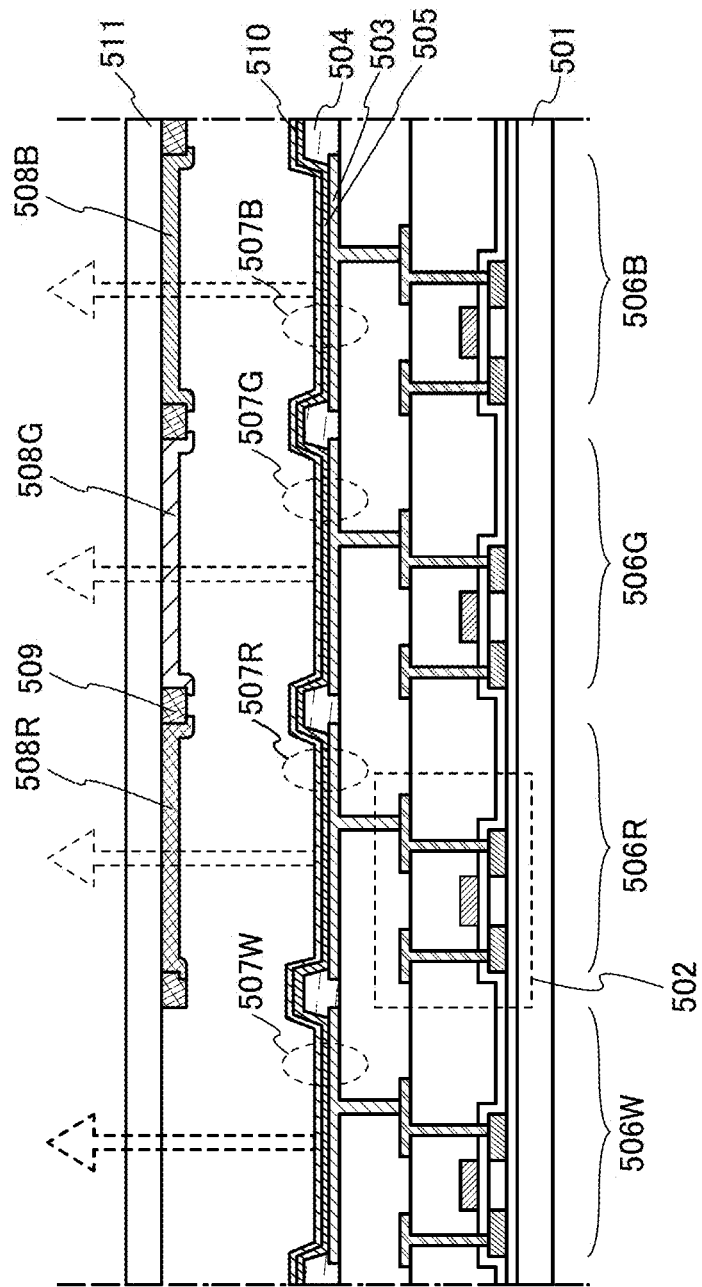
FIG. 5 illustrates a light-emitting device.

In FIG. 5, a plurality of FETs 502 is formed over a substrate 501. Each of the FETs 502 is electrically connected to a light-emitting element (507R, 507G, 507B, or 507W). Specifically, each of the FETs 502 is electrically connected to a first electrode 503 that is a pixel electrode of the light-emitting element. A partition 504 is provided so as to cover edge portions of adjacent first electrodes 503.

Note that the first electrode 503 in this embodiment serves as a reflective electrode. An EL layer 505 is formed over the first electrode 503, and a second electrode 510 is formed over the EL layer 505. The EL layer 505 includes a plurality of light-emitting layers each emitting monochromatic light. The second electrode 510 serves as a semi-transmissive and semi-reflective electrode.

The light-emitting elements (507R, 507G, 507B, and 507W) emit light with different colors. Specifically, the light-emitting element 507R is optically adjusted to emit red light, and in a region indicated by 506R, red light is emitted through a coloring layer 508R in the direction indicated by an arrow. The light-emitting element 507G is optically adjusted to emit green light, and in a region indicated by 506G, green light is emitted through a coloring layer 508G in the direction indicated by an arrow. The light-emitting element 507B is optically adjusted to emit blue light, and in a region indicated by 506B, blue light is emitted through a coloring layer 508B in the direction indicated by an arrow. The light-emitting element 507W is optically adjusted to emit white light, and in a region indicated by 506W, white light is emitted not through a coloring layer in the direction indicated by an arrow.

As illustrated in FIG. 5, the coloring layers (508R, 508G, and 508B) are provided on a transparent sealing substrate 511 that is provided above the substrate 501 over which the light-emitting elements (507R, 507G, 507B, and 507W) are formed. The coloring layers (508R, 508G, and 508B) are provided so as to overlap with the respective light-emitting elements (507R, 507G, and 507B) which exhibit different emission colors.

A black layer (black matrix) 509 is provided to cover edge portions of adjacent coloring layers (508R, 508G, and 508B). Note that the coloring layers (508R, 508G, and 508B) and the black layer 509 may be covered with an overcoat layer that is formed using a transparent material.

The above light-emitting device has a structure in which light is extracted from the sealing substrate 511 side (a top emission structure), but may have a structure in which light is extracted from the substrate 501 side where the FETs are formed (a bottom emission structure). Note that in the light-emitting device having a top emission structure described in this embodiment, a light-shielding substrate or a light-transmitting substrate can be used as the substrate 501, whereas in a light-emitting device having a bottom emission structure, a light-transmitting substrate needs to be used as the substrate 501.

Figure 10:
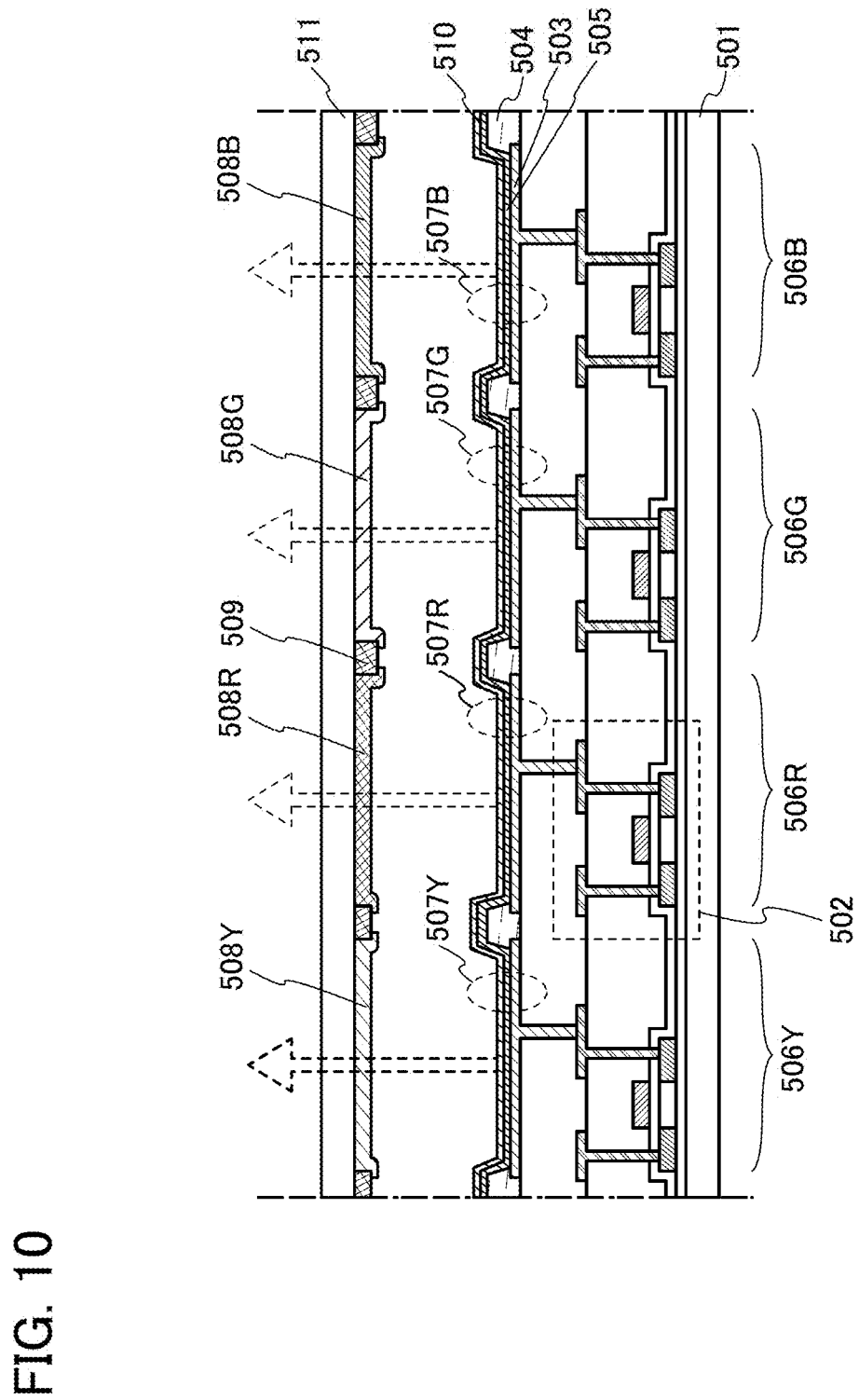
FIG. 10 illustrates a light-emitting device.

A structure illustrated in FIG. 10 can be employed as well as the above structure. The structure of the light-emitting elements (507R, 507G, 507B, and 507Y) electrically connected to the FETs 502 over the substrate 501 in FIG. 10 is partly different from that in FIG. 5. Blue emission can be obtained with the use of the fluorescent substance described in Embodiment 1 for the light-emitting layer 106a in the EL layer in Embodiment 1. Furthermore, yellow emission can be obtained from the light-emitting layer 106b in the EL layer in Embodiment 1.

In this case, the light-emitting elements (507R, 507G, 507B, and 507Y) emit light of different colors. Specifically, the light-emitting element 507R is optically adjusted to emit red light, and in a region indicated by 506R, red light is emitted through the coloring layer 508R in the direction indicated by an arrow. The light-emitting element 507G is optically adjusted to emit green light, and in a region indicated by 506G, green light is emitted through the coloring layer 508G in the direction indicated by an arrow. The light-emitting element 507B is optically adjusted to emit blue light, and in a region indicated by 506B, blue light is emitted through the coloring layer 508B in the direction indicated by an arrow. The light-emitting element 507Y is optically adjusted to emit yellow light, and in a region indicated by 506Y, yellow light is emitted through a coloring layer 508Y in the direction indicated by an arrow.

As illustrated in FIG. 10, the coloring layers (508R, 508G, 508B, and 508Y) are provided on the transparent sealing substrate 511 that is provided above the substrate 501 over which the light-emitting elements (507R, 507G, 507B, and 507Y) are formed. The coloring layers (508R, 508G, 508B, and 508Y) are provided so as to overlap with the respective light-emitting elements (507R, 507G, 507B, and 507Y) which exhibit different emission colors.

In the light-emitting device of one embodiment of the present invention, blue light emitted from the light-emitting element 507B and extracted through the coloring layer 508B to the outside of the light-emitting device preferably has chromaticity coordinates of (x, y)=(greater than or equal to 0.13 and less than or equal to 0.17, greater than or equal to 0.03 and less than or equal to 0.08) on the xy chromaticity diagram so that deep blue emission can be obtained. Preferably, blue light emitted from the light-emitting element 507B and extracted through the coloring layer 508B to the outside of the light-emitting device has a y-coordinate greater than or equal to 0.03 and less than or equal to 0.07.

With the use of blue emission having such chromaticity, the luminance of blue emission needed for obtaining white emission can be reduced. Since the amount of current consumed by the blue light-emitting element for obtaining predetermined white emission is sufficiently larger than that consumed by the light-emitting element of the other colors, an effect of reducing the amount of current due to a reduction in the luminance of blue emission needed for obtaining white emission is considerable.

Although current efficiency is generally decreased owing to desired chromaticity of blue emission, the effect of reducing the luminance of blue emission needed for obtaining white emission is considerable. As a result, the amount of current flowing in the blue light-emitting element for obtaining predetermined white emission is significantly reduced, and accordingly power consumption of the whole light-emitting device is reduced.

When the chromaticity of blue emission corresponds to deep blue as described above, the color of emission obtained by synthesis of the blue emission and yellow emission changes and a third emission color needed for obtaining predetermined white emission changes in some cases. For example, in the case where blue emission has the chromaticity coordinates defined by NTSC, i.e., (x, y)=(0.14, 0.08) or near that and yellow emission has chromaticity coordinates of (x, y)=(0.45, 0.54) or near that, a red emission component is further needed for obtaining white emission having chromaticity at approximately D65 in addition to light emission obtained by synthesis of the blue emission and the yellow emission. On the other hand, in the case where blue emission has the chromaticity coordinates defined by NTSC or near that and yellow emission has chromaticity coordinates of (x, y)=(0.46, 0.53) or chromaticity coordinates of redder emission (that is, x is larger than 0.46 and y is smaller than 0.53), white emission having chromaticity at approximately D65 can be obtained by addition of a green emission component to light emission obtained by synthesis of the blue emission and the yellow emission. However, in the case where yellow emission has chromaticity coordinates of redder emission (that is, x is larger than 0.46 and y is smaller than 0.53), the current efficiency of yellow pixels is reduced owing to a reduction in luminosity factor. That is, an effect of a reduction in power consumption is reduced accordingly.

In this manner, the third emission color needed for obtaining white emission having chromaticity at approximately D65 depends on the colors of blue emission and yellow emission. The current efficiency of green emission is generally higher than that of red emission, and thus is advantageous. However, in the case where yellow emission has chromaticity coordinates of redder emission (that is, x is larger than 0.46 and y is smaller than 0.53) as described above, the current efficiency of yellow pixels is reduced owing to a reduction in the luminosity factor of yellow emission. An influence of a reduction in the current efficiency of yellow emission with a high luminosity factor is considerable, and thus it is preferable that the chromaticity of yellow emission be not near the chromaticity of red emission.

In the case where deep blue emission having chromaticity coordinates of (x, y)=(greater than or equal to 0.13 and less than or equal to 0.17, greater than or equal to 0.03 and less than or equal to 0.08) is used, the chromaticity of yellow with a high luminosity factor is kept (that is, the chromaticity which is not too near the chromaticity of red emission) and white emission having chromaticity at approximately D65 can be obtained with the use of green emission as third emission in addition to blue emission and yellow emission. With such a structure, the current efficiency can be kept high because yellow emission has a high luminosity factor. Furthermore, the luminance needed for green emission in this structure is lower than that in the case where red emission is used as the third emission. Since the luminosity factor of green emission is higher than that of red emission, and the current efficiency of a green light-emitting element is generally higher than that of a red light-emitting element, the amount of current needed for obtaining the third emission is significantly reduced. As a result, driving voltage is reduced, and thus power consumption can be reduced. The chromaticity coordinates of the yellow emission at this time are preferably (x, y)=(greater than or equal to 0.44 and less than or equal to 0.46, greater than or equal to 0.53 and less than or equal to 0.55).

Although the luminance components of the blue light-emitting element and the light-emitting element that exhibits the third emission for obtaining the predetermined white emission are reduced, they can be compensated for by increasing the luminance of the yellow light-emitting element. Since the luminosity factor of the yellow emission is significantly high, the current efficiency of the yellow light-emitting element is significantly high. An increase in power consumption due to the increase in luminance needed for obtaining the yellow emission can be compensated for by a reduction in power consumption due to a reduction in the luminance needed for the blue light-emitting element and the light-emitting element that exhibits the third emission. As a result, a reduction in power consumption can be achieved.

In order that deep blue emission having chromaticity coordinates of (x, y)=(greater than or equal to 0.13 and less than or equal to 0.17, greater than or equal to 0.03 and less than or equal to 0.08), preferably (greater than or equal to 0.13 and less than or equal to 0.17, greater than or equal to 0.03 and less than or equal to 0.07) on the xy chromaticity diagram can be obtained, the peak wavelength of an emission spectrum of a fluorescent material contained in a first light-emitting element in a toluene solution of the fluorescent material is set greater than or equal to 440 nm and less than or equal to 460 nm, preferably greater than or equal to 440 nm and less than or equal to 455 nm. The chromaticity of the blue light-emitting element can be adjusted with the use of a color filter or the like; however, only a small amount of light having the above wavelength is filtered out by a color filter, and light emission from the fluorescent material can be efficiently utilized. Thus, the half-width of the emission spectrum of the fluorescent material in the toluene solution is preferably greater than or equal to 20 nm and less than or equal to 50 nm.

With the use of blue emission having such chromaticity, power consumption for obtaining white emission having chromaticity coordinates of (x, y)=(0.313, 0.329) on the xy chromaticity diagram at approximately D65 can be reduced. Specifically, in the case where white emission having chromaticity coordinates of (x, y)=(0.313, 0.329) on the xy chromaticity diagram is obtained with a luminance of 300 cd/m$^2$, the power consumption of the light-emitting device except the power consumption of the driving FETs can be higher than or equal to 1 mW/cm$^2$ and lower than or equal to 7 mW/cm$^2$, and the power consumption of the light-emitting device including the power consumption of the driving FETs (the power consumption calculated from the product of current consumption and a voltage between an anode and a cathode) can be higher than or equal to 2 mW/cm$^2$ and lower than or equal to 15 mW/cm$^2$.

With the above structure, light-emitting elements that exhibit a plurality of emission colors (red, blue, green, and yellow) can be provided, and in addition, a light-emitting device that is capable of emitting white light with high efficiency by combination of these emission colors can be provided.

For the light-emitting device of one embodiment of the present invention, a variety of substrates can be used. There is no particular limitation on the type of substrate. Examples of the substrate include a semiconductor substrate (e.g., a single crystal substrate or a silicon substrate), an SOI substrate, a glass substrate, a quartz substrate, a plastic substrate, a metal substrate, a stainless steel substrate, a substrate including stainless steel foil, a tungsten substrate, a substrate including tungsten foil, a flexible substrate, an attachment film, paper including a fibrous material, and a base material film. Examples of a glass substrate include a barium borosilicate glass substrate, an aluminoborosilicate glass substrate, and a soda lime glass substrate. Examples of a flexible substrate, an attachment film, and a base material film include plastics typified by polyethylene terephthalate (PET), polyethylene naphthalate (PEN), polyether sulfone (PES), and polytetrafluoroethylene (PTFE); acrylic; polypropylene; polyester; polyvinyl fluoride; polyvinyl chloride; polyamide; polyimide; aramid; epoxy; an inorganic vapor deposition film; and paper.

The use of a semiconductor substrate, a single crystal substrate, an SOI substrate, or the like for a transistor enables the manufacture of small-sized transistors with a small variation in characteristics, size, shape, or the like and with high current capability. A circuit using such transistors achieves lower power consumption of the circuit or higher integration of the circuit.

A semiconductor device such as a transistor may be formed after a separation layer is provided over the substrate. The separation layer can be used when part or the whole of a semiconductor device formed over the separation layer is separated from the substrate and transferred onto another substrate. In such a case, the transistor can be transferred to a substrate having low heat resistance or a flexible substrate as well. Examples of the above separation layer include a stack including inorganic films, e.g., a tungsten film and a silicon oxide film, and an organic resin film of polyimide or the like formed over a substrate.

In other words, after the transistor or the light-emitting element is formed using one substrate, the transistor or the light-emitting element may be transferred to another substrate. Examples of a substrate to which the transistor or the light-emitting element is transferred include, in addition to the above-described substrates over which a transistor can be formed, a paper substrate, a cellophane substrate, an aramid film substrate, a polyimide film substrate, a stone substrate, a wood substrate, a cloth substrate (including a natural fiber (e.g., silk, cotton, or hemp), a synthetic fiber (e.g., nylon, polyurethane, or polyester), a regenerated fiber (e.g., acetate, cupra, rayon, or regenerated polyester), or the like), a leather substrate, and a rubber substrate. When such a substrate is used, a transistor with excellent properties or low power consumption can be formed, a device with high durability and high heat resistance can be provided, or a reduction in weight or thickness can be achieved. Note that in the case where a flexible light-emitting device is manufactured, a transistor or a light-emitting element may be directly formed over a flexible substrate.

Note that the structure described in this embodiment can be used as appropriate in combination with any of the structures described in the other embodiments.

Embodiment 4

In this embodiment, a light-emitting device including a light-emitting element of one embodiment of the present invention will be described.

The light-emitting device may be either a passive matrix light-emitting device or an active matrix light-emitting device. Note that any of the light-emitting elements described in the other embodiments can be used for the light-emitting device described in this embodiment.

In this embodiment, an active matrix light-emitting device will be described with reference to FIGS. 6A and 6B.

Figure 6A:
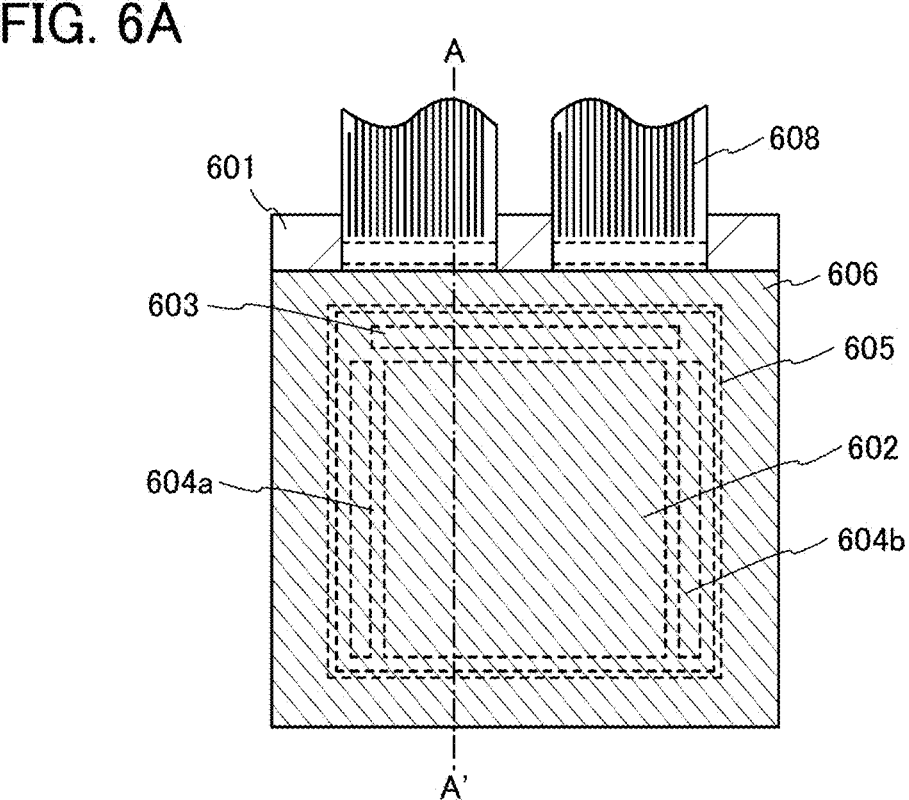
FIGS. 6A and 6B illustrate a light-emitting device.
Figure 6B:
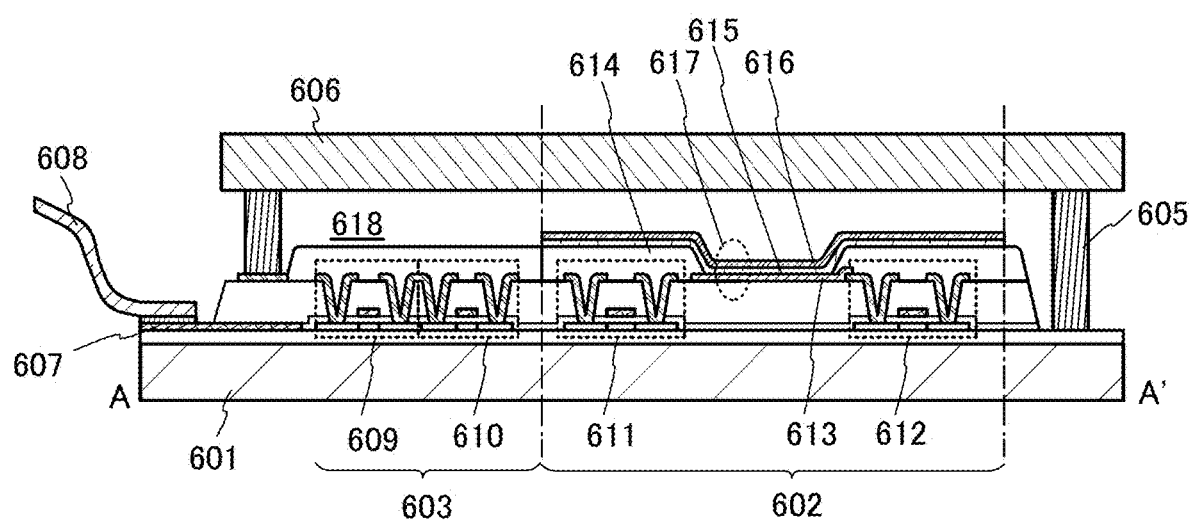

Note that FIG. 6A is a top view illustrating a light-emitting device and FIG. 6B is a cross-sectional view taken along the chain line A-A' in FIG. 6A. In the active matrix light-emitting device of this embodiment, a pixel portion 602, a driver circuit portion (a source line driver circuit) 603, and driver circuit portions (gate line driver circuits) 604*a* and 604*b* are provided over an element substrate 601. The pixel portion 602, the driver circuit portion 603, and the driver circuit portions 604*a* and 604*b* are sealed between the element substrate 601 and a sealing substrate 606 with a sealant 605.

In addition, a lead wiring 607 for connecting an external input terminal is provided over the element substrate 601. Through the external input terminal, a signal (e.g., a video signal, a clock signal, a start signal, or a reset signal) or a potential is transmitted from the outside to the driver circuit portion 603 and the driver circuit portions 604*a* and 604*b*. Here, a flexible printed circuit (FPC) 608 is provided as an example of the external input terminal. Although only the FPC is illustrated here, the FPC may be provided with a printed wiring board (PWB). The light-emitting device in this specification includes, in its category, not only the light-emitting device itself but also the light-emitting device provided with the FPC or the PWB.

Next, a cross-sectional structure will be described with reference to FIG. 6B. The driver circuit portion and the pixel portion are formed over the element substrate 601; the driver circuit portion 603 that is the source line driver circuit and the pixel portion 602 are illustrated here.

As an example of the driver circuit portion 603, an FET 609 and an FET 610 are combined. Note that the driver circuit portion 603 may be formed with a circuit including transistors having the same conductivity type (either an n-channel transistor or a p-channel transistor) or a CMOS circuit including an n-channel transistor and a p-channel transistor. In this embodiment, the driver circuit is integrated with the substrate; however, the driver circuit is not necessarily formed over the substrate, and may be formed outside the substrate.

The pixel portion 602 includes a plurality of pixels each of which includes a switching FET 611, a current control FET 612, and a first electrode (anode) 613 that is electrically connected to a wiring (a source electrode or a drain electrode) of the current control FET 612. In this embodiment, the pixel portion 602 includes, but is not limited to, two FETs, the switching FET 611 and the current control FET 612. The pixel portion 602 may include, for example, three or more FETs and a capacitor in combination.

As the FETs 609, 610, 611, and 612, for example, a staggered transistor or an inverted staggered transistor can be used. Examples of a semiconductor material that can be used for the FETs 609, 610, 611, and 612 include Group 13 semiconductors (e.g., gallium), Group 14 semiconductors (e.g., silicon), compound semiconductors, oxide semiconductors, and organic semiconductors. In addition, there is no particular limitation on the crystallinity of the semiconductor material, and an amorphous semiconductor or a crystalline semiconductor can be used. In particular, an oxide semiconductor is preferably used for the FETs 609, 610, 611, and 612. Examples of the oxide semiconductor include an In—Ga oxide and an In-M-Zn oxide (M is Al, Ga, Y, Zr, La, Ce, or Nd). For example, an oxide semiconductor that has an energy gap of 2 eV or more, preferably 2.5 eV or more, further preferably 3 eV or more is used for the FETs 609, 610, 611, and 612, so that the off-state current of the transistors can be reduced.

An insulator 614 is formed to cover end portions of the first electrode 613. In this embodiment, the insulator 614 is formed using a positive photosensitive acrylic resin. The first electrode 613 is used as an anode in this embodiment.

The insulator 614 preferably has a curved surface with curvature at an upper end portion or a lower end portion thereof. This provides favorable coverage with a film to be formed over the insulator 614. The insulator 614 can be formed using, for example, either a negative photosensitive resin or a positive photosensitive resin. The material of the insulator 614 is not limited to an organic compound, and an inorganic compound such as silicon oxide, silicon oxynitride, or silicon nitride can also be used.

An EL layer 615 and a second electrode (cathode) 616 are formed over the first electrode (anode) 613. The EL layer 615 includes at least a light-emitting layer. In addition to the light-emitting layer, a hole-injection layer, a hole-transport layer, an electron-transport layer, an electron-injection layer, a charge-generation layer, and the like can be provided as appropriate in the EL layer 615.

A light-emitting element 617 is formed with a stack of the first electrode (anode) 613, the EL layer 615, and the second electrode (cathode) 616. For the first electrode (anode) 613, the EL layer 615, and the second electrode (cathode) 616, the materials described in Embodiment 1 can be used. Although not illustrated, the second electrode (cathode) 616 is electrically connected to the FPC 608 which is an external input terminal.

Although the cross-sectional view of FIG. 6B illustrates only one light-emitting element 617, a plurality of light-emitting elements are arranged in matrix in the pixel portion 602. Light-emitting elements which provide three kinds of light emission (R, G, and B) are selectively formed in the pixel portion 602, whereby a light-emitting device capable of full color display can be fabricated. Other than the light-emitting element which provides three kinds of light emission (R, G, and B), for example, a light-emitting element that emits white (W), yellow (Y), magenta (M), and cyan (C) light may be formed. When the above light-emitting element that provides several kinds of light emission is provided as well as a light-emitting element that provides three kinds of light emission (R, G, and B), for example, higher color purity, lower power consumption, or the like can be achieved. Alternatively, a light-emitting device capable of full color display may be provided by a combination with color filters. The light-emitting device may have an improved emission efficiency and a reduced power consumption by combination with quantum dots.

Furthermore, the sealing substrate 606 is attached to the element substrate 601 with the sealant 605, whereby a light-emitting element 617 is provided in a space 618 surrounded by the element substrate 601, the sealing substrate 606, and the sealant 605. Note that the space 618 may be filled with an inert gas (such as nitrogen or argon) or the sealant 605.

An epoxy-based resin or glass frit is preferably used for the sealant 605. The material preferably allows as little moisture and oxygen as possible to penetrate. As the sealing substrate 606, a substrate formed using any of the materials described in Embodiment 3, such as a glass substrate, a quartz substrate, or a plastic substrate formed of fiber-reinforced plastic (FRP), polyvinyl fluoride (PVF), polyester, acrylic, or the like, can be used. In the case where glass frit is used as the sealant, the element substrate 601 and the sealing substrate 606 are preferably glass substrates for high adhesion.

An active matrix light-emitting device can be obtained in the above manner.

Note that the structure described in this embodiment can be used as appropriate in combination with any of the structures described in the other embodiments.

Embodiment 5

In this embodiment, examples of a variety of electronic devices that are manufactured using a light-emitting device which is one embodiment of the present invention will be described with reference to FIGS. 7A, 7B, 7C, 7D, 7D'-1, and 7D'-2.

Examples of electronic devices including the light-emitting device include television devices (also referred to as TV or television receivers), monitors for computers and the like, cameras such as digital cameras and digital video cameras, digital photo frames, mobile phones (also referred to as cellular phones or portable telephone devices), portable game machines, portable information terminals, audio playback devices, and large game machines such as pachinko machines. Specific examples of the electronic devices are illustrated in FIGS. 7A, 7B, 7C, 7D, 7D'-1, and 7D'-2.

Figure 7A:
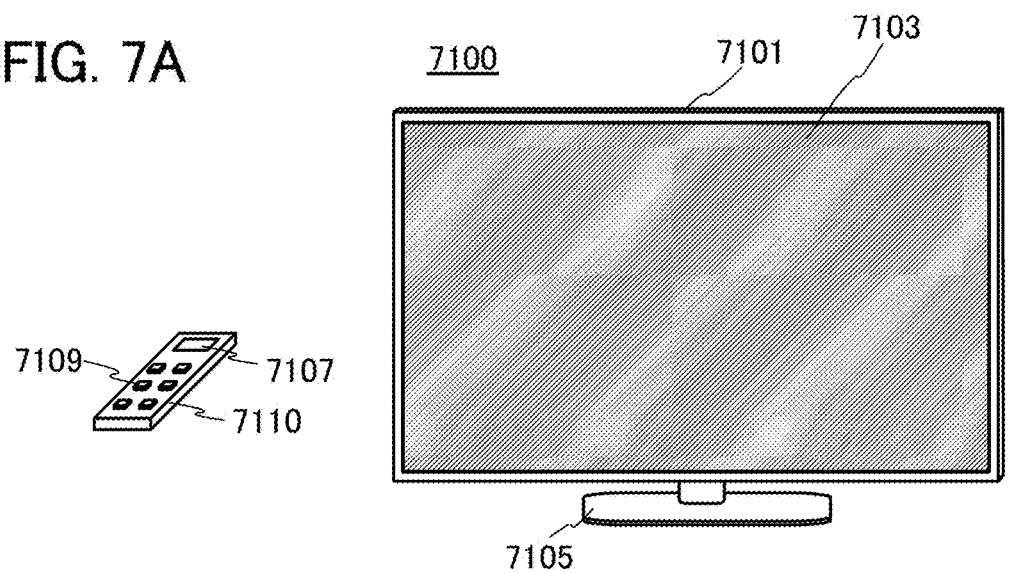
FIGS. 7A, 7B, 7C, 7D, 7D'-1, and 7D'-2 illustrate electronic devices.

FIG. 7A illustrates an example of a television device. In the television device 7100, a display portion 7103 is incorporated in a housing 7101. The display portion 7103 can display images and may be a touch panel (an input/output device) including a touch sensor (an input device). Note that the light-emitting device which is one embodiment of the present invention can be used for the display portion 7103. In addition, here, the housing 7101 is supported by a stand 7105.

The television device 7100 can be operated by an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television device 7100 is provided with a receiver, a modem, and the like. With the use of the receiver, general television broadcasts can be received. Moreover, when the television device is connected to a communication network with or without wires via the modem, one-way (from a sender to a receiver) or two-way (between a sender and a receiver or between receivers) information communication can be performed.

Figure 7B:
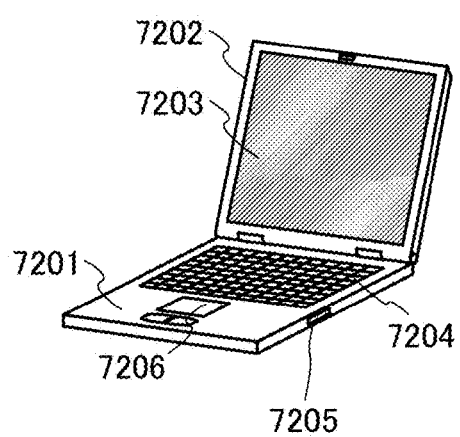

FIG. 7B illustrates a computer, which includes a main body 7201, a housing 7202, a display portion 7203, a keyboard 7204, an external connection port 7205, a pointing device 7206, and the like. Note that this computer can be manufactured using the light-emitting device which is one embodiment of the present invention for the display portion 7203. The display portion 7203 may be a touch panel (an input/output device) including a touch sensor (an input device).

Figure 7C:
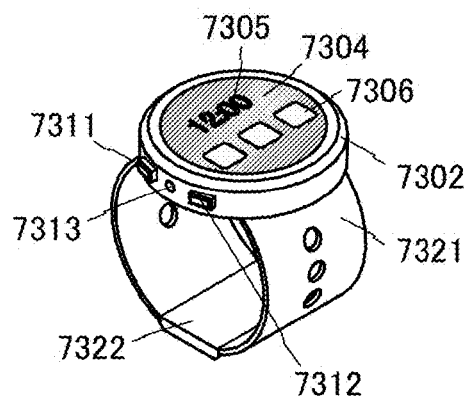

FIG. 7C illustrates a smart watch, which includes a housing 7302, a display panel 7304, operation buttons 7311 and 7312, a connection terminal 7313, a band 7321, a clasp 7322, and the like.

The display panel 7304 mounted in the housing 7302 serving as a bezel includes a non-rectangular display region. The display panel 7304 can display an icon 7305 indicating time, another icon 7306, and the like. The display panel 7304 may be a touch panel (an input/output device) including a touch sensor (an input device).

The smart watch illustrated in FIG. 7C can have a variety of functions, for example, a function of displaying a variety of information (e.g., a still image, a moving image, and a text image) on a display portion, a touch panel function, a function of displaying a calendar, date, time, and the like, a function of controlling processing with a variety of software (programs), a wireless communication function, a function of being connected to a variety of computer networks with a wireless communication function, a function of transmitting and receiving a variety of data with a wireless communication function, and a function of reading program or data stored in a recording medium and displaying the program or data on a display portion.

The housing 7302 can include a speaker, a sensor (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), a microphone, and the like. Note that the smart watch can be manufactured using the light-emitting device for the display panel 7304.

Figure 7D:
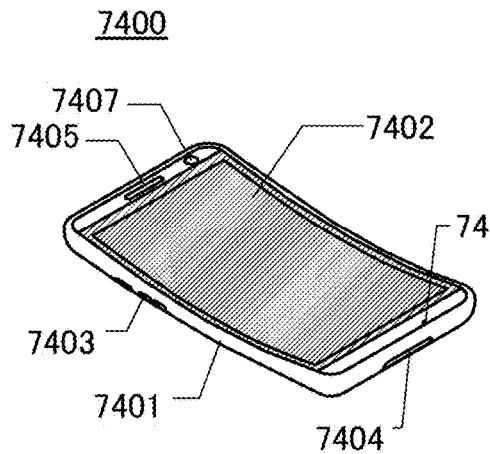
Figure 7D:
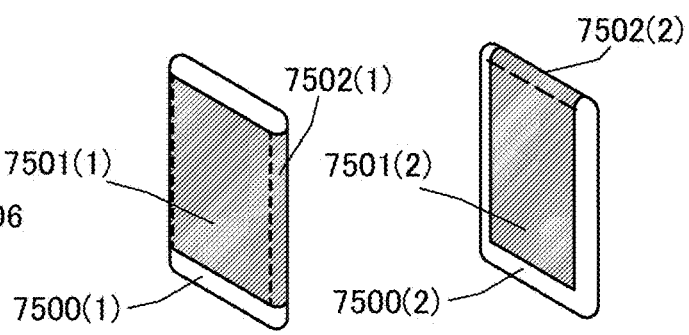

FIG. 7D illustrates an example of a mobile phone (e.g., smartphone). A mobile phone 7400 includes a housing 7401 provided with a display portion 7402, a microphone 7406, a speaker 7405, a camera 7407, an external connection portion 7404, an operation button 7403, and the like. In the case where a light-emitting device is manufactured by forming a light-emitting element of one embodiment of the present invention over a flexible substrate, the light-emitting element can be used for the display portion 7402 having a curved surface as illustrated in FIG. 7D.

When the display portion 7402 of the mobile phone 7400 illustrated in FIG. 7D is touched with a finger or the like, data can be input to the mobile phone 7400. In addition, operations such as making a call and creating an e-mail can be performed by touch on the display portion 7402 with a finger or the like.

There are mainly three screen modes of the display portion 7402. The first mode is a display mode mainly for displaying an image. The second mode is an input mode mainly for inputting data such as text. The third mode is a display-and-input mode in which two modes of the display mode and the input mode are combined.

For example, in the case of making a call or creating an e-mail, a character input mode mainly for inputting characters is selected for the display portion 7402 so that characters displayed on the screen can be input. In this case, it is preferable to display a keyboard or number buttons on almost the entire screen of the display portion 7402.

When a detection device such as a gyro sensor or an acceleration sensor is provided inside the mobile phone 7400, display on the screen of the display portion 7402 can be automatically changed by determining the orientation of the mobile phone 7400 (whether the mobile phone is placed horizontally or vertically).

The screen modes are changed by touch on the display portion 7402 or operation with the button 7403 of the housing 7401. The screen modes can be changed according to the kind of image displayed on the display portion 7402. For example, when a signal for an image to be displayed on the display portion is data of moving images, the screen mode is changed to the display mode. When the signal is text data, the screen mode is changed to the input mode.

Moreover, in the input mode, when input by touching the display portion 7402 is not performed for a certain period while a signal detected by an optical sensor in the display portion 7402 is detected, the screen mode may be controlled so as to be changed from the input mode to the display mode.

The display portion 7402 may function as an image sensor. For example, an image of a palm print, a fingerprint, or the like is taken by touch on the display portion 7402 with the palm or the finger, whereby personal authentication can be performed. In addition, when a backlight or a sensing light source that emits near-infrared light is provided in the display portion, an image of a finger vein, a palm vein, or the like can be taken.

Furthermore, the light-emitting device can be used for a mobile phone having a structure illustrated in FIG. 7D'-1 or FIG. 7D'-2, which is another structure of the mobile phone (e.g., smartphone).

Note that in the case of the structure illustrated in FIG. 7D'-1 or FIG. 7D'-2, text data, image data, or the like can be displayed on second screens 7502(1) and 7502(2) of housings 7500(1) and 7500(2) as well as first screens 7501(1) and 7501(2). Such a structure enables a user to easily see text data, image data, or the like displayed on the second screens 7502(1) and 7502(2) while the mobile phone is placed in user's breast pocket.

Figure 8A:
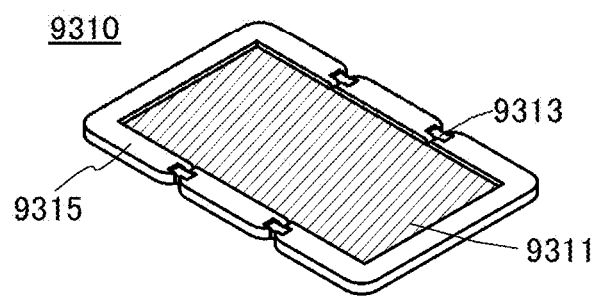
FIGS. 8A to 8C illustrate an electronic device.
Figure 8B:
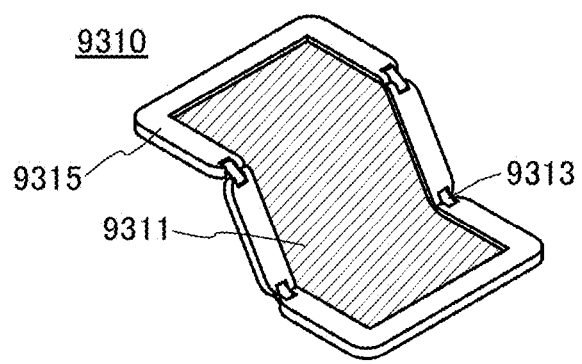
Figure 8C:
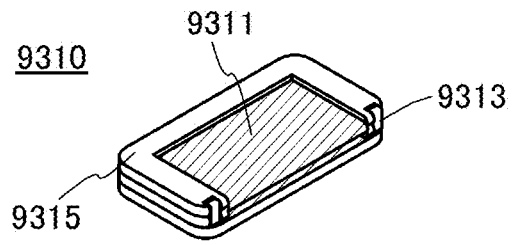

FIGS. 8A to 8C illustrate a foldable portable information terminal 9310. FIG. 8A illustrates the portable information terminal 9310 that is opened. FIG. 8B illustrates the portable information terminal 9310 that is being opened or being folded. FIG. 8C illustrates the portable information terminal 9310 that is folded. The portable information terminal 9310 is highly portable when folded. When the portable information terminal 9310 is opened, a seamless large display region is highly browsable.

A display panel 9311 is supported by three housings 9315 joined together by hinges 9313. Note that the display panel 9311 may be a touch panel (an input/output device) including a touch sensor (an input device). By bending the display panel 9311 at a connection portion between two housings 9315 with the use of the hinges 9313, the portable information terminal 9310 can be reversibly changed in shape from an opened state to a folded state. A light-emitting device of one embodiment of the present invention can be used for the display panel 9311. A display region 9312 in the display panel 9311 is a display region that is positioned at a side surface of the portable information terminal 9310 that is folded. On the display region 9312, information icons, frequently-used applications, file shortcuts to programs, and the like can be displayed, and confirmation of information and start of application can be smoothly performed.

As described above, the electronic devices can be obtained by application of the light-emitting device which is one embodiment of the present invention. Note that the light-emitting device can be used for electronic devices in a variety of fields without being limited to the electronic devices described in this embodiment.

Embodiment 6

In this embodiment, examples of lighting devices will be described with reference to FIG. 9. Each of the lighting devices uses a light-emitting device which is one embodiment of the present invention.

Figure 9:
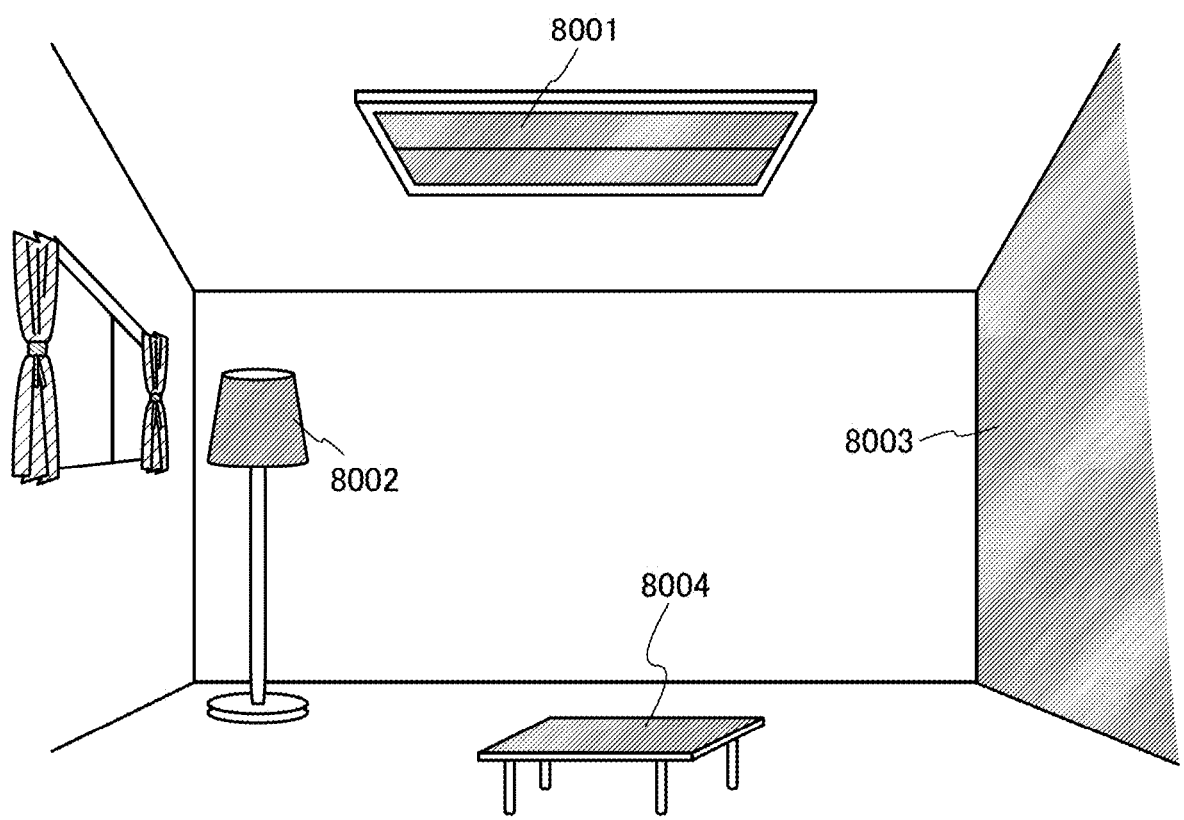
FIG. 9 illustrates lighting devices.

FIG. 9 illustrates an example in which the light-emitting device is used as an indoor lighting device 8001. Since the light-emitting device can have a large area, it can be used for a lighting device having a large area. In addition, with the use of a housing with a curved surface, a lighting device 8002 which includes the housing, a cover, or a support and in which a light-emitting region has a curved surface can also be obtained. A light-emitting element included in the light-emitting device described in this embodiment is in a thin film form, which allows the housing to be designed more freely. Thus, the lighting device can be elaborately designed in a variety of ways. In addition, a wall of the room may be provided with a large-sized lighting device 8003.

When the light-emitting device is used for a surface of a table, a lighting device 8004 that has a function as a table can be obtained. When the light-emitting device is used as part of other furniture, a lighting device that functions as the furniture can be obtained.

As described above, a variety of lighting devices that include the light-emitting device can be obtained. Note that these lighting devices are also embodiments of the present invention.

Note that the structure described in this embodiment can be used as appropriate in combination with any of the structures described in the other embodiments.

Embodiment 7

In this embodiment, a touch panel including a light-emitting element of one embodiment of the present invention or a light-emitting device of one embodiment of the present invention will be described with reference to FIGS. 11A and 11B, FIGS. 12A and 12B, FIGS. 13A and 13B, FIGS. 14A and 14B, and FIG. 15.

Figure 11A:
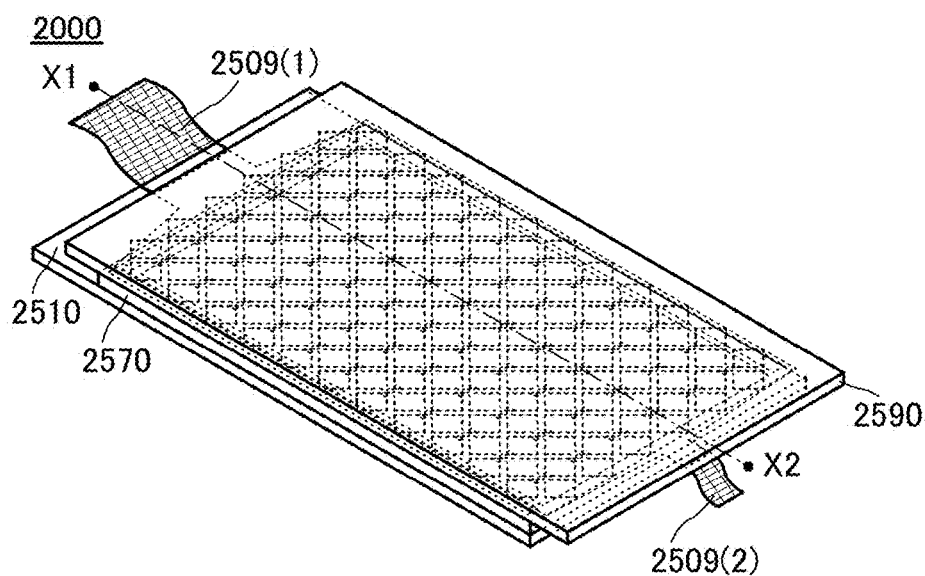
FIGS. 11A and 11B illustrate an example of a touch panel of an embodiment.
Figure 11B:
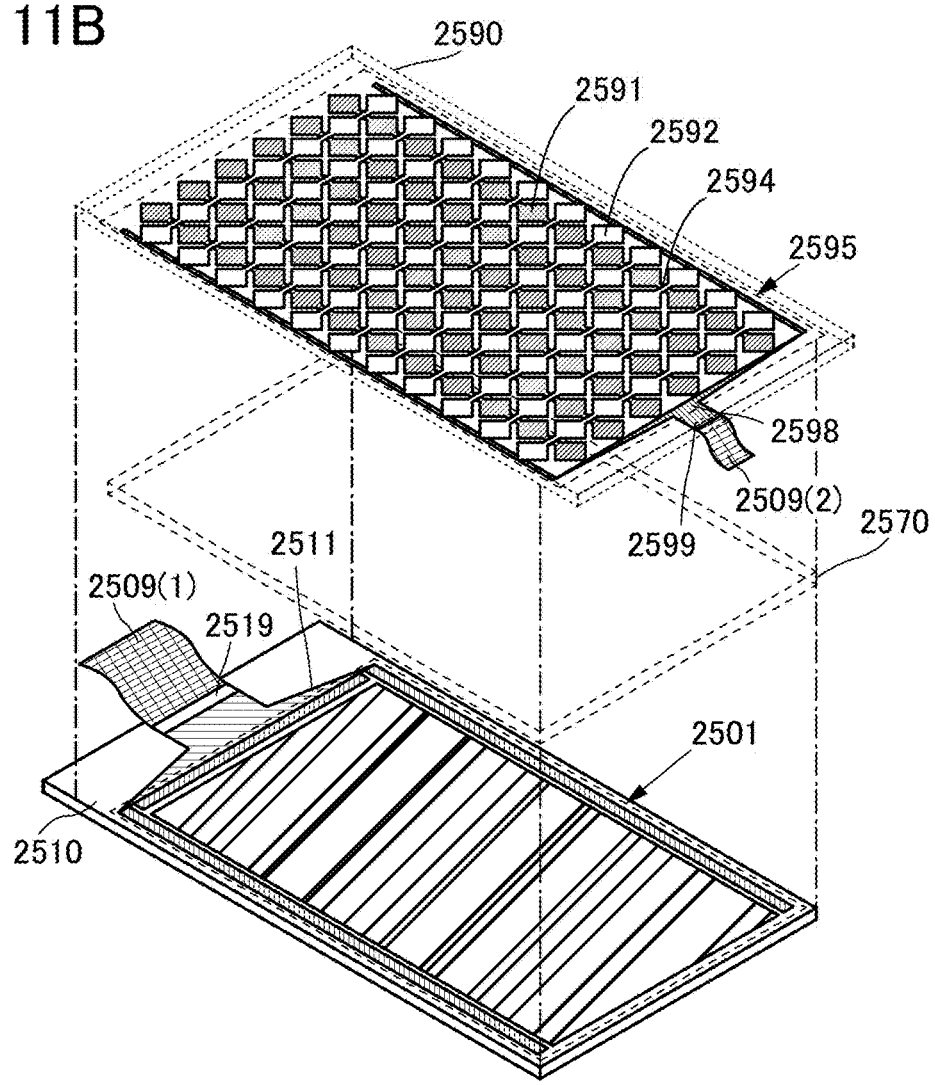

FIGS. 11A and 11B are perspective views of a touch panel 2000. Note that FIGS. 11A and 11B illustrate typical components of the touch panel 2000 for simplicity.

The touch panel 2000 includes a display portion 2501 and a touch sensor 2595 (see FIG. 11B). Furthermore, the touch panel 2000 includes a substrate 2510, a substrate 2570, and a substrate 2590. Note that the substrate 2510, the substrate 2570, and the substrate 2590 each have flexibility.

The display portion 2501 includes a plurality of pixels over the substrate 2510, and a plurality of wirings 2511 through which signals are supplied to the pixels. The plurality of wirings 2511 are led to a peripheral portion of the substrate 2510, and part of the plurality of wirings 2511 forms a terminal 2519. The terminal 2519 is electrically connected to an FPC 2509(1).

The substrate 2590 includes the touch sensor 2595 and a plurality of wirings 2598 electrically connected to the touch sensor 2595. The plurality of wirings 2598 are led to a peripheral portion of the substrate 2590, and part of the plurality of wirings 2598 forms a connection layer 2599. The connection layer 2599 is electrically connected to an FPC 2509(2). Note that in FIG. 11B, electrodes, wirings, and the like of the touch sensor 2595 provided on the back side of the substrate 2590 are indicated by solid lines for clarity.

As the touch sensor 2595, a capacitive touch sensor can be used, for example. Examples of the capacitive touch sensor are a surface capacitive touch sensor and a projected capacitive touch sensor.

Examples of the projected capacitive touch sensor are a self capacitive touch sensor and a mutual capacitive touch sensor, which differ mainly in the driving method. The use of a mutual capacitive touch sensor is preferable because multiple points can be sensed simultaneously.

First, an example of using a projected capacitive touch sensor will be described below with reference to FIG. 11B. Note that in the case of a projected capacitive touch sensor, a variety of sensors that can sense the closeness or the contact of a sensing target such as a finger can be used.

The projected capacitive touch sensor 2595 includes electrodes 2591 and electrodes 2592. The electrodes 2591 are electrically connected to any of the plurality of wirings 2598, and the electrodes 2592 are electrically connected to any of the other wirings 2598. The electrodes 2592 each have a shape of a plurality of quadrangles arranged in one direction with one corner of a quadrangle connected to one corner of another quadrangle with a wiring 2594 in one direction as illustrated in FIGS. 11A and 11B. In the same manner, the electrodes 2591 each have a shape of a plurality of quadrangles arranged in one direction with one corner of a quadrangle connected to one corner of another quadrangle; however, the direction in which the electrodes 2591 are connected is a direction crossing the direction in which the electrodes 2592 are connected. Note that the direction in which the electrodes 2591 are connected and the direction in which the electrodes 2592 are connected are not necessarily perpendicular to each other, and the electrodes 2591 may be arranged to intersect with the electrodes 2592 at an angle greater than 0° and less than 90°.

The intersecting area of the wiring 2594 and the one of the electrodes 2592 is preferably as small as possible. Such a structure allows a reduction in the area of a region where the electrodes are not provided, reducing unevenness in transmittance. As a result, unevenness in the luminance of light from the touch sensor 2595 can be reduced.

Note that the shapes of the electrodes 2591 and the electrodes 2592 are not limited to the above-mentioned shapes and can be any of a variety of shapes. For example, the plurality of electrodes 2591 may be provided so that space between the electrodes 2591 are reduced as much as possible, and a plurality of electrodes 2592 may be provided with an insulating layer sandwiched between the electrodes 2591 and the electrodes 2592. In that case, between two adjacent electrodes 2592, it is preferable to provide a dummy electrode which is electrically insulated from these electrodes, whereby the area of a region having a different transmittance can be reduced.

Figure 12A:
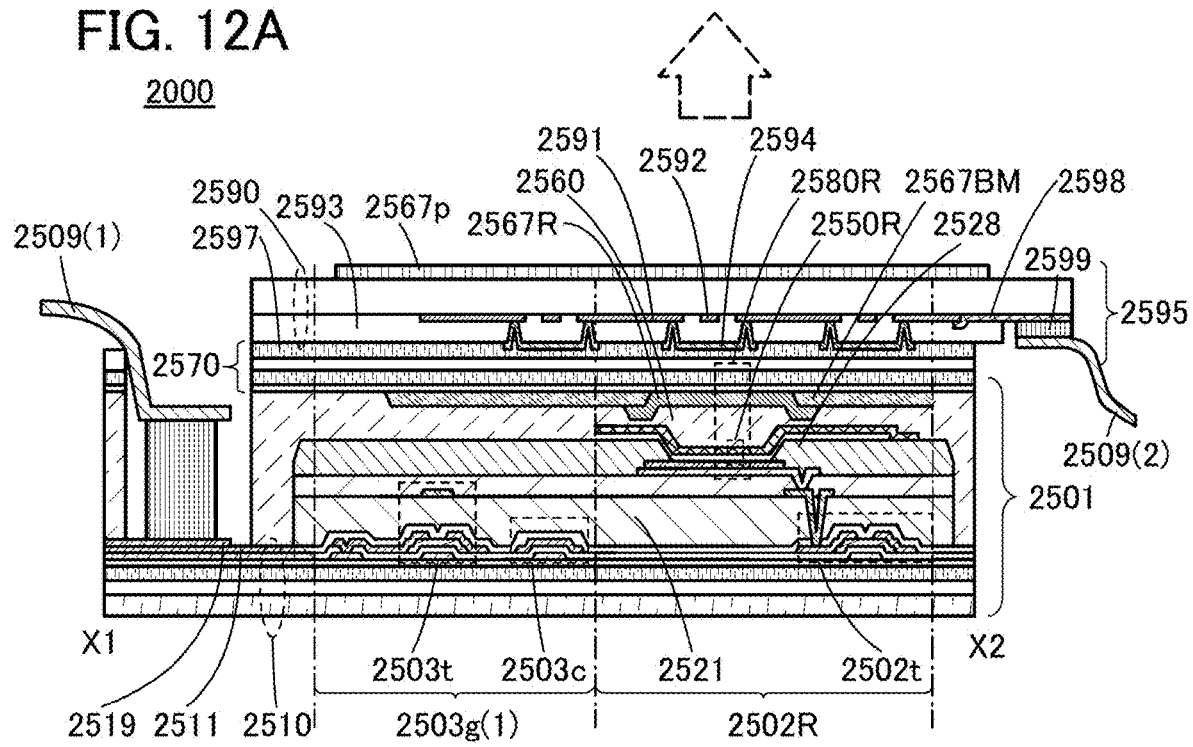
FIGS. 12A and 12B illustrate an example of a touch panel of an embodiment.

Next, the touch panel 2000 will be described in detail with reference to FIGS. 12A and 12B. FIG. 12A is a cross-sectional view taken along dashed-dotted line X1-X2 in FIG. 11A.

The touch sensor 2595 includes the electrodes 2591 and the electrodes 2592 provided in a staggered arrangement on the substrate 2590, an insulating layer 2593 covering the electrodes 2591 and the electrodes 2592, and the wiring 2594 that electrically connects the adjacent electrodes 2591 to each other.

An adhesive layer 2597 is provided below the wiring 2594. The substrate 2590 is attached to the substrate 2570 with the adhesive layer 2597 so that the touch sensor 2595 overlaps with the display portion 2501.

The electrodes 2591 and the electrodes 2592 are formed using a light-transmitting conductive material. As a light-transmitting conductive material, a conductive oxide such as indium oxide, indium tin oxide, indium zinc oxide, zinc oxide, or zinc oxide to which gallium is added can be used. Note that a film containing graphene may be used as well. The film including graphene can be formed, for example, by reducing a film containing graphene oxide. As a reducing method, a method with application of heat or the like can be employed.

For example, the electrodes 2591 and the electrodes 2592 may be formed by depositing a light-transmitting conductive material on the substrate 2590 by a sputtering method and then removing an unnecessary portion by any of various patterning techniques such as photolithography.

Examples of a material for the insulating layer 2593 are a resin such as acrylic or epoxy resin, a resin having a siloxane bond, and an inorganic insulating material such as silicon oxide, silicon oxynitride, or aluminum oxide.

The wiring 2594 is formed in an opening provided in the insulating layer 2593, whereby the adjacent electrodes 2591 are electrically connected to each other. A light-transmitting conductive material can be favorably used for the wiring 2594 because the aperture ratio of the touch panel can be increased. Moreover, a material having higher conductivity than the electrodes 2591 and 2592 can be favorably used for the wiring 2594 because electric resistance can be reduced.

Through the wiring 2594, a pair of electrodes 2591 is electrically connected to each other. Between the pair of electrodes 2591, the electrode 2592 is provided.

One wiring 2598 is electrically connected to any of the electrodes 2591 and 2592. Part of the wiring 2598 serves as a terminal. For the wiring 2598, a metal material such as aluminum, gold, platinum, silver, nickel, titanium, tungsten, chromium, molybdenum, iron, cobalt, copper, or palladium or an alloy material containing any of these metal materials can be used.

Through the connection layer 2599, the wiring 2598 and the FPC 2509(2) are electrically connected to each other. The connection layer 2599 can be formed using any of various kinds of anisotropic conductive films (ACF), anisotropic conductive pastes (ACP), and the like.

The adhesive layer 2597 has a light-transmitting property. For example, a thermosetting resin or an ultraviolet curable resin can be used; specifically, a resin such as an acrylic-based resin, an urethane-based resin, an epoxy-based resin, or a siloxane-based resin can be used.

The display portion 2501 includes a plurality of pixels arranged in a matrix. Each of the pixels includes a display element and a pixel circuit for driving the display element.

For the substrate 2510 and the substrate 2570, for example, a flexible material having a vapor permeability of $10^{-5}$ g/(m$^2$-day) or lower, preferably $10^{-6}$ g/(m$^2$ day) or lower can be favorably used. Note that materials whose thermal expansion coefficients are substantially equal to each other are preferably used for the substrate 2510 and the substrate 2570 respectively. For example, the coefficient of linear expansion of the materials are preferably lower than or equal to $1\times10^{-3}$/K, further preferably lower than or equal to $5\times10^{-5}$/K, and still further preferably lower than or equal to $1\times10^{-5}$/K.

A sealing layer 2560 preferably has a higher refractive index than the air.

The display portion 2501 includes a pixel 2502R. The pixel 2502R includes a light-emitting module 2580R.

The pixel 2502R includes a light-emitting element 2550R and a transistor 2502t that can supply electric power to the light-emitting element 2550R. Note that the transistor 2502t functions as part of the pixel circuit. The light-emitting module 2580R includes the light-emitting element 2550R and a coloring layer 2567R.

The light-emitting element 2550R includes a lower electrode, an upper electrode, and an EL layer between the lower electrode and the upper electrode.

In the case where the sealing layer 2560 is provided on the light extraction side, the sealing layer 2560 is in contact with the light-emitting element 2550R and the coloring layer 2567R.

The coloring layer 2567R overlaps with the light-emitting element 2550R. Accordingly, part of light emitted from the light-emitting element 2550R passes through the coloring layer 2567R and is emitted to the outside of the light-emitting module 2580R as indicated by an arrow in FIG. 12A.

The display portion 2501 includes a light-blocking layer 2567BM on the light extraction side. The light-blocking layer 2567BM is provided so as to surround the coloring layer 2567R.

The display portion 2501 includes an anti-reflective layer 2567p in a region overlapping with pixels. As the anti-reflective layer 2567p, a circular polarizing plate can be used, for example.

An insulating layer 2521 is provided in the display portion 2501. The insulating layer 2521 covers the transistor 2502t. With the insulating layer 2521, unevenness caused by the pixel circuit is planarized. The insulating layer 2521 may serve also as a layer for preventing diffusion of impurities. This can prevent a reduction in the reliability of the transistor 2502t or the like due to diffusion of impurities.

The light-emitting element 2550R is formed above the insulating layer 2521. A partition 2528 is provided so as to cover end portions of the lower electrode in the light-emitting element 2550R. Note that a spacer for controlling the distance between the substrate 2510 and the substrate 2570 may be provided over the partition 2528.

A scan line driver circuit 2503g(1) includes a transistor 2503t and a capacitor 2503c. Note that the driver circuit and the pixel circuits can be formed in the same process over the same substrate.

Over the substrate 2510, the wirings 2511 through which a signal can be supplied are provided. Over the wirings 2511, the terminal 2519 is provided. The FPC 2509(1) is electrically connected to the terminal 2519. The FPC 2509(1) has a function of supplying signals such as a pixel signal and a synchronization signal. Note that a printed wiring board (PWB) may be attached to the FPC 2509(1).

For the display portion 2501, transistors with a variety of structures can be used. In the example of FIG. 12A, a bottom-gate transistor is used. In each of the transistor 2502*t* and the transistor 2503*t* illustrated in FIG. 12A, a semiconductor layer including an oxide semiconductor can be used for a channel region. Alternatively, in each of the transistor 2502*t* and the transistor 2503*t*, a semiconductor layer including amorphous silicon can be used for a channel region. Further alternatively, in each of the transistor 2502*t* and the transistor 2503*t*, a semiconductor layer including polycrystalline silicon that is obtained by crystallization process such as laser annealing can be used for a channel region.

Figure 12B:
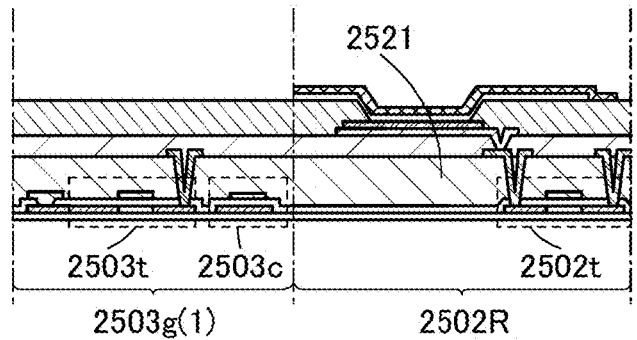

FIG. 12B illustrates the structure of the display portion 2501 in which a top-gate transistor is used.

In the case of a top-gate transistor, a semiconductor layer including polycrystalline silicon, a single crystal silicon film that is transferred from a single crystal silicon substrate, or the like may be used for a channel region as well as the above semiconductor layers that can be used for a bottom-gate transistor.

Next, a touch panel having a different structure from that illustrated in FIGS. 12A and 12B will be described with reference to FIGS. 13A and 13B.

Figure 13A:
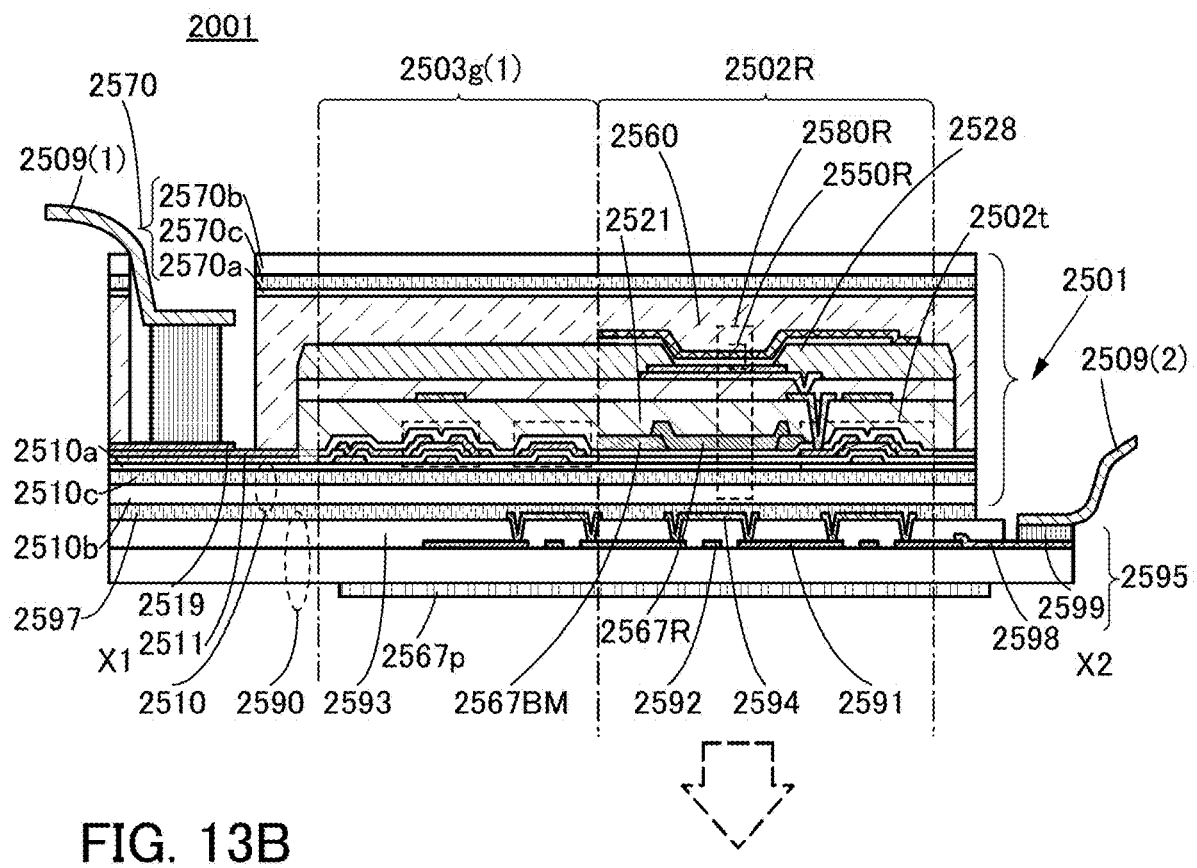
FIGS. 13A and 13B illustrate an example of a touch panel of an embodiment.
Figure 13B:
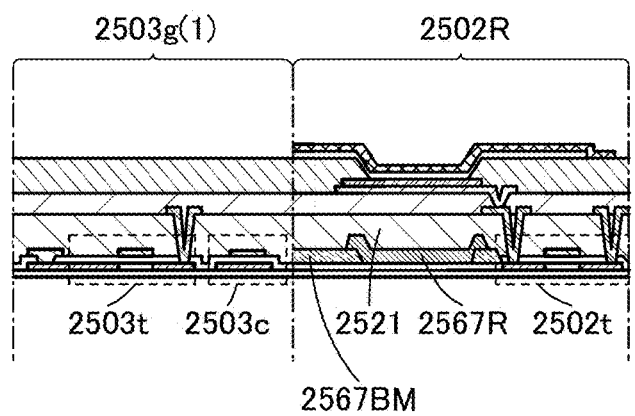

FIGS. 13A and 13B are cross-sectional views of a touch panel 2001. In the touch panel 2001 illustrated in FIGS. 13A and 13B, the position of the touch sensor 2595 relative to the display portion 2501 is different from that in the touch panel 2000 illustrated in FIGS. 12A and 12B. Different structures will be described in detail below, and the above description of the touch panel 2000 can be referred to for the other similar structures.

The coloring layer 2567R overlaps with the light-emitting element 2550R. The light-emitting element 2550R illustrated in FIG. 13A emits light to the side where the transistor 2502*t* is provided. Accordingly, part of light emitted from the light-emitting element 2550R passes through the coloring layer 2567R and is emitted to the outside of the light-emitting module 2580R as indicated by an arrow in FIG. 13A.

The display portion 2501 includes the light-blocking layer 2567BM on the light extraction side. The light-shielding layer 2567BM is provided so as to surround the coloring layer 2567R.

The touch sensor 2595 is provided on the substrate 2510 side of the display portion 2501 (see FIG. 13A).

The display portion 2501 and the touch sensor 2595 are attached to each other with the adhesive layer 2597 provided between the substrate 2510 and the substrate 2590.

For the display portion 2501, transistors with a variety of structures can be used. In the example of FIG. 13A, a bottom-gate transistor is used. In the example of FIG. 13B, a top-gate transistor is used.

Then, an example of a driving method of the touch panel will be described with reference to FIGS. 14A and 14B.

Figure 14A:
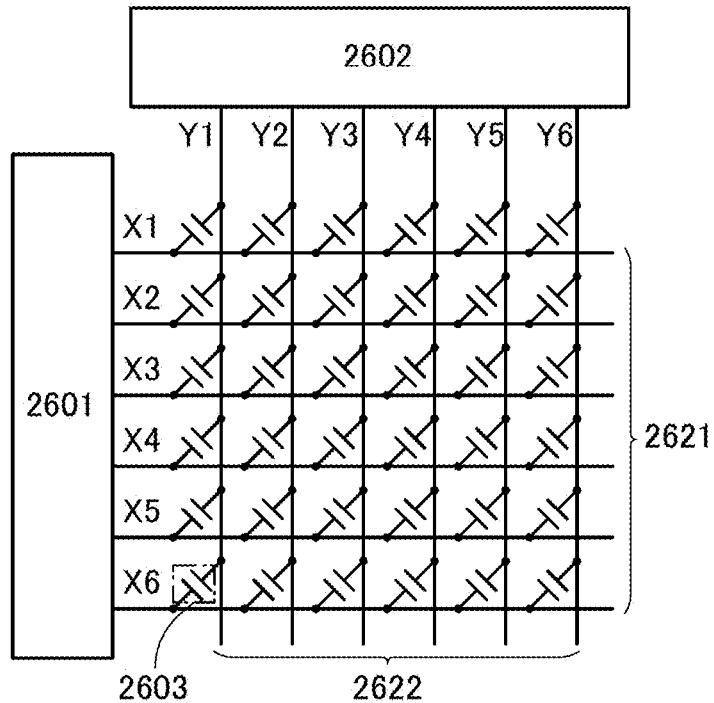
FIGS. 14A and 14B are a block diagram and a timing chart of a touch sensor.

FIG. 14A is a block diagram illustrating the structure of a mutual capacitive touch sensor. FIG. 14A illustrates a pulse voltage output circuit 2601 and a current sensing circuit 2602. Note that in the example of FIG. 14A, six wirings X1-X6 represent electrodes 2621 to which a pulse voltage is supplied, and six wirings Y1-Y6 represent electrodes 2622 that sense a change in current. FIG. 14A also illustrates a capacitor 2603 that is formed in a region where the electrodes 2621 and 2622 overlap with each other. Note that functional replacement between the electrodes 2621 and 2622 is possible.

The pulse voltage output circuit 2601 is a circuit for sequentially applying a pulse voltage to the wirings X1 to X6. By application of a pulse voltage to the wirings X1 to X6, an electric field is generated between the electrodes 2621 and 2622 of the capacitor 2603. When the electric field between the electrodes is shielded, for example, a change occurs in the capacitor 2603 (mutual capacitance). The approach or contact of a sensing target can be sensed by utilizing this change.

The current sensing circuit 2602 is a circuit for detecting changes in current flowing through the wirings Y1 to Y6 that are caused by the change in mutual capacitance in the capacitor 2603. No change in current value is detected in the wirings Y1 to Y6 when there is no approach or contact of a sensing target, whereas a decrease in current value is detected when mutual capacitance is decreased owing to the approach or contact of a sensing target. Note that an integrator circuit or the like is used for detection of current values.

Figure 14B:
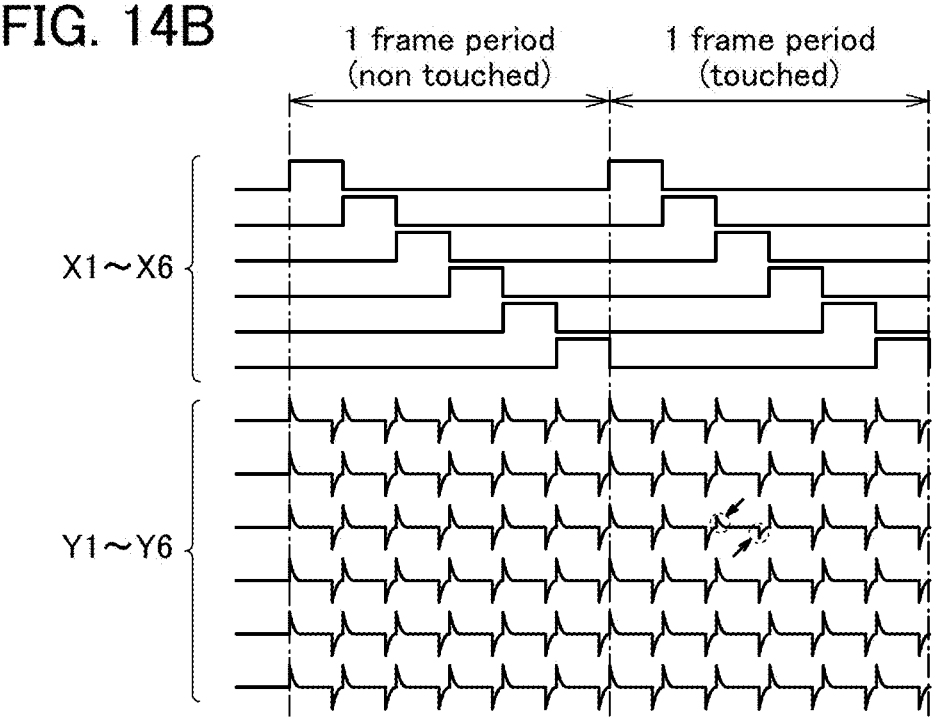

FIG. 14B is a timing chart showing input and output waveforms in the mutual capacitive touch sensor illustrated in FIG. 14A. In FIG. 14B, sensing of a sensing target is performed in all the rows and columns in one frame period. FIG. 14B shows a period when a sensing target is not sensed (not touched) and a period when a sensing target is sensed (touched). Sensed current values of the wirings Y1 to Y6 are shown as the waveforms of voltage values.

A pulse voltage is sequentially applied to the wirings X1 to X6, and the waveforms of the wirings Y1 to Y6 change in accordance with the pulse voltage. When there is no approach or contact of a sensing target, the waveforms of the wirings Y1 to Y6 change in accordance with changes in the voltages of the wirings X1 to X6. The current value is decreased at the point of approach or contact of a sensing target and accordingly the waveform of the voltage value changes. By detecting a change in mutual capacitance in this manner, the approach or contact of a sensing target can be sensed.

Figure 15:
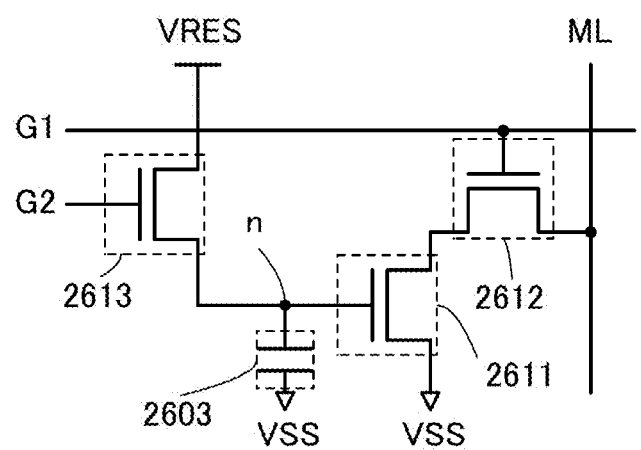
FIG. 15 is a circuit diagram of a touch sensor.

Although FIG. 14A is a passive touch sensor in which only the capacitor 2603 is provided at the intersection of wirings as a touch sensor, an active touch sensor including a transistor and a capacitor may be used. FIG. 15 is a sensor circuit included in an active touch sensor.

The sensor circuit illustrated in FIG. 15 includes the capacitor 2603, a transistor 2611, a transistor 2612, and a transistor 2613.

A signal G2 is input to agate of the transistor 2613. A voltage VRES is applied to one of a source and a drain of the transistor 2613, and one electrode of the capacitor 2603 and a gate of the transistor 2611 are electrically connected to the other of the source and the drain of the transistor 2613. One of a source and a drain of the transistor 2611 is electrically connected to one of a source and a drain of the transistor 2612, and a voltage VSS is applied to the other of the source and the drain of the transistor 2611. A signal G1 is input to a gate of the transistor 2612, and a wiring ML is electrically connected to the other of the source and the drain of the transistor 2612. The voltage VSS is applied to the other electrode of the capacitor 2603.

Next, the operation of the sensor circuit illustrated in FIG. 15 will be described. First, a potential for turning on the transistor 2613 is supplied as the signal G2, and a potential with respect to the voltage VRES is thus applied to the node n connected to the gate of the transistor 2611. Then, a potential for turning off the transistor 2613 is applied as the signal G2, whereby the potential of the node n is maintained. Then, mutual capacitance of the capacitor 2603 changes owing to the approach or contact of a sensing target such as a finger, and accordingly the potential of the node n is changed from VRES.

In reading operation, a potential for turning on the transistor 2612 is supplied as the signal G1. A current flowing through the transistor 2611, that is, a current flowing through the wiring ML is changed in accordance with the potential of the node n. By sensing this current, the approach or contact of a sensing target can be sensed.

In each of the transistors 2611, 2612, and 2613, an oxide semiconductor layer is preferably used as a semiconductor layer in which a channel region is formed. In particular, such a transistor is preferably used as the transistor 2613 so that the potential of the node n can be held for a long time and the frequency of operation of resupplying VRES to the node n (refresh operation) can be reduced.

At least part of this embodiment can be implemented in combination with any of the embodiments described in this specification as appropriate.

Example 1

In this example, results of calculating power consumption of light-emitting devices performing white display will be described. In the light-emitting device of the present invention, light-emitting elements (a yellow light-emitting element: Light-emitting Element 1, a blue light-emitting element: Light-emitting Element 2, and a green light-emitting element: Light-emitting Element 3) were used. In the light-emitting device of a comparative example, light-emitting elements (a yellow light-emitting element: Comparative Light-emitting Element 1, a blue light-emitting element: Comparative Light-emitting Element 2, and a red light-emitting element: Comparative Light-emitting Element 3) were used.

The reason why Light-emitting Elements 1 to 3 are light-emitting elements that emit yellow light, blue light, and green light respectively and Comparative Light-emitting Elements 1 to 3 are light-emitting elements that emit yellow light, blue light, and red light respectively is that such light of the colors are needed for obtaining white light having chromaticity at approximately D65 (light having chromaticity coordinates of (x, y)=(0.313, 0.329) on the xy chromaticity diagram). Note that red light is not needed for obtaining white light in the light-emitting device of this example, and green light is not needed for obtaining white light in the light-emitting device of the comparative example; therefore, description thereof is omitted.

Structure formulae of organic compounds used in Light-emitting Elements 1 to 3 and Comparative Light-emitting Elements 1 to 3 are shown below.

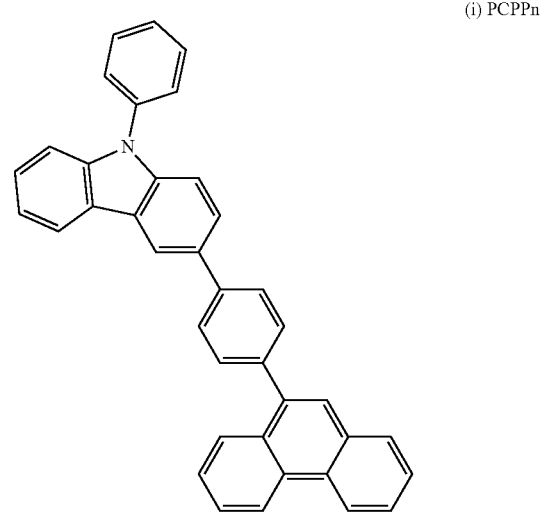

(i) PCPPn

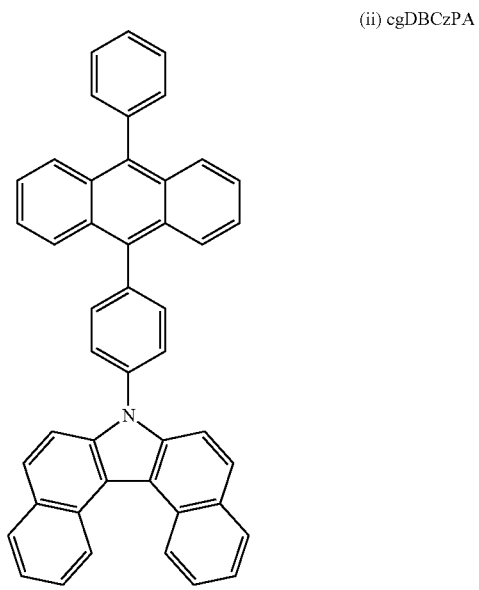

(ii) cgDBCzPA (iii) 1,6BnfAPrn-03
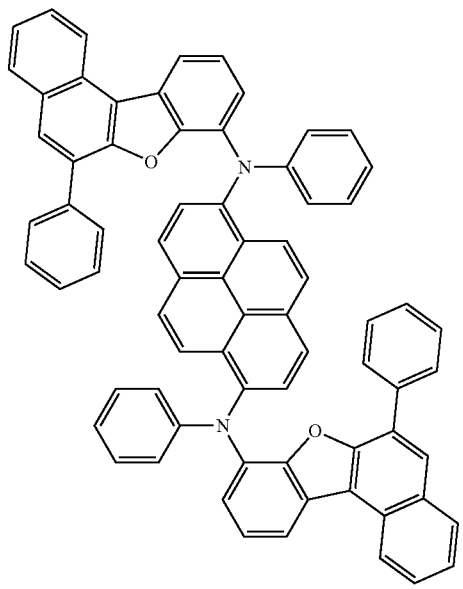
(iv) BPhen
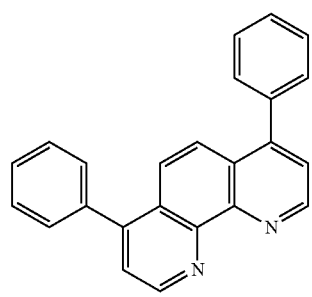
(vi) BPAFLP
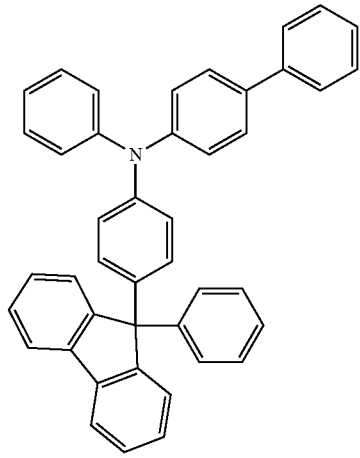
(v) DBT3P-II
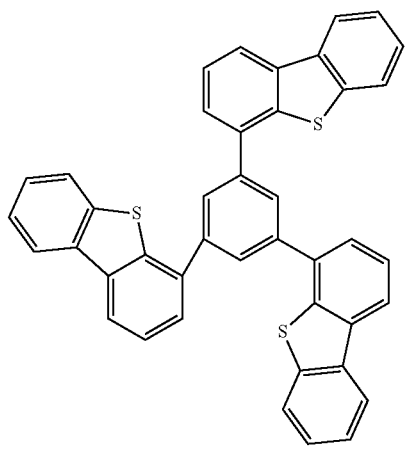
(x) 1,6mMemFLPAPrn
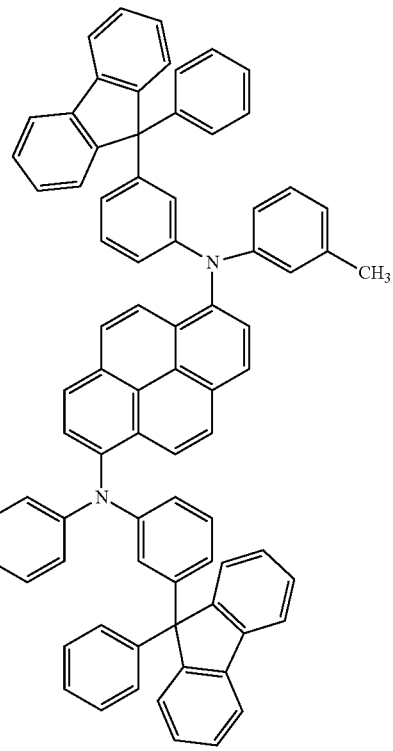
(vii) 2mDBTBPDBq-II
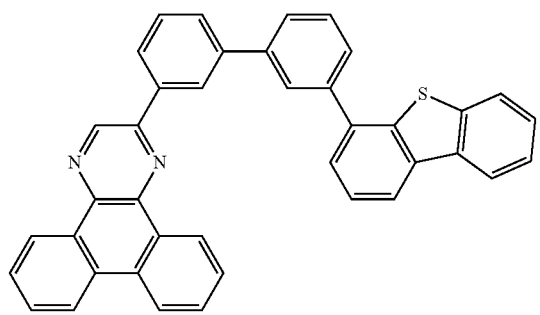

-continued

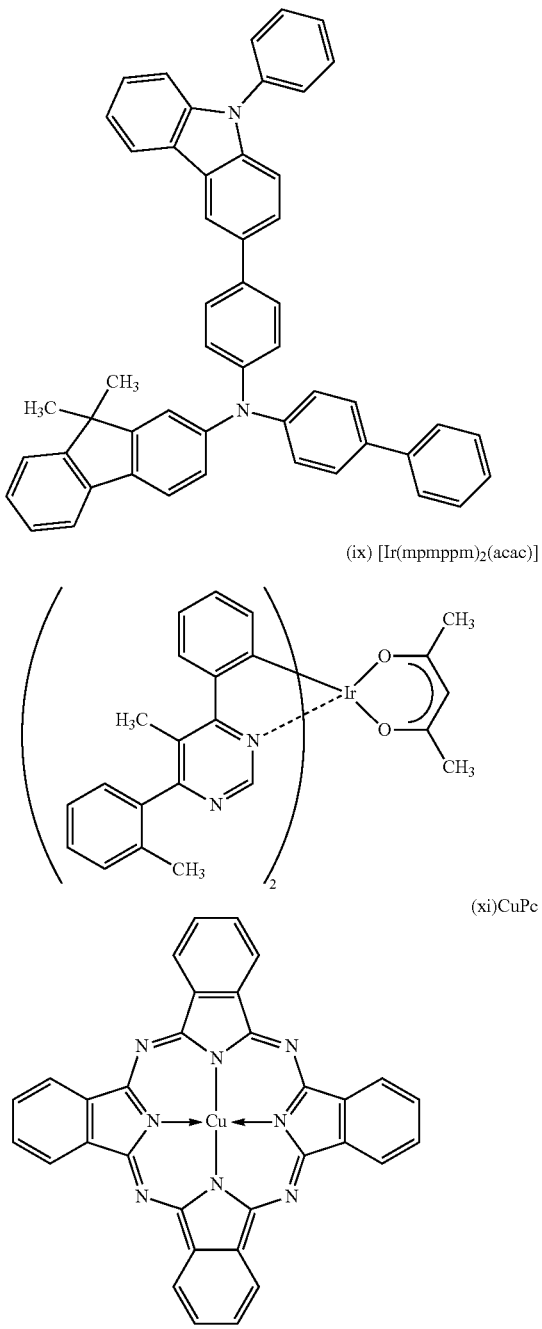

(viii) PCBBiF (ix) [Ir(mpmppm)₂(acac)]

(xi) CuPc (Methods for fabricating Light-emitting Elements 1 to 3 and Comparative Light-emitting Elements 1 to 3)

First, an alloy film of silver (Ag), palladium (Pd), and copper (Cu) (the alloy film is hereinafter referred to as APC) was formed over a glass substrate by a sputtering method to form a first electrode (reflective electrode). The thickness of the first electrode was 100 nm and the electrode area was 2 mm×2 mm.

Next, as a transparent conductive film, a film of indium tin oxide containing silicon oxide was formed over the first electrode by a sputtering method. The thickness of the transparent conductive film for Light-emitting Element 1 was 30 nm, that for Light-emitting Element 2 was 80 nm, and that for Light-emitting Element 3 was 30 nm. The thickness of the transparent conductive film for Comparative Light-emitting Element 1 was 30 nm, that for Comparative Light-emitting Element 2 was 60 nm, and that for Comparative Light-emitting Element 3 was 60 nm.

Then, as pretreatment of evaporation of an organic compound layer, a surface of the substrate provided with the reflective electrode and the transparent conductive film was washed with water, baking was performed at 200° C. for one hour, and then UV ozone treatment was performed for 370 seconds.

After that, the substrate was transferred into a vacuum evaporation apparatus in which the pressure had been reduced to approximately $10^{-4}$ Pa, and was subjected to vacuum baking at 170° C. for 30 minutes in a heating chamber of the vacuum evaporation apparatus, and then the substrate was cooled down for about 30 minutes.

Then, the substrate was fixed to a substrate holder provided in the vacuum evaporation apparatus so that the surface on which the transparent conductive film was formed faced downward. The pressure in the vacuum evaporation apparatus was reduced to approximately $10^{-4}$ Pa. After that, on the transparent conductive film, 3-[4-(9-phenanthryl)-phenyl]-9-phenyl-9H-carbazole (abbreviation: PCPPn) represented by Structural Formula (i) and molybdenum(VI) oxide were deposited by co-evaporation using resistance heating, whereby a first hole-injection layer was formed. The thickness of the first hole-injection layer for Light-emitting Element 1 was 60 nm, that for Light-emitting Element 2 was 47.5 nm, and that for Light-emitting Element 3 was 40 nm. The thickness of the first hole-injection layer for Comparative Light-emitting Element 1 was 55 nm, that for Comparative Light-emitting Element 2 was 70 nm, and that for Comparative Light-emitting Element 3 was 45 nm. The weight ratio of PCPPn to molybdenum oxide was adjusted to 1:0.5.

Next, on the first hole-injection layer, PCPPn was deposited to a thickness of 10 nm to form a first hole-transport layer.

As for each of Light-emitting Elements 1 to 3, on the first hole-transport layer, a first light-emitting layer was formed by deposition of 7-[4-(10-phenyl-9-anthryl)phenyl]-7H-dibenzo[c,g]carbazole (abbreviation: cgDBCzPA) represented by Structural Formula (ii) and N,N-(pyrene-1,6-diyl) bis[(6,N-diphenylbenzo[b]naphtho[1,2-d]furan)-8-amine] (abbreviation: 1,6BnfAPrn-03) represented by Structural Formula (iii) to a thickness of 25 nm so that the weight ratio of cgDBCzPA to 1,6BnfAPrn-03 was 1:0.05.

As for each of Comparative Light-emitting Elements 1 to 3, on the first hole-transport layer, a first light-emitting layer was formed by deposition of cgDBCzPA and N,N'-bis(3-methylphenyl)-N,N'-bis[3-(9-phenyl-9H-fluoren-9-yl)phenyl]pyrene-1,6-diamine (abbreviation: 1,6mMemFLPAPrn) represented by Structural Formula (x) to a thickness of 25 nm so that the weight ratio of cgDBCzPA to 1,6mMemFL-PAPrn was 1:0.05.

Then, a first electron-transport layer was formed over the first light-emitting layer in such a way that cgDBCzPA was deposited to a thickness of 5 nm and bathophenanthroline (abbreviation: BPhen) represented by Structural Formula (iv) was deposited to a thickness of 15 nm.

After the first electron-transport layer was formed, lithium oxide ($Li_2O$) was evaporated to a thickness of 0.1 nm. Then, copper phthalocyanine (abbreviation: CuPc) represented by Structural Formula (xi) was evaporated to a thickness or 2 nm. After that, 4,4',4"-(benzene-1,3,5-triyl)tri(dibenzothiophene) (abbreviation: DBT3P-II) represented by Structural Formula (v) and molybdenum(VI) oxide were co-evaporated so that the weight ratio of DBT3P-II to molybdenum oxide was 1:0.5. In such a manner, an intermediate layer was formed. The thickness of the intermediate layer was 12.5 nm.

Next, on the intermediate layer, 4-phenyl-4'-(9-phenylfluoren-9-yl)triphenylamine (abbreviation: BPAFLP) represented by Structural Formula (vi) was evaporated to a thickness of 20 nm, whereby a second hole-transport layer was formed.

After the second hole-transport layer was formed, 2-[3'-(dibenzothiophen-4-yl)biphenyl-3-yl]dibenzo[f,h]quinoxaline (abbreviation: 2mDBTBPDBq-II) represented by Structural Formula (vii), N-(1,1'-biphenyl-4-yl)-9,9-dimethyl-N-[4-(9-phenyl-9H-carbazol-3-yl)phenyl]-9H-fluoren-2-amine (abbreviation: PCBBiF) represented by Structural Formula (viii), and bis{2-[5-methyl-6-(2-methylphenyl)-4-pyrimidinyl-κN3]phenyl-κC}(2,4-pentanedionato-κ$^2$O,O')iridium (III) (abbreviation: [Ir(mpmppm)$_2$(acac)]) represented by Structural Formula (ix) were co-evaporated so that the weight ratio of 2mDBTBPDBq-II to PCBBiF and [Ir(mpmppm)$_2$(acac)] was 0.8:0.2:0.06. In this manner, a second light-emitting layer was formed. The thickness of the second light-emitting layer was 40 nm.

Then, on the second light-emitting layer, 2mDBTBPDBq-II was evaporated to a thickness of 15 nm. As for each of Light-emitting Elements 1 to 3, BPhen was also evaporated to a thickness of 20 nm. As for each of Comparative Light-emitting Elements 1 to 3, BPhen was also evaporated to a thickness of 15 nm. In this manner, a second electron-transport layer was formed.

After that, lithium fluoride was evaporated to a thickness of 1 nm to form an electron-injection layer. Then, silver and magnesium were co-evaporated to a thickness of 15 nm with a volume ratio of 1:0.1 (=silver:magnesium). Next, ITO was deposited to a thickness of 70 nm by a sputtering method. In this manner, a second electrode (semi-transmissive and semi-reflective electrode) was formed. Through the above steps, Light-emitting Elements 1 to 3 and Comparative Light-emitting Elements 1 to 3 were fabricated. Note that in all the above evaporation steps, evaporation was performed by a resistance-heating method.

The element structures of Light-emitting Elements 1 to 3 and Comparative Light-emitting Elements 1 to 3 are listed below.

TABLE 1

| Reflective Electrode | | Hole-injection Layer | First Hole-transport Layer | First Light-emitting Layer | | First Electron-transport Layer | |
|---|---|---|---|---|---|---|---|
| APC | ITSO | PCPPn:MoOx 1:0.5 | PCPPn | cgDBCzPA:*1 1:0.05 | | cgDBCzPA | BPhen |
| 100 nm | *3 | *4 | 10 nm | 25 nm | | 5 nm | 15 nm |
| | | | | | | | Continued on *6 |

| Intermediate Layer | | | Second Hole-transport Layer | Second Light-emitting Layer | Second Electron-transport Layer | |
|---|---|---|---|---|---|---|
| Li$_2$O | CuPC | DBT3P-II:MoOx 1:0.5 | BPAFLP | 2mDBTBPDBq-II:PCBBiF:[Ir(mpmppm)$_2$(acac)] 0.8:0.2:0.06 | 2mDBTBPDBq-II | BPhen |
| 0.1 nm | 2 nm | 12.5 nm | 20 nm | 40 nm | 15 nm | *5 |
| *6 | | | | | | Continued on *7 |

| Electron-injection Layer | Semi-transmissive and Semi-reflective Electrode | | Color Filter |
|---|---|---|---|
| LiF | Ag:Mg 1:0.1 | ITO | *2 |
| 1 nm | 15 nm | 70 nm | |
| *7 | | | |

*1 Light-emitting Elements 1 to 3: 1,6BnfAPrn-03

Comparative Light-emitting Elements 1 to 3: 1,6mMemFLPAPrn

*2 Light-emitting Element 1 and Comparative Light-emitting Element 1: 0.8 μm

Light-emitting Elemenet 2 and Comparative Light-emitting Element 2: Blue 0.8 μm

Light-emitting Element 3: Green 1.3 μm, Comparative Light-emitting Element 3: Red 2.4 μm

*3 Light-emitting Element 1: 30 nm, Light-emitting Element 2: 80 nm, Light-emitting Element 3: 30 nm Comparative Light-emitting Element 1: 30 nm, Comparative Light-emitting Element 2: 60 nm, Comparative Light-emitting Element 3: 60 nm

*4 Light-emitting Element 1: 60 nm, Light-emitting Element 2: 47.5 nm, Light-emitting Element 3: 40 nm Comparative Light-emitting Element 1: 55 nm, Comparative Light-emitting Element 2: 70 nm, Comparative Light-emitting Element 3: 45 nm

*5 Light-emitting Elements 1 to 3: 20 nm

Comparative Light-emitting Elements 1 to 3: 15 nm

Each of Light-emitting Elements 1 to 3 and Comparative Light-emitting Elements 1 to 3 was sealed using a glass substrate in a glove box containing a nitrogen atmosphere so as not to be exposed to the air (specifically, a sealing material was applied to surround the element, and at the time of sealing, UV treatment (with 365-nm ultraviolet light at 6 J/cm$^2$) was performed and heat treatment was performed at 80° C. for 1 hour). Then, initial characteristics of these light-emitting elements were measured. Note that the measurement was carried out at room temperature (in an atmosphere kept at 25° C.).

Figure 16:
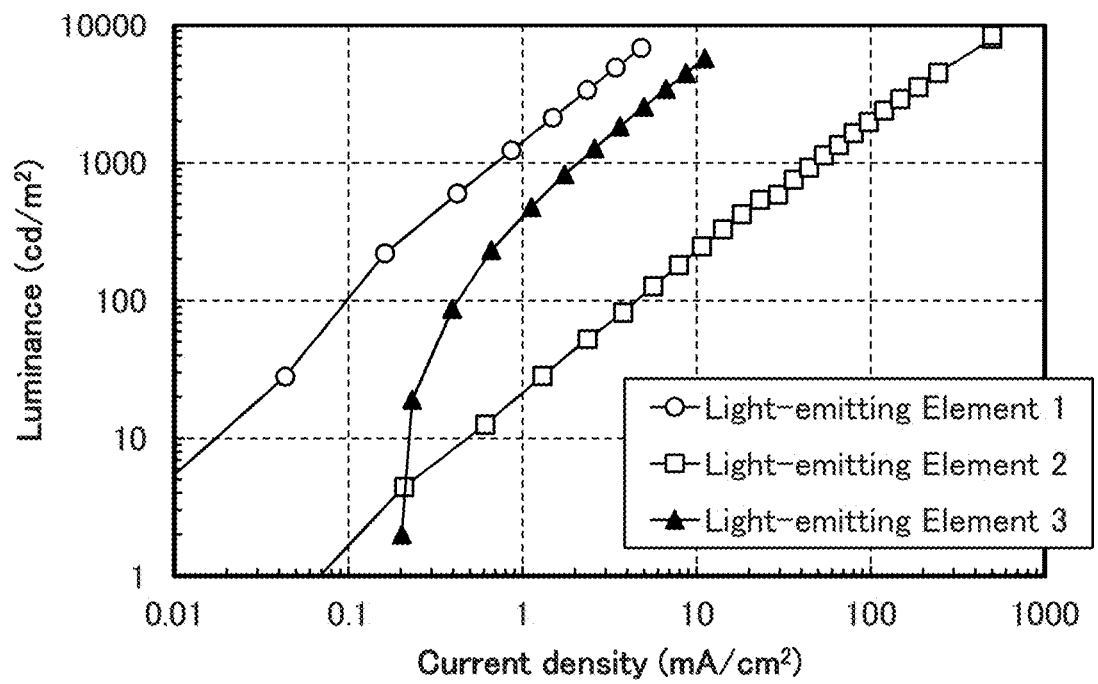
FIG. 16 shows luminance-current density characteristics of Light-emitting Elements 1 to 3.
Figure 17:
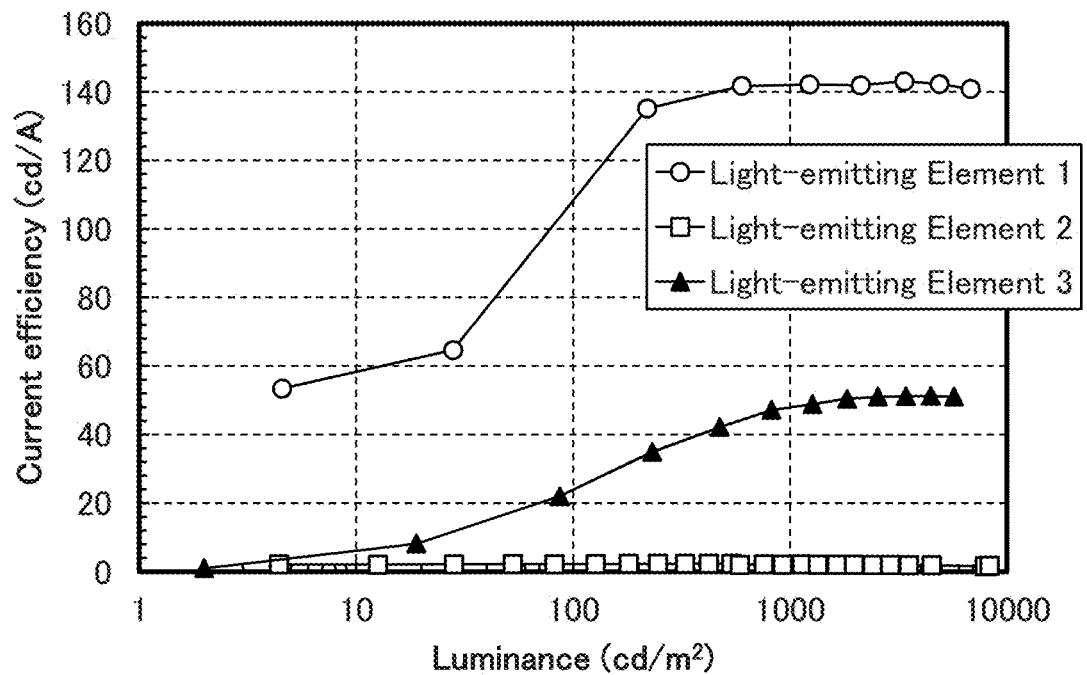
FIG. 17 shows current efficiency-luminance characteristics of Light-emitting Elements 1 to 3.
Figure 18:
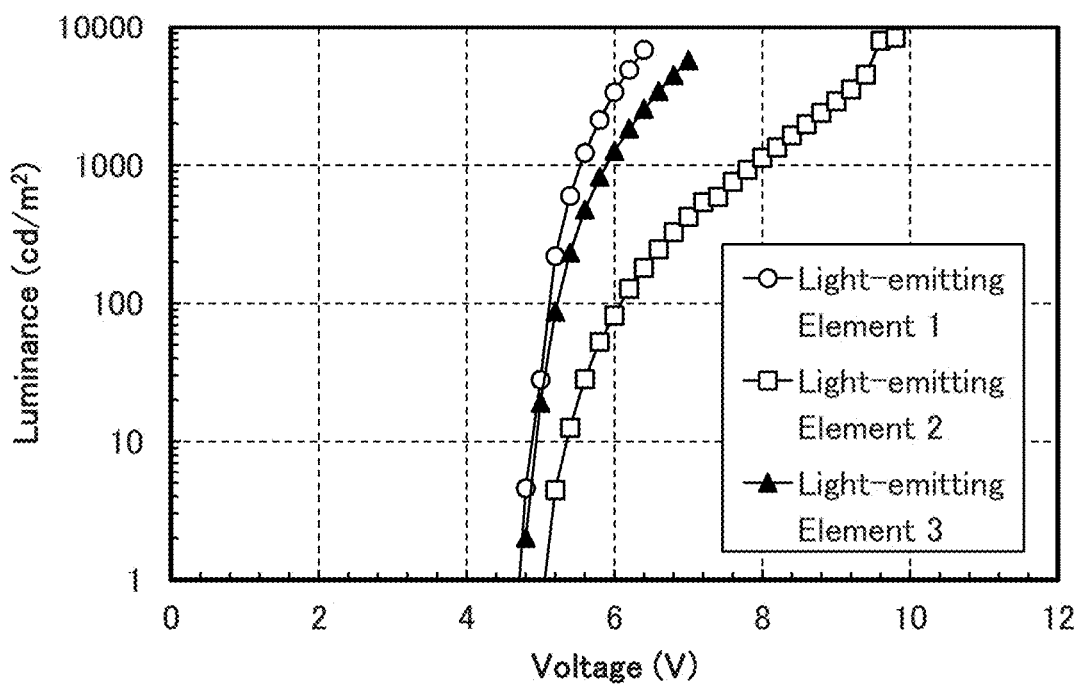
FIG. 18 shows luminance-voltage characteristics of Light-emitting Elements 1 to 3.
Figure 19:
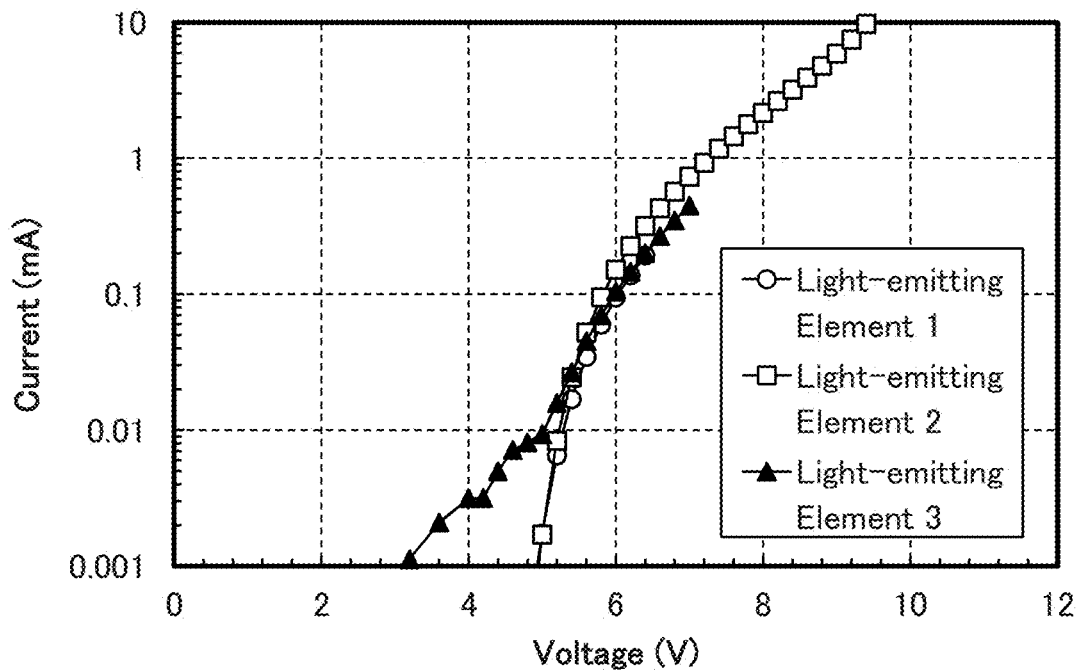
FIG. 19 shows current-voltage characteristics of Light-emitting Elements 1 to 3.
Figure 20:
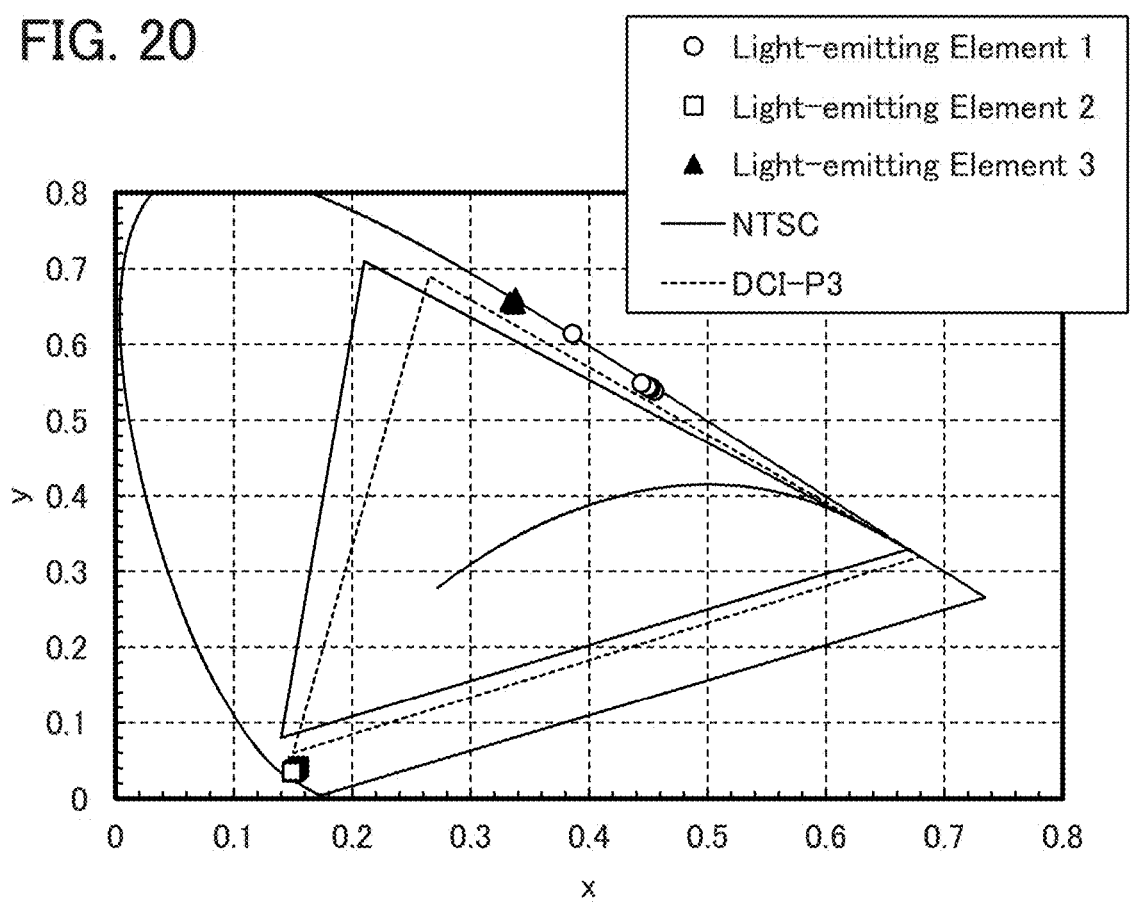
FIG. 20 shows chromaticity coordinates of Light-emitting Elements 1 to 3.

FIG. 16 shows luminance-current density characteristics of Light-emitting Elements 1 to 3, FIG. 17 shows current efficiency-luminance characteristics thereof, FIG. 18 shows luminance-voltage characteristics thereof, FIG. 19 shows current-voltage characteristics thereof, and FIG. 20 shows chromaticity coordinates thereof.

Figure 21:
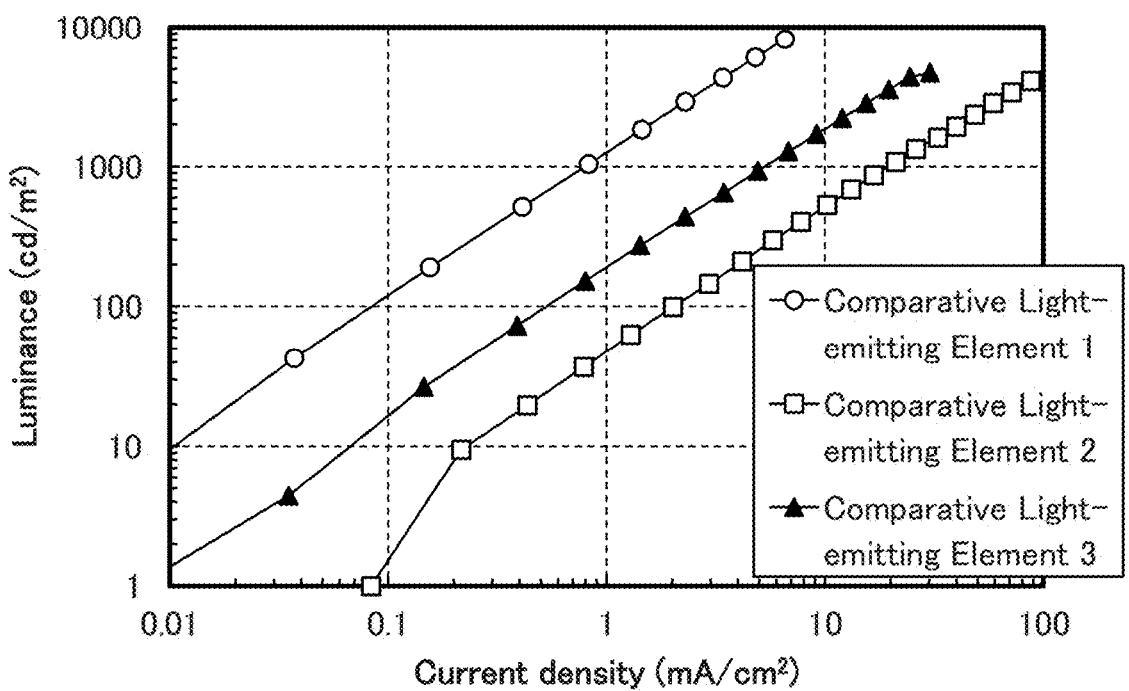
FIG. 21 shows luminance-current density characteristics of Comparative Light-emitting Elements 1 to 3.
Figure 22:
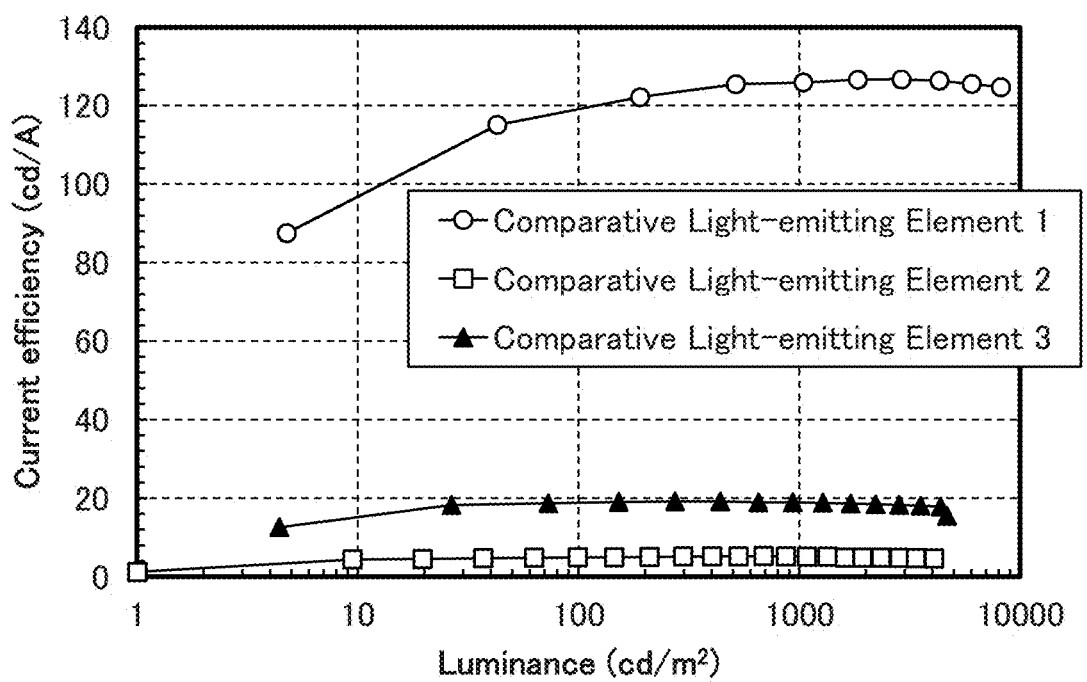
FIG. 22 shows current efficiency-luminance characteristics of Comparative Light-emitting Elements 1 to 3.
Figure 23:
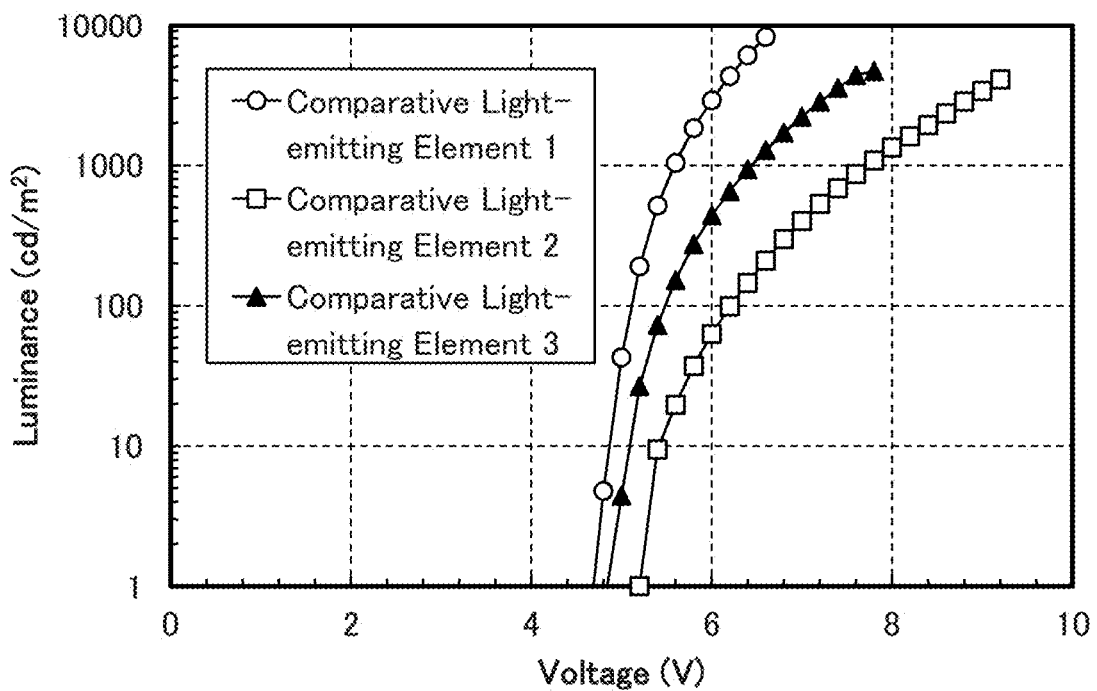
FIG. 23 shows luminance-voltage characteristics of Comparative Light-emitting Elements 1 to 3.
Figure 24:
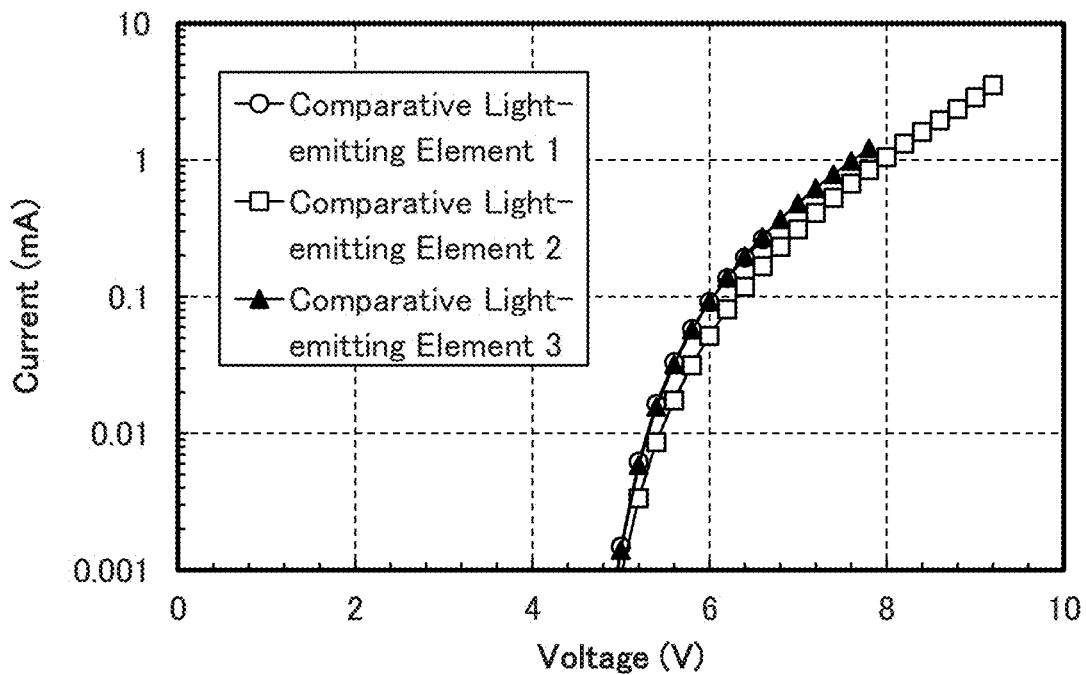
FIG. 24 shows current-voltage characteristics of Comparative Light-emitting Elements 1 to 3.
Figure 25:
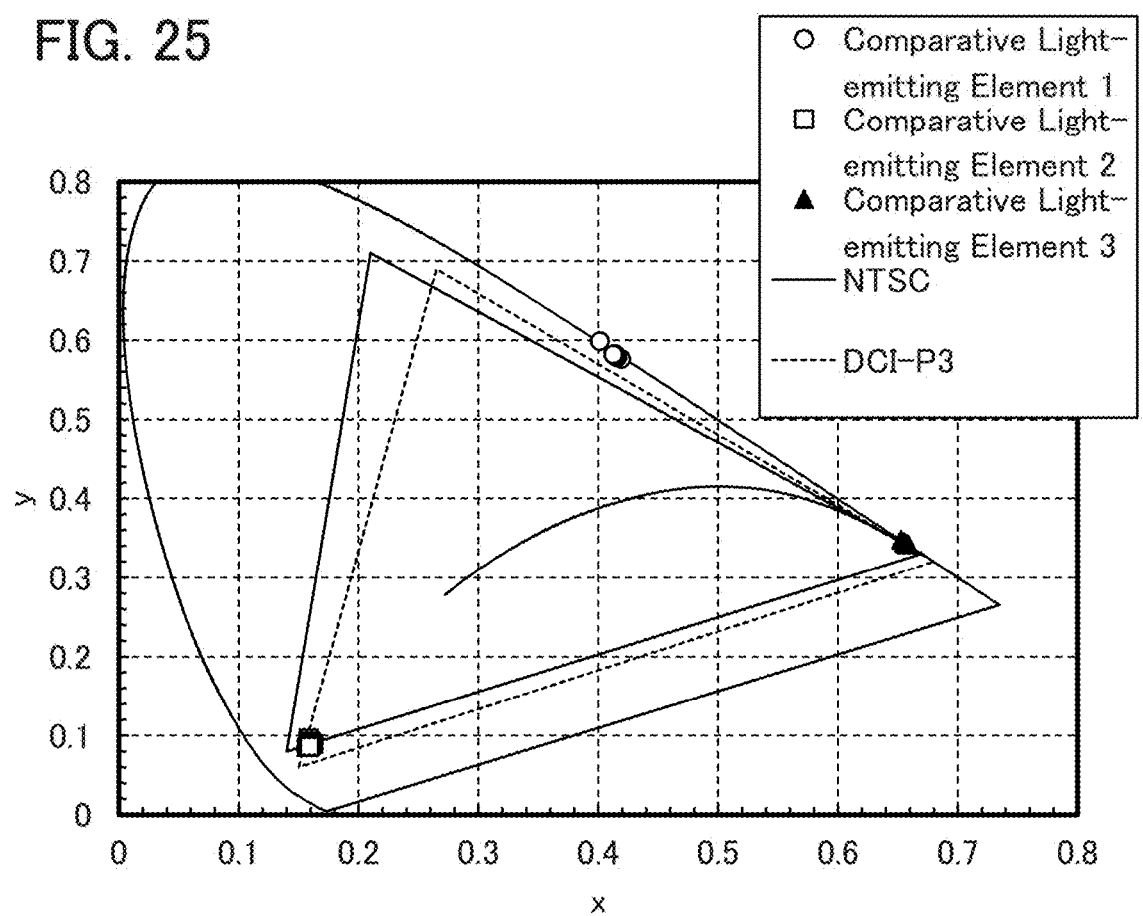
FIG. 25 shows chromaticity coordinates of Comparative Light-emitting Elements 1 to 3.

FIG. 21 shows luminance-current density characteristics of Comparative Light-emitting Elements 1 to 3, FIG. 22 shows current efficiency-luminance characteristics thereof, FIG. 23 shows luminance-voltage characteristics thereof, FIG. 24 shows current-voltage characteristics thereof, and FIG. 25 shows chromaticity coordinates thereof.

As in FIG. 20 and FIG. 25, Light-emitting Element 2 including 1,6BnfAPrn-03 has chromaticity coordinates of (x, y)=(0.152, 0.037) at around 1000 cd/m$^2$, and Comparative Light-emitting Element 2 including 1,6mMemFLPAPrn has chromaticity coordinates of (x, y)=(0.160, 0.087). This shows that Light-emitting Elements 2 exhibits deeper blue emission than Comparative Light-emitting Element 2.

Figure 26:
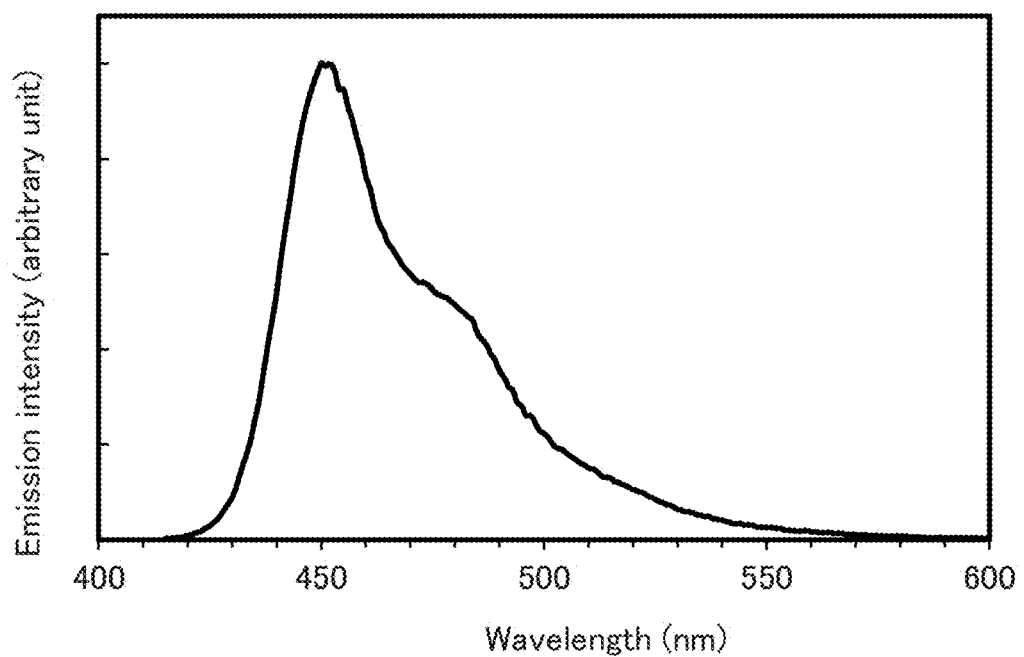
FIG. 26 shows an emission spectrum of 1,6BnfAPrn-03 in a toluene solution of 1,6BnfAPrn-03.

FIG. 26 shows the emission spectrum of 1,6BnfAPrn-03 in a toluene solution of 1,6BnfAPrn-03. As seen from FIG. 26, the peak wavelength of the emission spectrum of 1,6BnfAPrn-03 in the toluene solution was 450 nm. The half-width of the emission spectrum was 40 nm. On the other hand, the peak wavelength of 1,6mMemFLPAPrn in the toluene solution used for the comparative light-emitting elements was 461 nm.

Next, power consumption for obtaining white light having chromaticity at approximately D65 of the light-emitting devices including the light-emitting elements was calculated. The power consumption of the light-emitting devices was calculated under the following conditions.

TABLE 2

| Panel Size | 4.3 (inch) |
| --- | --- |
| | (Aspect Ratio 16:9) |
| Panel Area | 51.0 (cm$^2$) |
| Aperture Ratio | 35% |
| All White (Effective Luminance) | 300 (cd/m$^2$) |

Table 3 shows the calculation results of the light-emitting device of this example, and Table 4 shows the calculation results of the light-emitting device of the comparative example.

TABLE 3

| Light-emitting Element | Chromaticity x | Chromaticity y | Effective Luminance (cd/m$^2$) | Intrinsic Luminance (cd/m$^2$) | Current Efficiency (cd/A) |
| --- | --- | --- | --- | --- | --- |
| 1(Yellow) | 0.449 | 0.545 | 253 | 2895 | 142.6 |
| 2(Blue) | 0.152 | 0.038 | 15 | 175 | 2.3 |
| 3(Green) | 0.336 | 0.653 | 31 | 358 | 38.7 |
| All White | 0.313 | 0.329 | 300 | — | — |
| | | | | | Continued on *8 |

TABLE 3-continued

| Current Density (mA/cm$^2$) | Current Amount (mA) | Voltage (V) | Power Consumption (mW) |
| --- | --- | --- | --- |
| 2.0 | 9.1 | 5.92 | 53.6 |
| 7.7 | 34.4 | 6.38 | 219.2 |
| 0.9 | 4.1 | 5.50 | 22.7 |
| — | 47.5 | — | 295.6 |
| *8 | | | |

TABLE 4

| Comparative Light-emitting Element | Chromaticity x | Chromaticity y | Effective Luminance (cd/m$^2$) | Intrinsic Luminance (cd/m$^2$) | Current Efficiency (cd/A) |
| --- | --- | --- | --- | --- | --- |
| 1(Yellow) | 0.414 | 0.582 | 237 | 2705 | 126.7 |
| 2(Blue) | 0.160 | 0.088 | 38 | 435 | 5.2 |
| 3(Red) | 0.656 | 0.344 | 25 | 289 | 19.1 |
| All White | 0.313 | 0.329 | 300 | — | — |
| | | | | | Continued on *9 |

| Current Density (mA/cm$^2$) | Current Amount (mA) | Voltage (V) | Power Consumption (mW) |
| --- | --- | --- | --- |
| 2.1 | 9.5 | 5.96 | 56.8 |
| 8.4 | 37.5 | 7.05 | 264.3 |
| 1.5 | 6.7 | 5.82 | 39.1 |
| — | 53.7 | — | 360.2 |
| *9 | | | |

In the above calculation results, the effective luminance was obtained from the calculation of intrinsic luminance×aperture ratio×1/4 (the area ratio of each subpixel (assuming that one pixel includes four subpixels of red, green, blue, and yellow in the light-emitting devices)); the current amount was obtained from the calculation of current density×panel area×aperture ratio×1/4 (the area ratio of each subpixel); and the power consumption of a display portion was obtained from the calculation of current amount×voltage.

As seen from Table 3 and Table 4, the luminance of blue emission (emission of Light-emitting Element 2) needed for obtaining white light having chromaticity at approximately D65 of the light-emitting device of this example was as low as 15 cd/m$^2$, whereas the luminance of blue emission (emission of Comparative Light-emitting Element 2) needed for obtaining white light having chromaticity at approximately D65 of the light-emitting device of the comparative example was 38 cd/m$^2$. This is because the chromaticity of blue emission was improved by using, as a blue emission material, 1,6BnfAPrn-03 that is such a fluorescent substance as is described in Embodiment 1 and Embodiment 2, and thus the effective luminance of the blue emission needed for white light was reduced. Accordingly, the power consumption of Light-emitting Element 2 needed for obtaining white light was significantly reduced.

The power consumption of Light-emitting Element 3 needed for obtaining white light having chromaticity at approximately D65 was as low as 22.7 mW, whereas the power consumption of Comparative Light-emitting Element 3 needed for obtaining white light having chromaticity at approximately D65 was 39.1 mW. This also shows that the power consumption of the light-emitting device of this example is lower.

The reason for this is as follows: deep blue emission was obtained from Light-emitting Element 2, and thus the color of emission obtained by synthesis of the blue emission and yellow emission of Light-emitting Element 1 was changed and the color of third emission needed for obtaining white light having chromaticity at approximately D65 was changed. In the light-emitting device of this example, green emission was needed as the third emission. On the other hand, in the light-emitting device of the comparative example, red emission was needed as the third emission. The proportion of luminance needed for the green emission of the light-emitting device of this example for obtaining the white light is higher than that for the red emission of the light-emitting device of the comparative example for obtaining the white light.

However, the luminosity factor of the green emission is higher than that of the red emission, and thus the current efficiency of Light-emitting Element 3 that exhibits the green emission is about twice as high as that of Comparative Light-emitting Element 3 that exhibits the red emission. Therefore, even in the case where the proportion of luminance of the third emission (emission of Light-emitting Element 3) needed for obtaining the white light in the light-emitting device of this example is increased, the power consumption of Light-emitting Element 3 can be lower than that of Comparative Light-emitting Element 3.

The effective luminance of Light-emitting Element 2 (blue) and that of Light-emitting Element 3 (green) needed for obtaining white light having chromaticity at approximately D65 with a luminance of 300 cd/m² in the light-emitting element of this example are respectively lower than that of Comparative Light-emitting Element 2 (blue) and that of Comparative Light-emitting Element 3 (red) needed for obtaining white light having chromaticity at approximately D65 with a luminance of 300 cd/m² in the light-emitting element of the comparative example; however, the shortfall can be compensated for by high luminance of yellow emission of Light-emitting Element 1. Since the current efficiency of Light-emitting Element 1 that exhibits yellow emission is significantly high, an increase in power consumption due to the increase in needed luminance can be canceled by a decrease in the luminance needed for Light-emitting Element 2 and Light-emitting Element 3. Consequently, a reduction in power consumption of the light-emitting device of this example can be achieved.

As a result, the power consumption of the light-emitting device of this example that performs white display except the power consumption of driving FETs was 5.8 mW/cm², and that including the power consumption of the driving FETs was 14 mW/cm². Since the power consumption of the light-emitting device of the comparative example that performs white display except the power consumption of the driving FETs was 7.1 mW/cm², and that including the power consumption of the driving FETs was 16 mW/cm², the power consumption of the light-emitting device of this example can be lower than that of the comparative example by about 10% to 20%. Note that the power consumption of the light-emitting devices with driving FETs was estimated with a voltage between an anode and a cathode (the sum of voltages of portions of the light-emitting elements and the driving FETs) of 15 V Since the blue light-emitting element consumes much higher power than the light-emitting elements of the other colors, an effect of a reduction in power consumption due to a change in chromaticity is considerable. Furthermore, a reduction in power consumption can be achieved owing to a change in balance relating to the emission colors for obtaining white light having chromaticity at approximately D65 and the proportions of the luminances. As a result, the power consumption of the light-emitting device of this example which includes such a fluorescent substance as is described in Embodiment 1 can be low.

Example 2

In this example, results of calculating power consumption of light-emitting devices performing white display will be described. In the light-emitting device of the present invention, light-emitting elements (a red light-emitting element: Light-emitting Element 4, a yellow light-emitting element: Light-emitting Element 5, a green light-emitting element: Light-emitting Element 6, and a blue light-emitting element: Light-emitting Element 7) are used. In the light-emitting device of a comparative example, light-emitting elements (a red light-emitting element: Comparative Light-emitting Element 4, a green light-emitting element: Comparative Light-emitting Element 5, and a blue light-emitting element: Comparative Light-emitting Element 6) are used.

Structure formulae of organic compounds used in Light-emitting Elements 4 to 7 and Comparative Light-emitting Elements 4 to 6 are shown below.

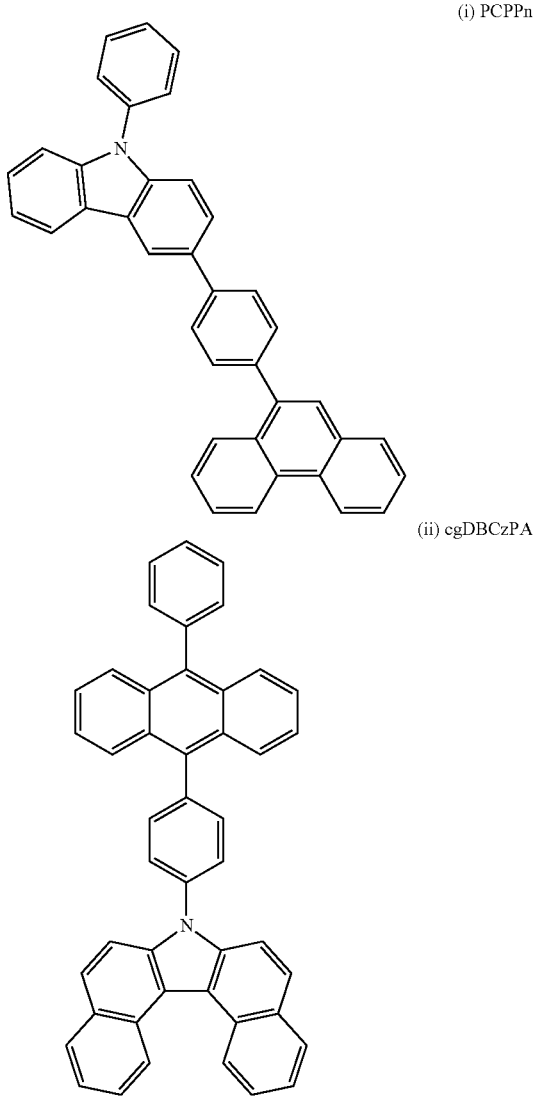

(i) PCPPn (ii) cgDBCzPA (iii) 1,6BnfAPrn-03
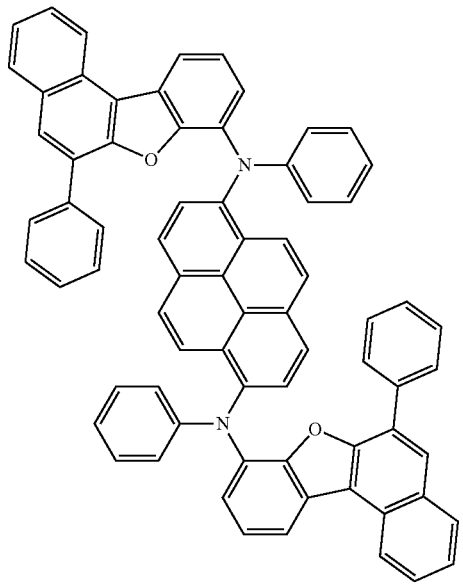
(iv) BPhen
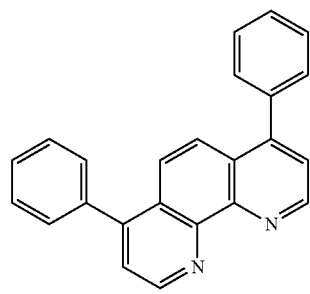
(v) DBT3P-II
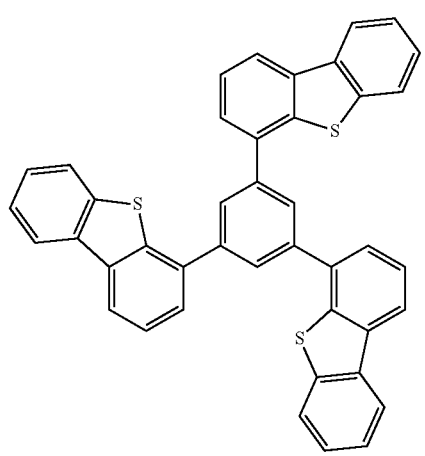
(vii) 2mDBTBPDBq-II
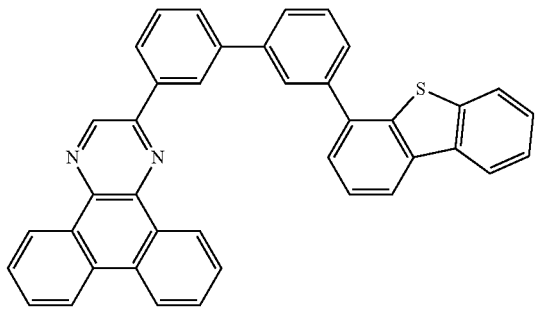
(vii) BPAFLP
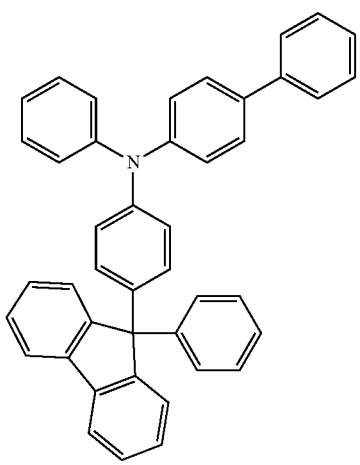
(viii) PCBBiF
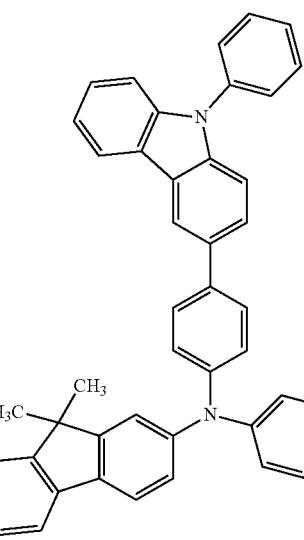

-continued

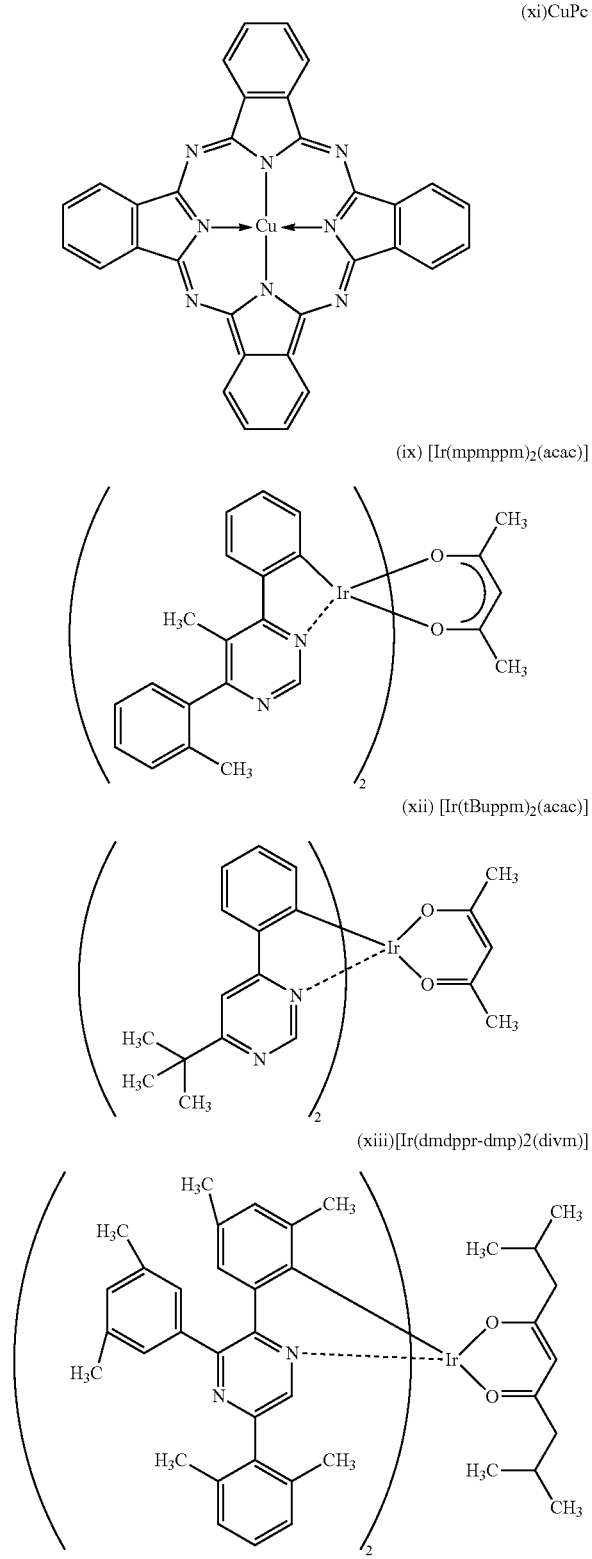

(xi) CuPc (ix) [Ir(mpmppm)₂(acac)]

(xii) [Ir(tBuppm)₂(acac)]

(xiii)[Ir(dmdppr-dmp)2(divm)]

(Methods for Fabricating Light-Emitting Elements 4 to 7 and Comparative Light-Emitting Elements 4 to 6)

First, an alloy film of silver (Ag), palladium (Pd), nd copper (Cu)(the alloy film is hereinafter referred to as APC) was formed over a glass substrate by a sputtering method to form a first electrode (reflective electrode). The thickness of the first electrode was 100 nm and the electrode area was 2 mm×2 mm.

Next, as a transparent conductive film, a film of indium tin oxide containing silicon oxide was formed over the first electrode by a sputtering method. The thickness of the transparent conductive film for Light-emitting Element 4 (red) was 80 nm, that for Light-emitting Element 5 (yellow) was 45 nm, that for Light-emitting Element 6 (green) was 45 nm, and that for Light-emitting Element 7 (blue) was 80 nm. The thickness of the transparent conductive film for Comparative Light-emitting Element 4 (red) was 85 nm, that for Comparative Light-emitting Element 5 (green) was 45 nm, and that for Comparative Light-emitting Element 6 (blue) was 110 nm.

Then, as pretreatment of evaporation of an organic compound layer, a surface of the substrate provided with the reflective electrode and the transparent conductive film was washed with water, baking was performed at 200° C. for one hour, and then UV ozone treatment was performed for 370 seconds.

After that, the substrate was transferred into a vacuum evaporation apparatus in which the pressure had been reduced to approximately $10^{-4}$ Pa, and was subjected to vacuum baking at 170° C. for 30 minutes in a heating chamber of the vacuum evaporation apparatus, and then the substrate was cooled down for about 30 minutes.

Then, the substrate was fixed to a substrate holder provided in the vacuum evaporation apparatus so that the surface on which the transparent conductive film was formed faced downward. The pressure in the vacuum evaporation apparatus was reduced to approximately $10^{-4}$ Pa. After that, on the transparent conductive film, 3-[4-(9-phenanthryl)-phenyl]-9-phenyl-9H-carbazole (abbreviation: PCPPn) represented by Structural Formula (i) and molybdenum(VI) oxide were deposited by co-evaporation using resistance heating, whereby a first hole-injection layer was formed. The thickness of the first hole-injection layer for Light-emitting Element 4 (red) was 30 nm, that for Light-emitting Element 5 (yellow) was 40 nm, that for Light-emitting Element 6 (green) was 22.5 nm, and that for Light-emitting Element 7 (blue) was 50 nm. The thickness of the first hole-injection layer for Comparative Light-emitting Element 4 (red) was 10 nm, that for Comparative Light-emitting Element 5 (green) was 10 nm, and that for Comparative Light-emitting Element 6 (blue) was 15 nm. The weight ratio of PCPPn to molybdenum oxide was adjusted to 1:0.5.

Next, on the first hole-injection layer, PCPPn was deposited to form a first hole-transport layer. The thickness of the first hole-transport layer for each of Light-emitting Elements 4 to 7 was 10 nm, and the thickness of the first hole-transport layer for each of Comparative Light-emitting Elements 4 to 6 was 15 nm.

On the first hole-transport layer, a first light-emitting layer was formed by deposition of 7-[4-(10-phenyl-9-anthryl)phenyl]-7H-dibenzo[c,g]carbazole (abbreviation: cgDBCzPA) represented by Structural Formula (ii) and N,N-(pyrene-1,6-diyl)bis[(6,N-diphenylbenzo[b]naphtho[1,2-d]furan)-8-amine] (abbreviation: 1,6BnfAPrn-03) represented by Structural Formula (iii) to a thickness of 25 nm so that the weight ratio of cgDBCzPA to 1,6BnfAPrn-03 was 1:0.05.

Then, a first electron-transport layer was formed over the first light-emitting layer in such a way that cgDBCzPA was deposited to a thickness of 5 nm and bathophenanthroline (abbreviation: BPhen) represented by Structural Formula (iv) was deposited to a thickness of 15 nm.

After the first electron-transport layer was formed, lithium oxide (Li$_2$O) was evaporated to a thickness of 0.1 nm. Then, copper phthalocyanine (abbreviation: CuPc) represented by Structural Formula (xi) was evaporated to a thickness or 2 nm. After that, 4,4',4''-(benzene-1,3,5-triyl)tri(dibenzothiophene) (abbreviation: DBT3P-II) represented by Structural Formula (v) and molybdenum oxide were co-evaporated so that the weight ratio of DBT3P-II to molybdenum oxide was 1:0.5. In such a manner, an intermediate layer was formed. The thickness of the intermediate layer was 12.5 nm.

Next, on the intermediate layer, 4-phenyl-4'-(9-phenylfluoren-9-yl)triphenylamine (abbreviation: BPAFLP) represented by Structural Formula (vi) was evaporated to a thickness of 20 nm, whereby a second hole-transport layer was formed.

As for each of Light-emitting Elements 4 to 7, after the second hole-transport layer was formed, 2-[3'-(dibenzothiophen-4-yl)biphenyl-3-yl]dibenzo[f,h]quinoxaline (abbreviation: 2mDBTBPDBq-II) represented by Structural Formula (vii), N-(1,1'-biphenyl-4-yl)-9,9-dimethyl-N-[4-(9-phenyl-9H-carbazol-3-yl)phenyl]-9H-fluoren-2-amine (abbreviation: PCBBiF) represented by Structural Formula (viii), and bis{2-[5-methyl-6-(2-methylphenyl)-4-pyrimidinyl-κN3]phenyl-κC}(2,4-pentanedionato-κ$^2$O,O')iridium (III) (abbreviation: [Ir(mpmppm)$_2$(acac)]) represented by Structural Formula (ix) were co-evaporated so that the weight ratio of 2mDBTBPDBq-II to PCBBiF and [Ir(mpmppm)$_2$(acac)] was 0.8:0.2:0.06. In this manner, a second light-emitting layer was formed. The thickness of the second light-emitting layer was 40 nm.

As for each of Comparative Light-emitting Elements 4 to 6, after the second hole-transport layer was formed, 2mDBTBPDBq-II, PCBBiF, and bis[2-(6-tert-butyl-4-pyrimidinyl-κN3)phenyl-κC](2,4-pentanedionato-κ$^2$O,O') iridium(III) (abbreviation: [Ir(tBuppm)$_2$(acac)]) represented by Structural Formula (xii) were co-evaporated to a thickness of 20 nm. After that, 2mDBTBPDBq-II and bis{4,6-dimethyl-2-[5-(2,6-dimethylphenyl)-3-(3,5-dimethylphenyl)-2-pyrazinyl-κN]phenyl-κC}(2,8-dimethyl-4,6-nonanedionato-κ$^2$O,O')iridium(III) (abbreviation: [Ir(dmdppr-dmp)$_2$(divm)]) were co-evaporated to a thickness of 20 nm so that the weight ratio of 2mDBTBPDBq-II to [Ir(dmdppr-dmp)$_2$(divm)] was 1:0.06. In this manner, a second light-emitting layer was formed.

As for each of Light-emitting Elements 4 to 7, on the second light-emitting layer, 2mDBTBPDBq-II was evaporated to a thickness of 15 nm. As for each of Comparative Light-emitting Elements 4 to 6, on the second light-emitting layer, 2mDBTBPDBq-II was evaporated to a thickness of 30 nm. As for each of Light-emitting Elements 4 to 7, on 2mDBTBPDBq-II, BPhen was also evaporated to a thickness of 20 nm. As for each of Comparative Light-emitting Elements 4 to 6, on 2mDBTBPDBq-II, BPhen was also evaporated to a thickness of 15 nm. In this manner, a second electron-transport layer was formed.

After that, lithium fluoride was evaporated to a thickness of 1 nm to form an electron-injection layer. Then, silver and magnesium were co-evaporated to a thickness of 15 nm with a volume ratio of 1:0.1 (=silver:magnesium). Next, ITO was deposited to a thickness of 70 nm by a sputtering method. In this manner, a second electrode (semi-transmissive and semi-reflective electrode) was formed. Through the above steps, Light-emitting Elements 4 to 7 and Comparative Light-emitting Elements 4 to 6 were fabricated. Note that in all the above evaporation steps, evaporation was performed by a resistance-heating method.

The element structures of Light-emitting Elements 4 to 7 and Comparative Light-emitting Elements 4 to 6 are listed below.

TABLE 5

| Reflective Electrode | | Hole-injection Layer | First Hole-transport Layer | First Light-emitting Layer | First Electron-transport Layer | |
|---|---|---|---|---|---|---|
| APC | ITSO | PCPPn:MoOx 1:0.5 | PCPPn | cgDBCzPA:1,6BnfAPrn-03 1:0.05 | cgDBCzPA | BPhen |
| 100 nm | *10 | *11 | *12 | 25 nm | 5 nm | 15 nm |
| | | | | | | Continued on *17 |

| | Intermediate Layer | | | Second Hole-transport Layer | Second Light-emitting Layer | Second Electron-transport Layer | |
|---|---|---|---|---|---|---|---|
| Li$_2$O | CuPC | DBT3P-II:MoOx 1:0.5 | | BPAFLP | *13 | 2mDBTBPDBq-II | BPhen |
| 0.1 nm | 2 nm | 12.5 nm | | 20 nm | | *14 | *15 |
| *17 | | | | | | | Continued on *18 |

| Electron-injection Layer | Semi-transmissive and Semi-reflective Electrode | | Color Filter |
|---|---|---|---|
| LiF | Ag:Mg 1:0.1 | ITO | *16 |

TABLE 5-continued

| | 1 nm | 15 nm | 70 nm |
|---|---|---|---|
| *18 | | | |

*10 Light-emitting Element 4: 80 nm, Light-emitting Element 5: 45 nm, Light-emitting Element 6: 45 nm, Light-emitting Element 7: 80 nm
Comparative Light-emitting Element 4: 85 nm, Comparative Light-emitting Element 5: 45 nm, Comparative Light-emitting Element 6: 110 nm
*11 Light-emitting Element 4: 30 nm, Light-emitting Element 5: 40 nm, Light-emitting Element 6: 22.5 nm, Light-emitting Element 7: 50 nm
Comparative Light-emitting Element 4: 10 nm, Comparative Light-emitting Element 5: 10 nm, Comparative Light-emitting Element 6: 15 nm
*12 Light-emitting Elements 4 to 7: 10 nm, Comparative Light-emitting Elements 4 to 6: 15 nm
*13 Light-emitting Elements 4 to 7
2mDBTBPDBq-II:PCBBiF:[Ir(mpmppm)$_2$(acac)] = 0.8:0.2:0.06, 40 nm
Comparative Light-emitting Elements 4 to 6
2mDBTBPDBq-II:PCBBiF:[Ir(tBuppm)$_2$(acac)] = 0.7:0.3:0.06, 20 nm + 2mDBTBPDBq-II:[Ir(dmdppr-dmp)$_2$(divm)] = 1:0.06, 20 nm
*14 Light-emitting Elements 4 to 7: 15 nm, Comparative Light-emitting Elements 4 to 6: 30 nm
*15 Light-emitting Elements 4 to 7: 20 nm, Comparative Light-emitting Elements 4 to 6: 15 nm
*16 Light-emitting Element 4 and Comparative Light-emitting Element 4: Red 2.4 μm
Light-emitting Element 5: Yellow 0.8 μm
Light-emitting Element 6 and Comparative Light-emitting Element 5: Green 1.3 μm
Light-emitting Element 7 and Comparative Light-emitting Element 6: Blue 0.8 μm Each of Light-emitting Elements 4 to 7 and Comparative Light-emitting Elements 4 to 6 was sealed using a glass substrate in a glove box containing a nitrogen atmosphere so as not to be exposed to the air (specifically, a sealing material was applied to surround the element, and at the time of sealing, UV treatment (with 365-nm ultraviolet light at 6 J/cm$^2$) was performed and heat treatment was performed at 80° C. for 1 hour). Then, initial characteristics of these light-emitting elements were measured. Note that the measurement was carried out at room temperature (in an atmosphere kept at 25° C.).

Figure 28:
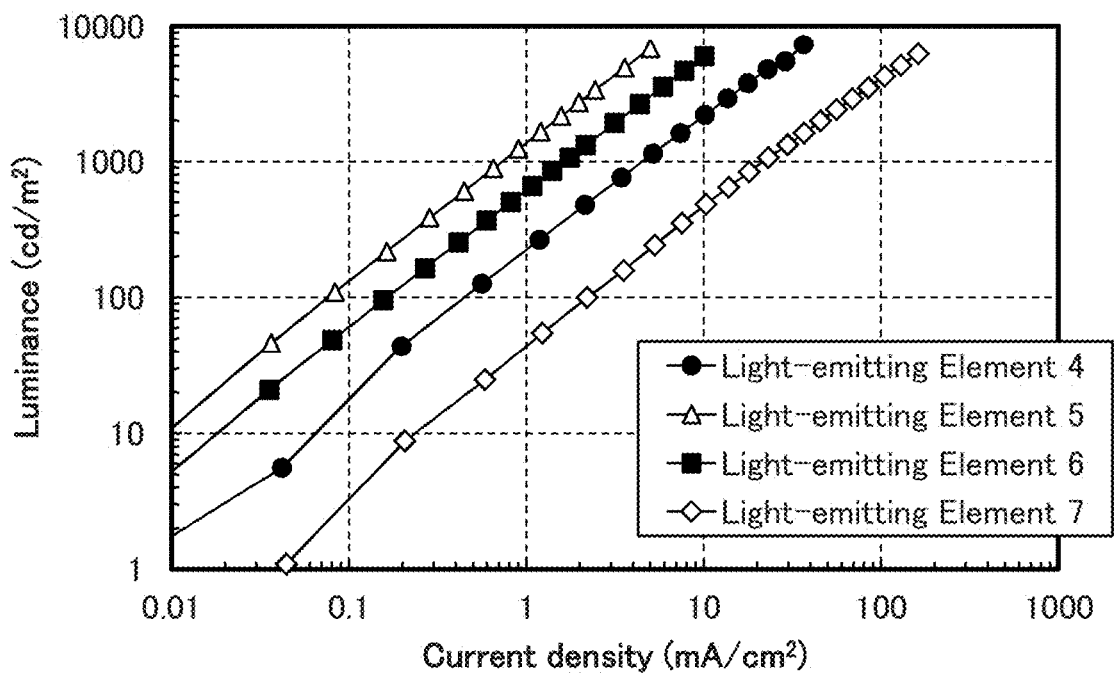
FIG. 28 shows luminance-current density characteristics of Light-emitting Elements 4 to 7.
Figure 29:
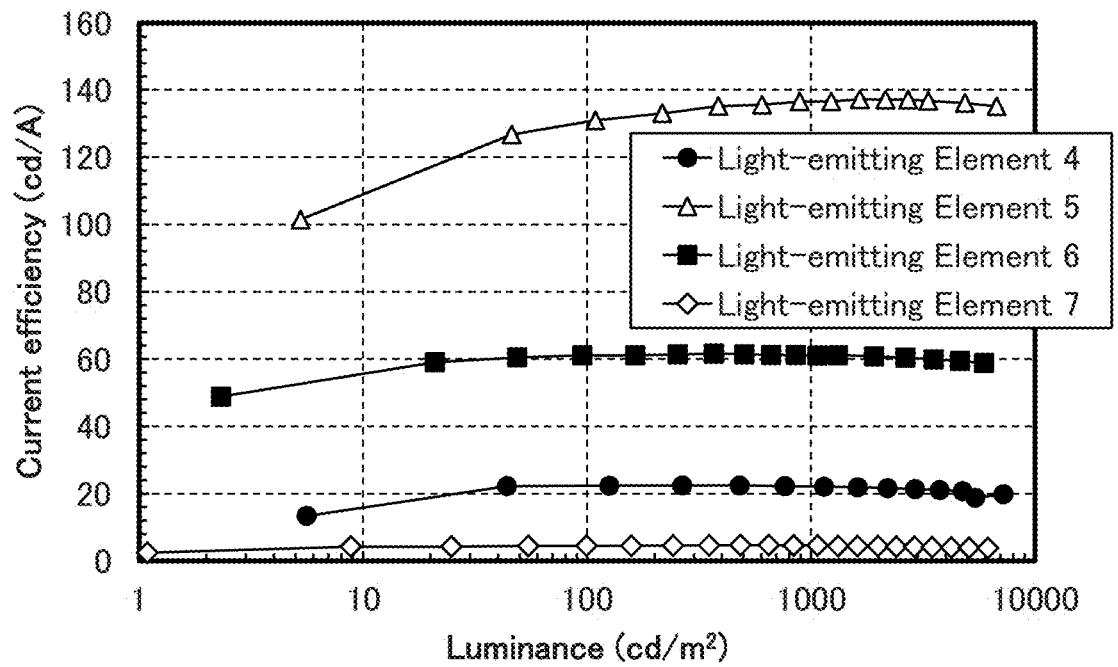
FIG. 29 shows current efficiency-luminance characteristics of Light-emitting Elements 4 to 7.
Figure 30:
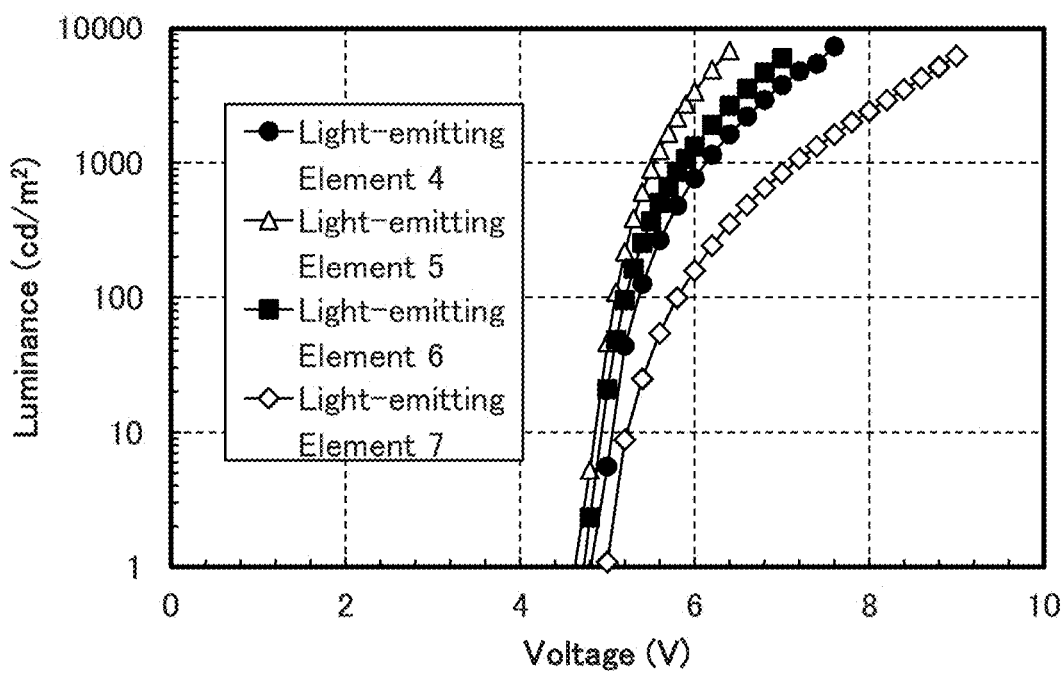
FIG. 30 shows luminance-voltage characteristics of Light-emitting Elements 4 to 7.
Figure 31:
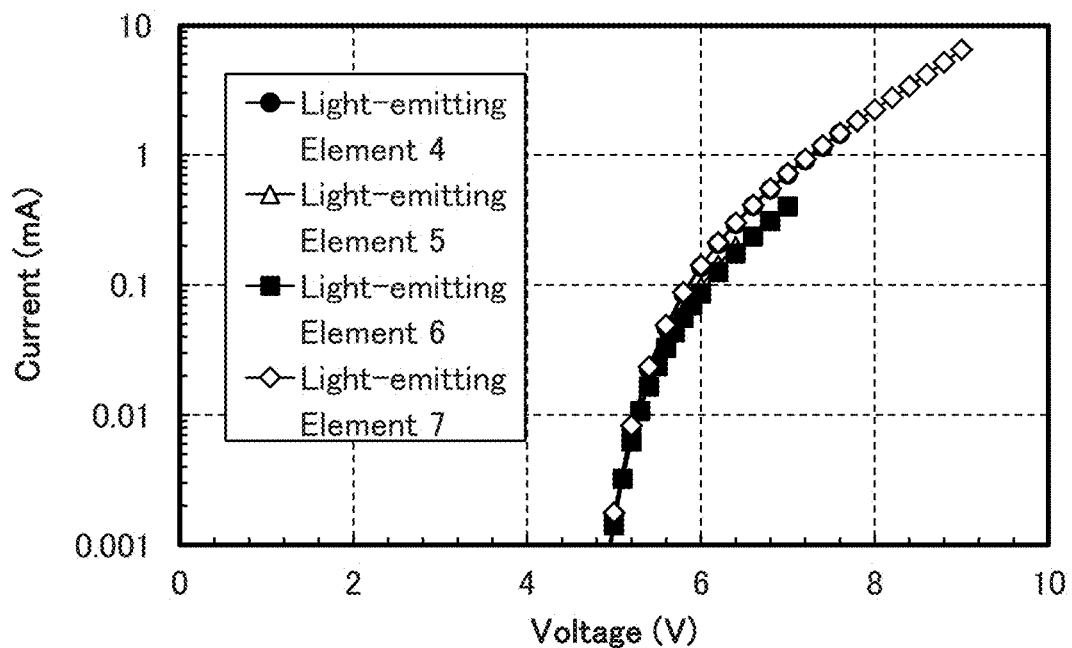
FIG. 31 shows current-voltage characteristics of Light-emitting Elements 4 to 7.
Figure 32:
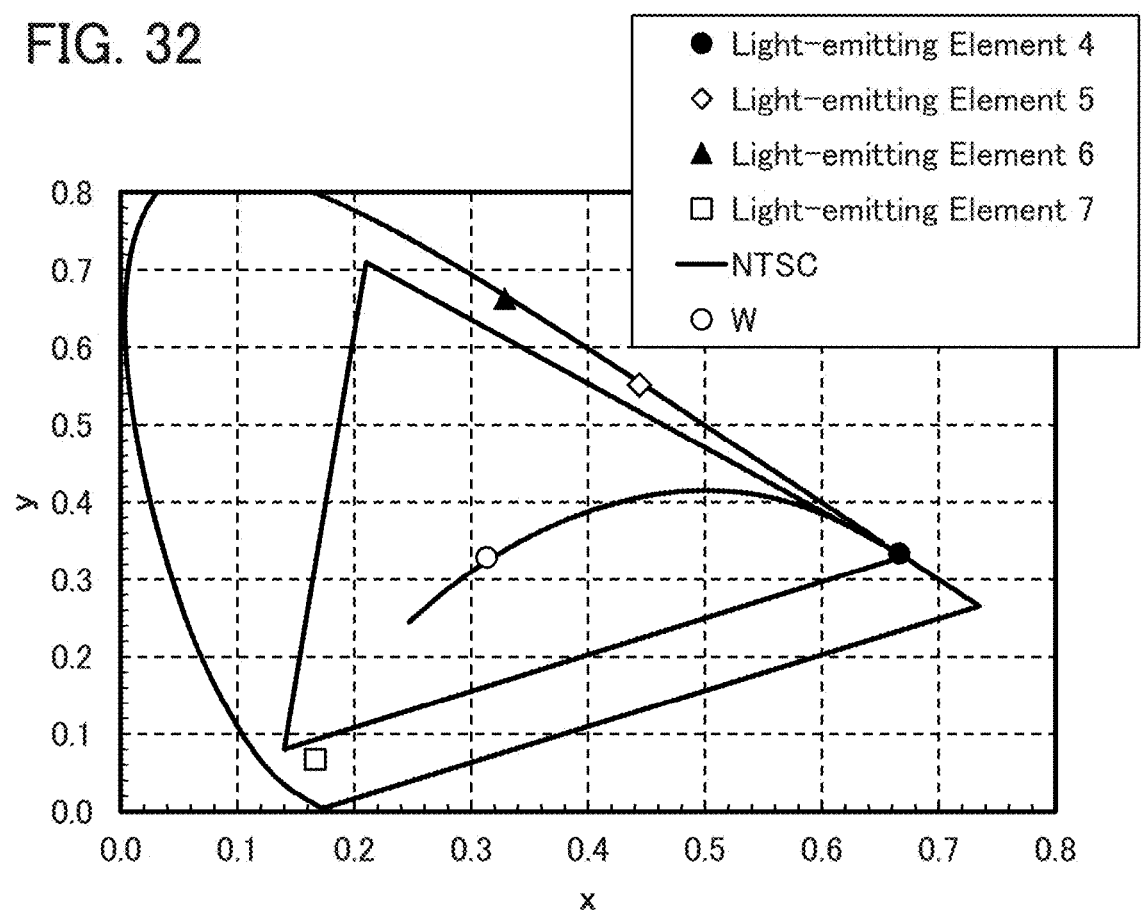
FIG. 32 shows chromaticity coordinates of Light-emitting Elements 4 to 7.

FIG. 28 shows luminance-current density characteristics of Light-emitting Elements 4 to 7, FIG. 29 shows current efficiency-luminance characteristics thereof, FIG. 30 shows luminance-voltage characteristics thereof, FIG. 31 shows current-voltage characteristics thereof, and FIG. 32 shows chromaticity coordinates thereof.

Figure 33:
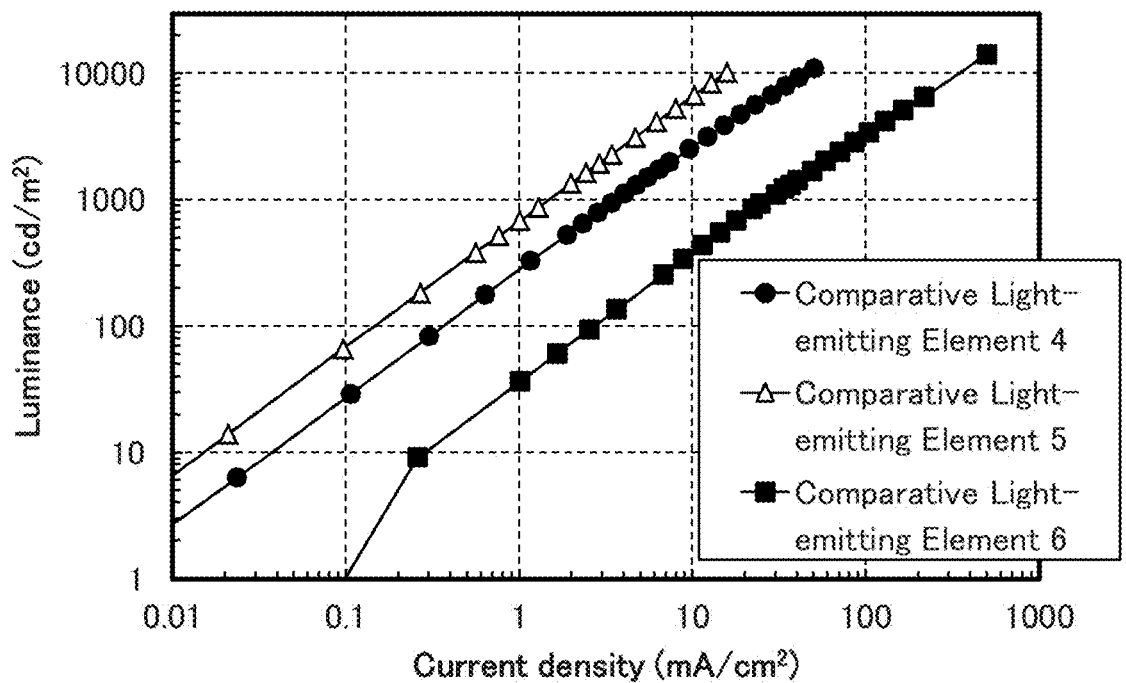
FIG. 33 shows luminance-current density characteristics of Comparative Light-emitting Elements 4 to 6.
Figure 34:
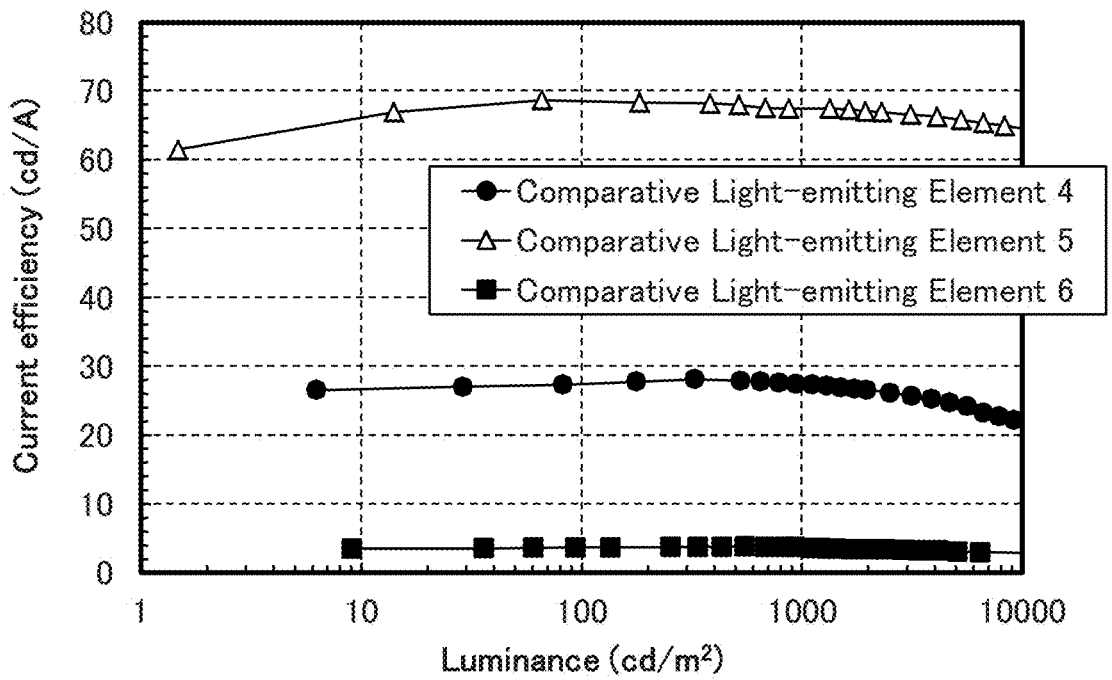
FIG. 34 shows current efficiency-luminance characteristics of Comparative Light-emitting Elements 4 to 6.
Figure 35:
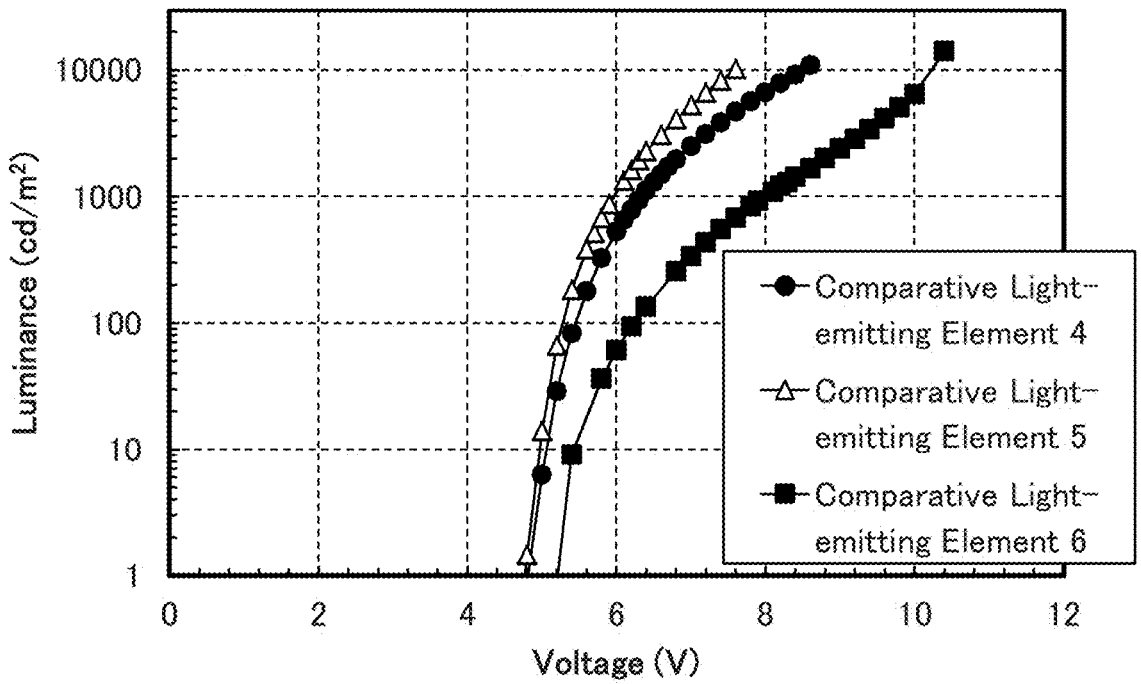
FIG. 35 shows luminance-voltage characteristics of Comparative Light-emitting Elements 4 to 6.
Figure 36:
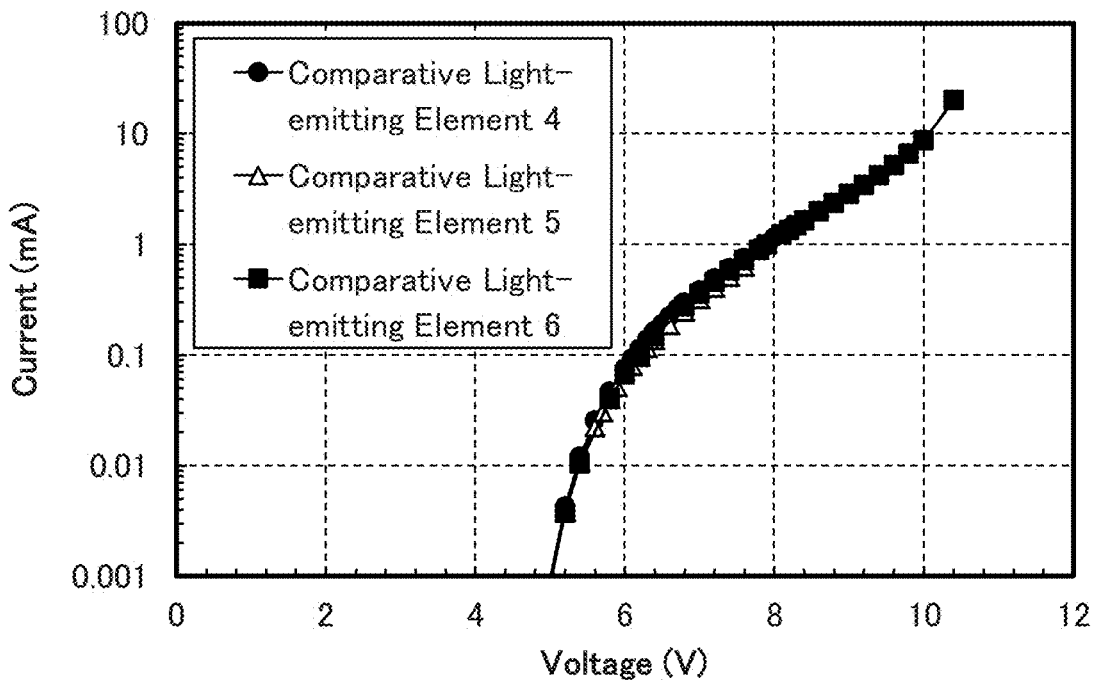
FIG. 36 shows current-voltage characteristics of Comparative Light-emitting Elements 4 to 6.

FIG. 33 shows luminance-current density characteristics of Comparative Light-emitting Elements 4 to 6, FIG. 34 shows current efficiency-luminance characteristics thereof, FIG. 35 shows luminance-voltage characteristics thereof, and FIG. 36 shows current-voltage characteristics thereof.

Next, power consumption for obtaining white light having chromaticity at approximately D65 of the light-emitting devices including the light-emitting elements was calculated. The power consumption of the light-emitting devices was calculated under the following conditions.

TABLE 6

| Panel Size | 4.3 (inch) |
|---|---|
| | (Aspect Ratio 16:9) |
| Panel Area | 51.0 (cm$^2$) |
| Aperture Ratio | 35% |
| All White (Effective Luminance) | 300 (cd/m$^2$) |

Table 7 shows the calculation results of the light-emitting device of this example, and Table 8 shows the calculation results of the light-emitting device of the comparative example.

TABLE 7

| Light-emitting Element | Voltage (V) | Current Density (mA/cm$^2$) | CIE Chromaticity (x, y) | Luminance (cd/m$^2$) | Current Efficiency (cd/A) | Power Consumption (mW) |
|---|---|---|---|---|---|---|
| 4 (Red) | — | &emdash | (0.67, 0.33) | — | 22.1 | 0 |
| 5 (Yellow) | 5.9 | 2.2 | (0.44, 0.55) | 2956 | 137 | 57.2 |
| 6 (Green) | 5.3 | 0.23 | (0.33, 0.66) | 139 | 61.1 | 5.3 |
| 7 (Blue) | 6.4 | 7.2 | (0.17, 0.07) | 334 | 4.66 | 203.7 |

TABLE 8

| Comparative Light-emitting Element | Voltage (V) | Current Density (mA/cm$^2$) | CIE Chromaticity (x, y) | Intrinsic Luminance (cd/m$^2$) | Current Efficiency (cd/A) | Power Consumption (mW) |
|---|---|---|---|---|---|---|
| 4 (Red) | 6.0 | 2.1 | (0.67, 0.33) | 572 | 27.8 | 73.7 |
| 5 (Green) | 6.3 | 2.7 | (0.29, 0.70) | 1792 | 67.2 | 99.2 |
| 6 (Blue) | 6.6 | 5.6 | (0.16, 0.06) | 208 | 3.72 | 221.1 |

In the above calculation results, the effective luminance was obtained from the calculation of intrinsic luminance×aperture ratio×1/4 (the area ratio of each subpixel (assuming that one pixel includes four subpixels of red, green, blue, and yellow in the light-emitting devices)); the current amount was obtained from the calculation of current density×panel area×aperture ratio×1/4 (the area ratio of each subpixel); and the power consumption of a display portion was obtained from the calculation of current amount×voltage.

As seen from Table 7 and Table 8, the power consumption for obtaining white light of the light-emitting device of this example was 266 mW, and that of the light-emitting device of the comparative example was 394 mW; thus, the light-emitting device of this example consumes lower power than that of the comparative example. In the light-emitting device of the comparative example, both Comparative Light-emitting Element 4 (red) and Comparative Light-emitting Element 5 (green) need intrinsic luminance to account for certain proportions for emitting white light. On the other hand, in the light-emitting device of this example, Light-emitting Element 4 (red) emits no light and the emission luminance of Light-emitting Element 6 (green) is as low as 139 cd/m$^2$ for emitting white light; thus, they do not substantially affect the power consumption. That is, in the light-emitting device of this example, only Light-emitting Element 7 (blue) and Light-emitting Element 5 (yellow) emit light substantially for exhibiting white emission. Since the current efficiency of Light-emitting Element 5 (yellow) is as high as 137 cd/A, the power consumption of the light-emitting device of this example was significantly lower than that of the light-emitting device of the comparative example although the power consumption of the blue light-emitting elements of the light-emitting devices of this example and the comparative example are substantially the same.

Example 3

The estimated results of luminance degradation in the case where a light-emitting device of one embodiment of the present invention performs white display having chromaticity at approximately D65 with a luminance of 300 cd/m$^2$ are shown. In this example, driving tests on Light-emitting Element 8 (blue) and Light-emitting Element 9 (yellow) which have the same structure as a light-emitting element in the light-emitting device of one embodiment of the present invention were carried out under the condition where the current density was constant. The initial luminance of Light-emitting Element 8 was set to 300 cd/m$^2$, and that of Light-emitting Element 9 was set to 3000 cd/m$^2$. These values were close to luminance values needed for performing white display having chromaticity at approximately D65 in the light-emitting device of one embodiment of the present invention with the following conditions. The reason why the driving tests were carried out on the assumption that white display was performed is that light emission needs to be continuously performed for white display and thus the elements are degraded the most quickly in performing white display.

TABLE 9

| Panel Size | 4.3 (inch) |
|---|---|
| | (Aspect Ratio 16:9) |
| Panel Area | 51.0 (cm$^2$) |
| Aperture Ratio | 35% |
| All White (Effective Luminance) | 300 (cd/m$^2$) |

Note that the driving test was not carried out on a red light-emitting element or a green light-emitting element because light is extracted from a yellow light-emitting layer and thus they probably show degradation behaviors similar to those of a yellow light-emitting element and because the luminance needed for the red light-emitting element and the green light-emitting element in performing white display having chromaticity at approximately D65 is low as described in Example 2 and thus they do not affect reliability.

Structural formulae of organic compounds used in Light-emitting Elements 8 and 9 are shown below.

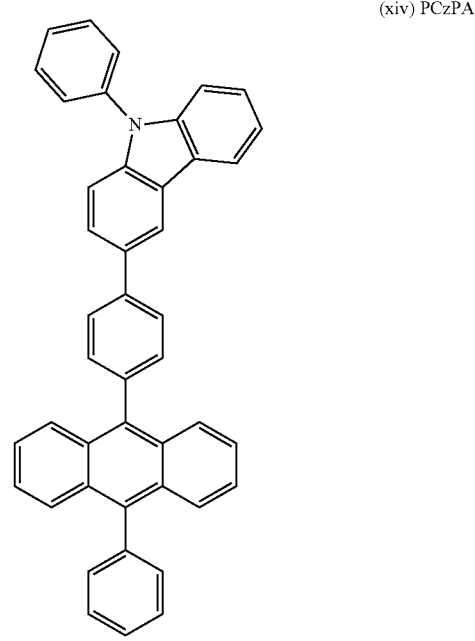

(xiv) PCzPA

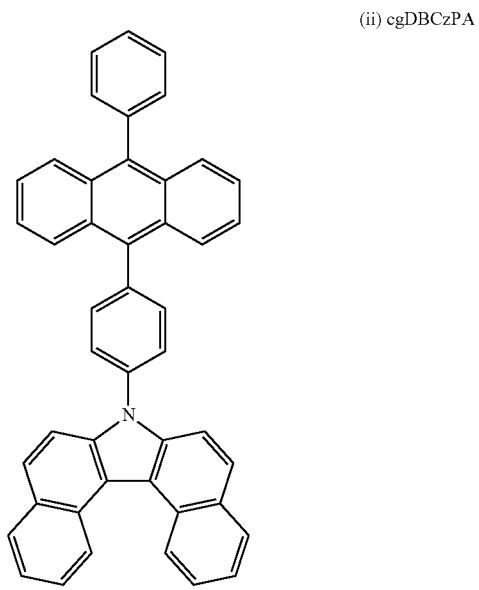

(ii) cgDBCzPA

-continued (iii) 1,6BnfAPrn-03

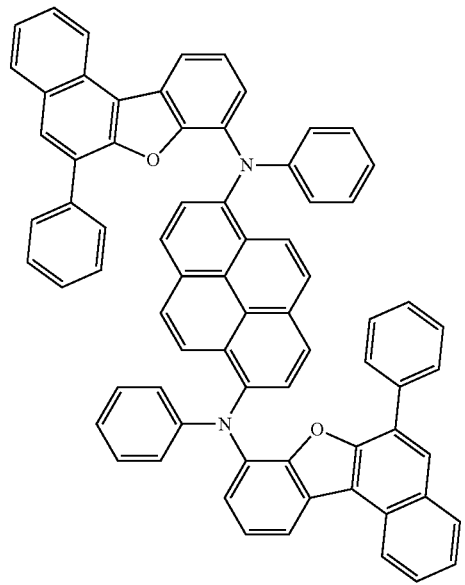

(iv) BPhen

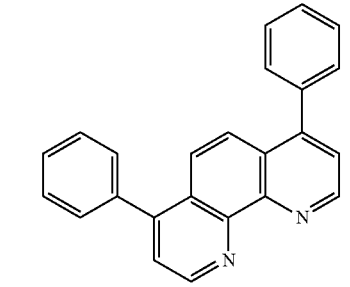

(vii) 2mDBTBPDBq-II

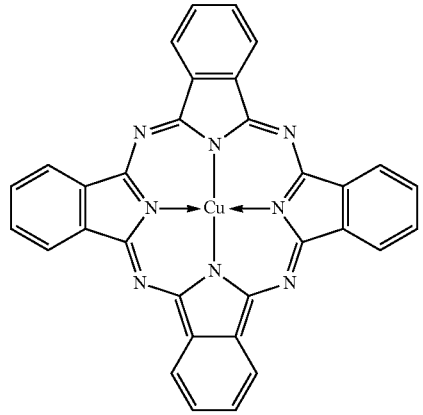

(xi) CuPc

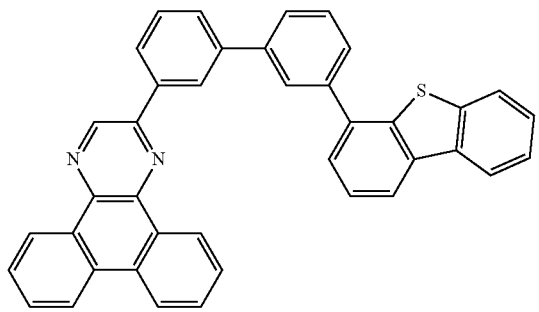

-continued (ix) [Ir(mpmppm)$_2$(acac)]

(viii) PCBBiF

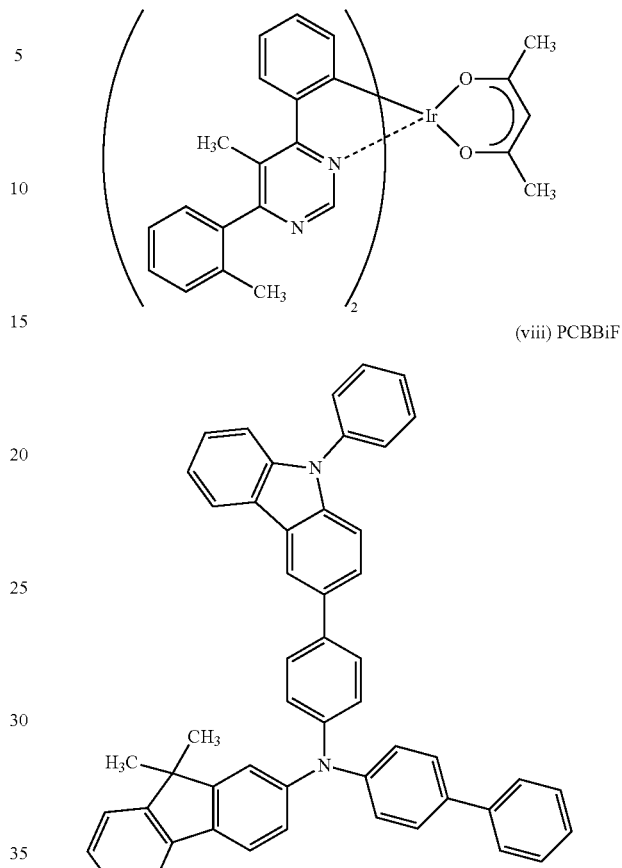

(Methods for Fabricating Light-Emitting Elements 8 and 9)

First, an alloy film of silver (Ag), palladium (Pd), and copper (Cu) (the alloy film is hereinafter referred to as APC) was formed over a glass substrate by a sputtering method to form a first electrode (reflective electrode). The thickness of the first electrode was 100 nm and the electrode area was 2 mm×2 mm.

Next, as a transparent conductive film, a film of indium tin oxide containing silicon oxide was formed over the first electrode by a sputtering method. The thickness of the transparent conductive film for Light-emitting Element 8 (blue) was 85 nm, and that for Light-emitting Element 9 (yellow) was 65 nm.

Then, as pretreatment of evaporation of an organic compound layer, a surface of the substrate provided with the reflective electrode and the transparent conductive film was washed with water, baking was performed at 200° C. for one hour, and then UV ozone treatment was performed for 370 seconds.

After that, the substrate was transferred into a vacuum evaporation apparatus in which the pressure had been reduced to approximately $10^{-4}$ Pa, and was subjected to vacuum baking at 170° C. for 30 minutes in a heating chamber of the vacuum evaporation apparatus, and then the substrate was cooled down for about 30 minutes.

Then, the substrate was fixed to a substrate holder provided in the vacuum evaporation apparatus such that the surface on which the transparent conductive film was formed faced downward. After that, on the transparent conductive film, 9-phenyl-3-[4-(10-phenyl-9-anthryl)phenyl]-9H-carbazole (abbreviation: PCzPA) represented by Structural Formula (xiv) and molybdenum(VI) oxide were deposited by co-evaporation using resistance heating, whereby a first hole-injection layer was formed. The thickness of the first hole-injection layer for Light-emitting Element 8 (blue) was 40 nm, and that for Light-emitting Element 9 (yellow) was 45 nm. The weight ratio of PCzPA to molybdenum oxide was adjusted to 1:0.5.

Next, on the first hole-injection layer, PCzPA was deposited to form a first hole-transport layer. The thickness of the first hole-transport layer was 20 nm.

On the first hole-transport layer, a first light-emitting layer was formed by deposition of 7-[4-(10-phenyl-9-anthryl)phenyl]-7H-dibenzo[c,g]carbazole (abbreviation: cgDBCzPA) represented by Structural Formula (ii) and N,N'-(pyrene-1,6-diyl)bis[(6,N-diphenylbenzo[b]naphtho[1,2-d]furan)-8-amine] (abbreviation: 1,6BnfAPrn-03) represented by Structural Formula (iii) to a thickness of 25 nm such that the weight ratio of cgDBCzPA to 1,6BnfAPrn-03 was 1:0.03.

Then, a first electron-transport layer was formed over the first light-emitting layer in such a way that cgDBCzPA was deposited to a thickness of 10 nm and bathophenanthroline (abbreviation: BPhen) represented by Structural Formula (vi) was deposited to a thickness of 10 nm.

After the first electron-transport layer was formed, lithium oxide ($Li_2O$) was evaporated to a thickness of 0.1 nm. Then, copper phthalocyanine (abbreviation: CuPc) represented by Structural Formula (xi) was evaporated to a thickness of 2 nm. After that, PCzPA and molybdenum oxide were co-evaporated such that the weight ratio of PCzPA to molybdenum oxide was 1:0.5. In such a manner, an intermediate layer was formed. The thickness of the intermediate layer was 12.5 nm.

Next, on the intermediate layer, PCzPA was evaporated to a thickness of 20 nm, whereby a second hole-transport layer was formed.

After the second hole-transport layer was formed, 2-[3'-(dibenzothiophen-4-yl)biphenyl-3-yl]dibenzo[f,h]quinoxaline (abbreviation: 2mDBTBPDBq-II) represented by Structural Formula (vii), N-(1,1'-biphenyl-4-yl)-9,9-dimethyl-N-[4-(9-phenyl-9H-carbazol-3-yl)phenyl]-9H-fluoren-2-amine (abbreviation: PCBBiF) represented by Structural Formula (viii), and bis{2-[5-methyl-6-(2-methylphenyl)-4-pyrimidinyl-κN3]phenyl-κC}(2,4-pentanedionato-$κ^2$O,O')iridium (III) (abbreviation: [Ir(mpmppm)$_2$(acac)]) represented by Structural Formula (ix) were co-evaporated such that the weight ratio of 2mDBTBPDBq-II to PCBBiF and [Ir(mpmppm)$_2$(acac)] was 0.8:0.2:0.06. In this manner, a second light-emitting layer was formed. The thickness of the second light-emitting layer was 40 nm.

On the second light-emitting layer, 2mDBTBPDBq-II was evaporated to a thickness of 15 nm. On 2mDBTBPDBq-II, BPhen was evaporated to a thickness of 20 nm. In this manner, a second electron-transport layer was formed.

After that, lithium fluoride was evaporated to a thickness of 1 nm to form an electron-injection layer. Then, silver and magnesium were co-evaporated to a thickness of 15 nm with a volume ratio of 1:0.1 (=silver:magnesium). Next, ITO was deposited to a thickness of 70 nm by a sputtering method. In this manner, a second electrode (semi-transmissive and semi-reflective electrode) was formed. Through the above steps, Light-emitting Element 8 (blue) and Light-emitting Element 9 (yellow) were fabricated. Note that in all the above evaporation steps, evaporation was performed by a resistance-heating method.

The element structures of Light-emitting Elements 8 and 9 are listed below.

TABLE 10

| Reflective Electrode | | Hole-injection Layer | First Hole-transport Layer | First Light-emitting Layer | First Electron-transport Layer | |
|---|---|---|---|---|---|---|
| APC | ITSO | PCzPA:MoOx 1:0.5 | PCzPA | cgDBCzPA:1,6BnfAPrn-03 1:0.03 | cgDBCzPA | BPhen |
| 100 nm | *19 | *20 | 20 nm | 25 nm | 10 nm | 10 nm |
| | | | | | | Continued on *22 |

| | | Intermediate Layer | | Second Hole-transport Layer | Second Light-emitting Layer | Second Electron-transport Layer | |
|---|---|---|---|---|---|---|---|
| $Li_2O$ | CuPC | PCzPA:MoOx 1:0.5 | | PCzPA | 2mDBTBPDBq-II:PCBBiF: [Ir(mpmppm)$_2$(acac)] 0.8:0.2:0.06 | 2mDBTBPDBq-II | BPhen |
| 0.1 nm *22 | 2 nm | 12.5 nm | | 20 nm | 40 nm | 15 nm | 20 nm Continued on *23 |

| Electron-injection Layer | Semi-transmissive and Semi-reflective Electrode | | Color Filter |
|---|---|---|---|
| LiF | Ag:Mg 1:0.1 | ITO | *21 |
| 1 nm *23 | 15 nm | 70 nm | |

*19 Light-emitting Element 8: 85 nm, Light-emitting Element 9: 65 nm
*20 Light-emitting Element 8: 40 nm, Light-emitting Element 9: 45 nm
*21 Light-emitting Element 8: Blue 0.8 μm, Light-emitting Element 9: Yellow 0.8 μm Each of Light-emitting Element 8(blue) and Light-emitting Element 9(yellow) was sealed using a glass substrate in a glove box containing a nitrogen atmosphere so as not to be exposed to the air (specifically, a sealing material was applied to surround the element, and at the time of sealing, UV treatment (with 365-nm ultraviolet light at 6 J/cm$^2$) was performed and heat treatment was performed at 80° C. for 1 hour). Then, initial characteristics of these light-emitting elements were measured. Note that the measurement was carried out at room temperature (in an atmosphere kept at 25° C.). As for Light-emitting Element 8, the measurement was carried out on light through a blue color filter. As for Light-emitting Element 9, the measurement was carried out on light through a yellow color filter.

Figure 39:
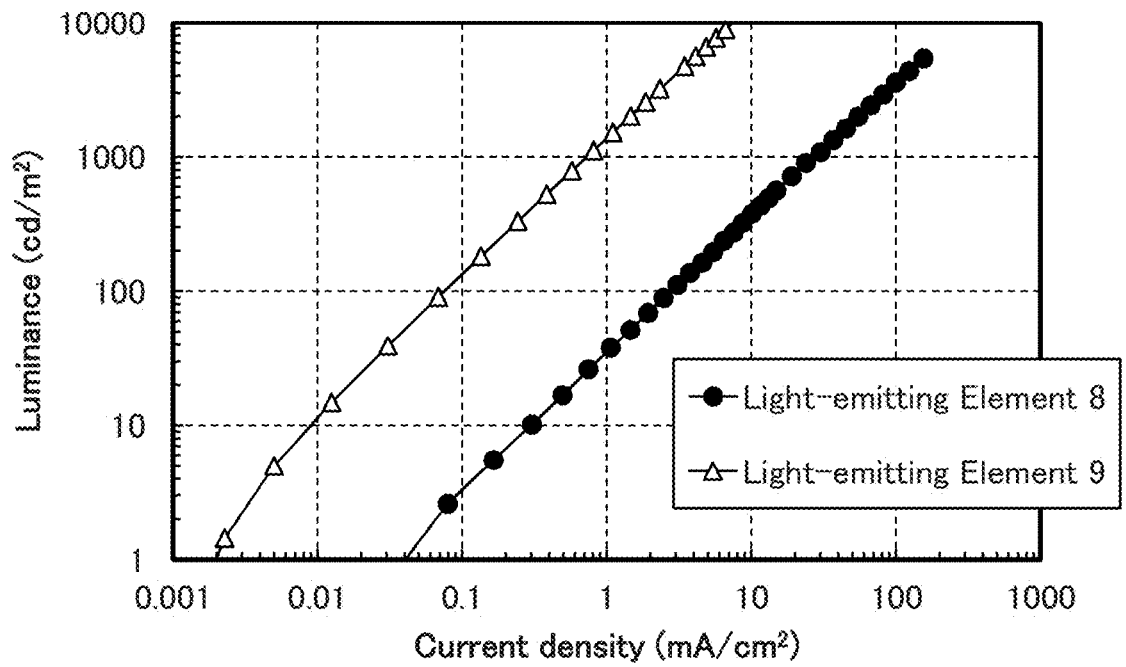
FIG. 39 shows luminance-current density characteristics of Light-emitting Elements 8 and 9.
Figure 40:
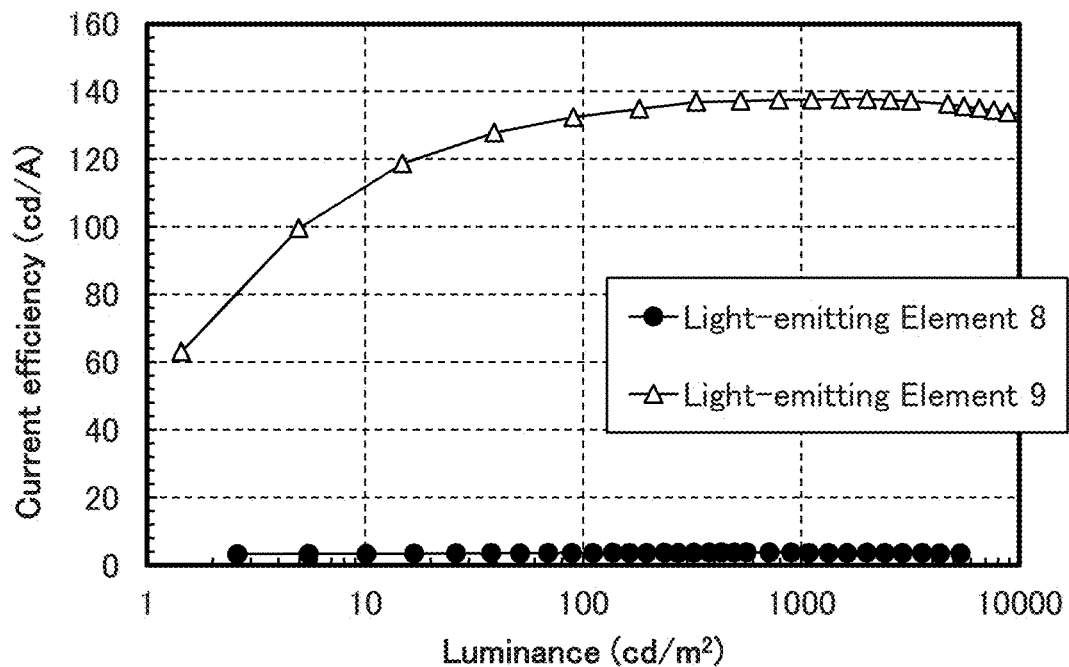
FIG. 40 shows current efficiency-luminance characteristics of Light-emitting Elements 8 and 9.
Figure 41:
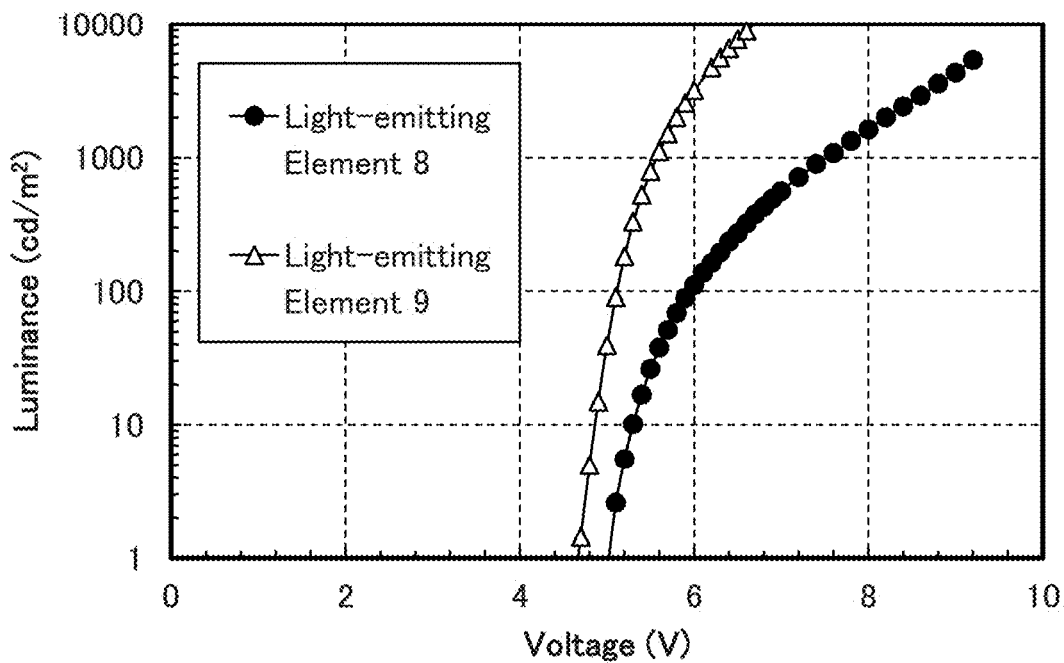
FIG. 41 shows luminance-voltage characteristics of Light-emitting Elements 8 and 9.
Figure 42:
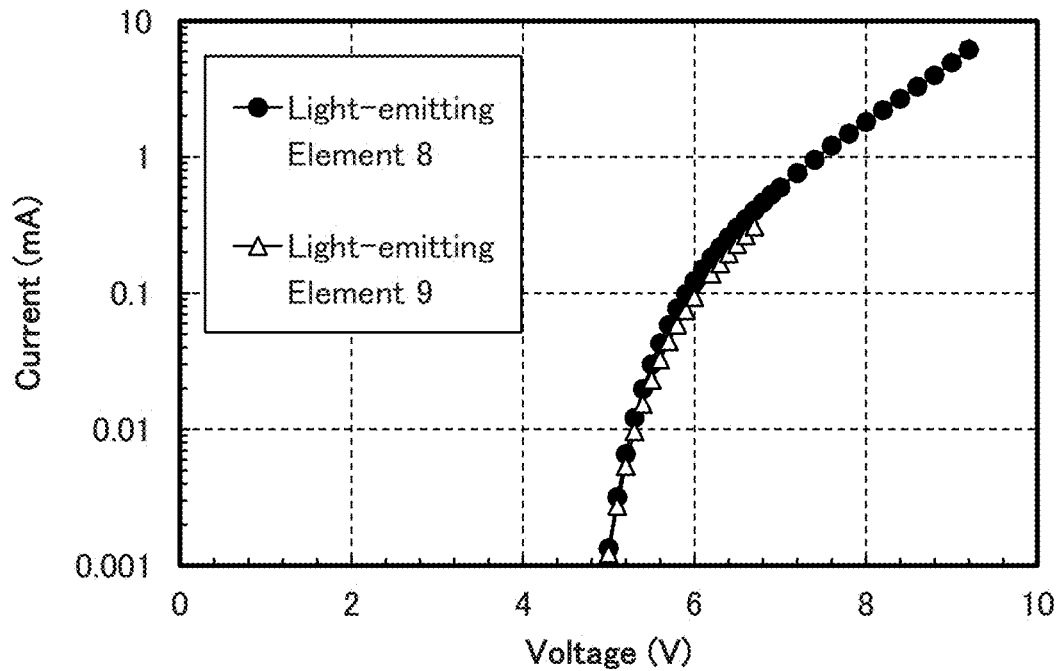
FIG. 42 shows current-voltage characteristics of Light-emitting Elements 8 and 9.
Figure 43:
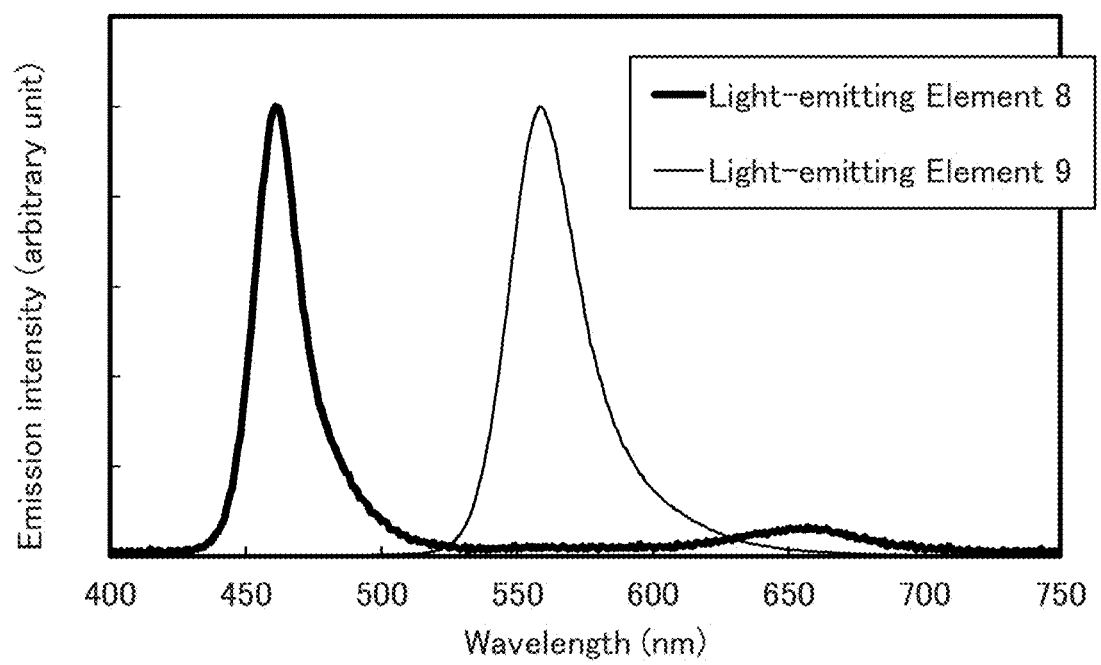
FIG. 43 shows emission spectra of Light-emitting Elements 8 and 9.

FIG. 39 shows luminance-current density characteristics of Light-emitting Element 8 (blue) and Light-emitting Element 9 (yellow), FIG. 40 shows current efficiency-luminance characteristics thereof, FIG. 41 shows luminance-voltage characteristics thereof, FIG. 42 shows current-voltage characteristics thereof, and FIG. 43 shows emission spectra thereof. As shown in these graphs, Light-emitting Element 8 and Light-emitting Element 9 have favorable characteristics.

Figure 44:
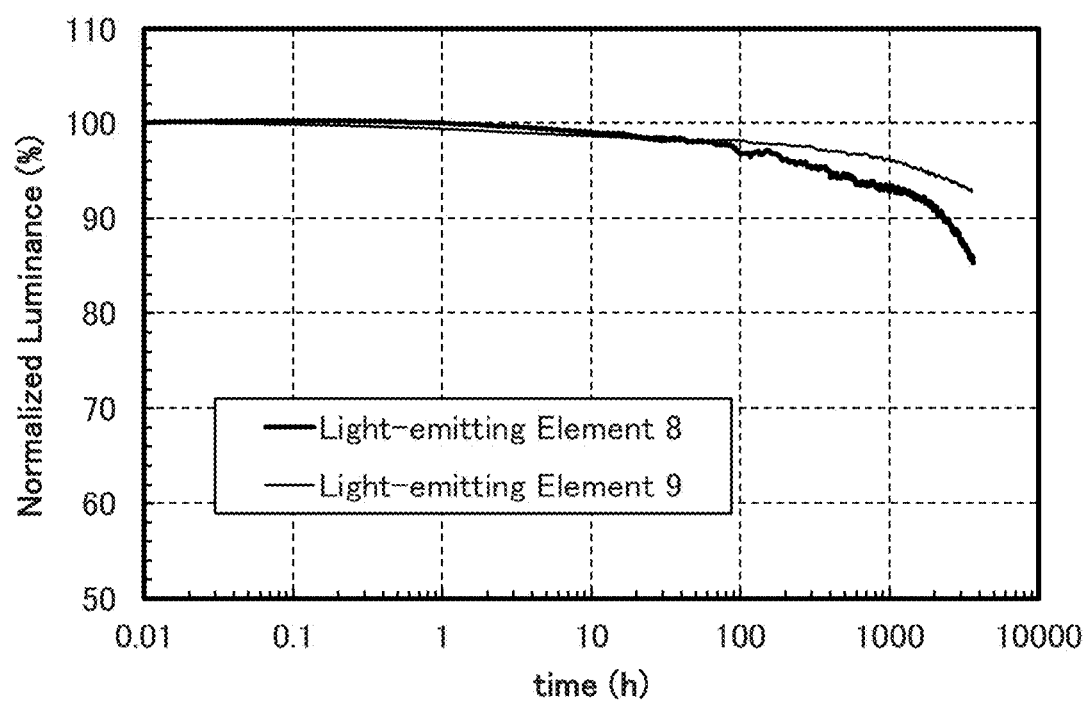
FIG. 44 shows normalized luminance-time dependence characteristics of Light-emitting Elements 8 and 9.

Next, driving tests on Light-emitting Element 8 (blue) and Light-emitting Element 9 (yellow) were carried out under the conditions where the initial luminance of Light-emitting Element 8 was 300 cd/m$^2$, the initial luminance of Light-emitting Element 9 was 3000 cd/m$^2$, and the current density was constant. FIG. 44 shows a change in luminance over driving time with an initial luminance taken as 100%.

As shown in FIG. 44, it took approximately 2300 hours for the luminance of Light-emitting Element 8 to decrease to 90% of the initial luminance, and it took approximately 6000 hours for the luminance of Light-emitting Element 9 to decrease to 90% of the initial luminance. These results indicate that the light-emitting device of one embodiment of the present invention consumes significantly low power, has a little luminance degradation, and has reliability high enough for practical use.

Example 4

Figure 37:
FIG. 37 shows a light-emitting device of an example.
Figure 38:
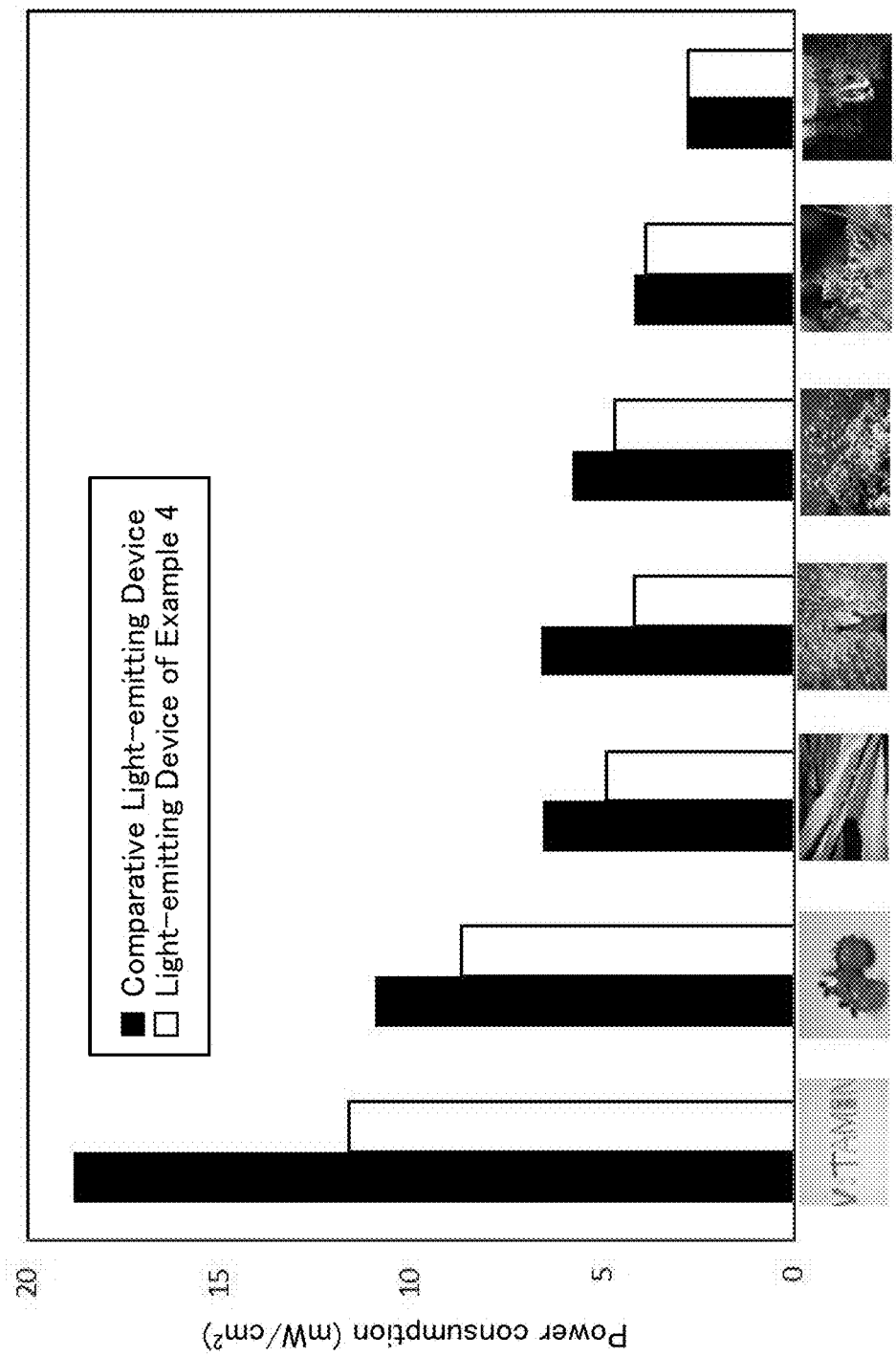
FIG. 38 shows a comparison of power consumption.

In this example, a 254-ppi light-emitting device using a color filter method was fabricated actually. FIG. 37 is a photograph of the fabricated light-emitting device. In each pixel, red, yellow, green, and blue subpixels each having a size of 50 μm square are arranged in a 2×2 matrix. FIG. 38 shows a comparison between the power consumption at the time of displaying a still image in the light-emitting device of this example and that in the light-emitting device of a comparative example using a white-color filter method in which red, green, and blue subpixels are used. The power consumption of panel portions displaying still images was calculated at a peak luminance of 300 cd/m$^2$.

It is obvious from FIG. 38 that the power consumption of the light-emitting device of this example is lower than that of the light-emitting device of the comparative example. In particular, a reduction in power consumption of the present invention is considerable at the time of displaying an image in which a white display region occupies a large area. The power consumption at the time of displaying the image in which the white display region occupies a large area is the highest; the higher the proportion of a black display region is, the lower the power consumption per unit area becomes in each panel. This is because an OLED emits no light at the time of displaying black, whereas a backlight needs to be kept on in a liquid crystal display.

Reference Example

In this reference example, a method for synthesizing N,N'-(pyrene-1,6-diyl)bis[(6,N-diphenylbenzo[b]naphtho[1,2-d]furan)-8-amine] (abbreviation: 1,6BnfAPrn-03), an organic compound used in this example, is described. Note that a structure of 1,6BnfAPrn-03 is shown below.

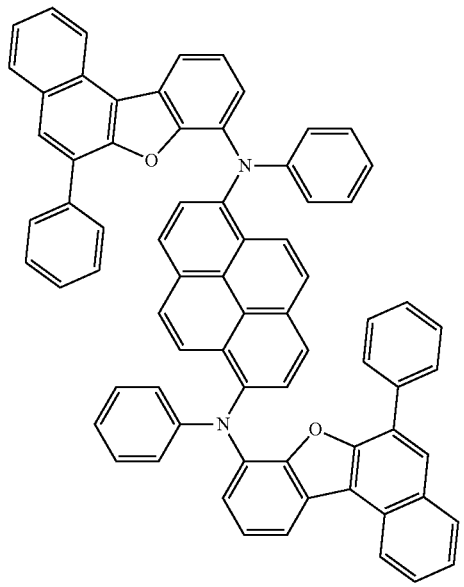

1,6BnfAPrn-03

Step 1: Synthesis of 6-iodobenzo[b]naphtho[1,2-d]furan

Into a 500 mL three-neck flask were put 8.5 g (39 mmol) of benzo[b]naphtho[1,2-d]furan, and the air in the flask was replaced with nitrogen. Then, 195 mL of tetrahydrofuran was added thereto. This solution was cooled to −75° C. Then, 25 mL (40 mmol) of n-butyllithium (a 1.59 mol/L n-hexane solution) was dropped into this solution. After the drop, the resulting solution was stirred at room temperature for 1 hour.

After a predetermined period of time, the resulting solution was cooled to −75° C. Then, a solution in which 10 g (40 mmol) of iodine had been dissolved in 40 mL of THF was dropped into this solution. After the drop, the resulting solution was stirred for 17 hours while the temperature of the solution was returned to room temperature. After a predetermined period of time, an aqueous solution of sodium thiosulfate was added to the mixture, and the resulting mixture was stirred for 1 hour. Then, an organic layer of the mixture was washed with water and dried with magnesium sulfate. After the drying, the mixture was gravity-filtered to give a solution. The resulting solution was suction-filtered through Celite (Catalog No. 531-16855 produced by Wako Pure Chemical Industries, Ltd.) and Florisil (Catalog No. 540-00135 produced by Wako Pure Chemical Industries, Ltd.) to give a filtrate. The resulting filtrate was concentrated to give a solid. The resulting solid was recrystallized from toluene to give 6.0 g (18 mmol) of white powder of the target substance in 45% yield. A synthesis scheme of Step 1 is shown below.

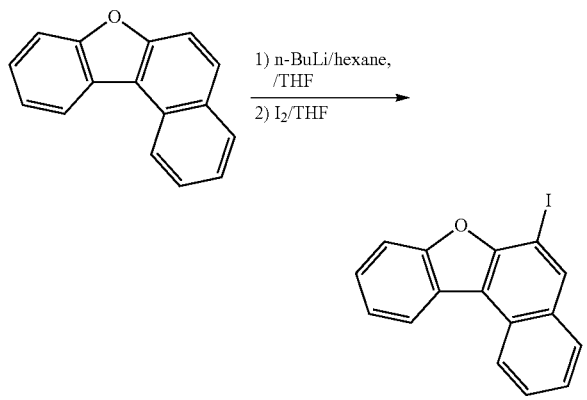

Step 2: Synthesis of 6-phenylbenzo[b]naphtho[1,2-d]furan

Into a 200 mL three-neck flask were put 6.0 g (18 mmol) of 6-iodobenzo[b]naphtho[1,2-d]furan, 2.4 g (19 mmol) of phenylboronic acid, 70 mL of toluene, 20 mL of ethanol, and 22 mL of an aqueous solution of potassium carbonate (2.0 mol/L). This mixture was degassed by being stirred while the pressure was reduced. After the degassing, the air in the flask was replaced with nitrogen, and then 480 mg (0.42 mmol) of tetrakis(triphenylphosphine)palladium(0) was added to the mixture. The resulting mixture was stirred at 90° C. under a nitrogen stream for 12 hours.

After a predetermined period of time, water was added to the mixture, and an aqueous layer was subjected to extraction with toluene. The extracted solution and the organic layer were combined, and the mixture was washed with water and then dried with magnesium sulfate. The mixture was gravity-filtered to give a filtrate. The resulting filtrate was concentrated to give a solid, and the resulting solid was dissolved in toluene. The resulting solution was suction-filtered through Celite (Catalog No. 531-16855 produced by Wako Pure Chemical Industries, Ltd.), Florisil (Catalog No. 540-00135 produced by Wako Pure Chemical Industries, Ltd.), and alumina to give a filtrate. The resulting filtrate was concentrated to give a solid. The resulting solid was recrystallized from toluene to give a 4.9 g (17 mmol) of a white solid of the target substance in 93% yield. A synthesis scheme of Step 2 is shown below.

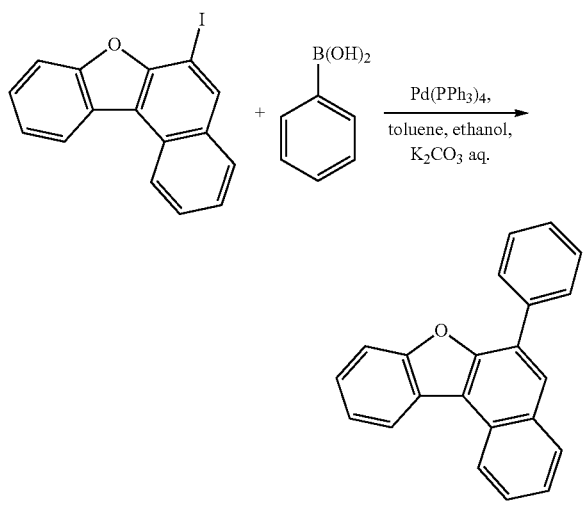

Step 3: Synthesis of 8-iodo-6-phenylbenzo[b]naphtho[1,2,d]furan

Into a 300 mL three-neck flask was put 4.9 g (17 mmol) of 6-phenylbenzo[b]naphtho[1,2-d]furan, and the air in the flask was replaced with nitrogen. Then, 87 mL of tetrahydrofuran (THF) was added thereto. The resulting solution was cooled to −75° C. Then, 11 mL (18 mmol) of n-butyllithium (a 1.59 mol/L n-hexane solution) was dropped into the solution. After the drop, the resulting solution was stirred at room temperature for 1 hour. After a predetermined period of time, the resulting solution was cooled to −75° C. Then, a solution in which 4.6 g (18 mmol) of iodine had been dissolved in 18 mL of THF was dropped into the resulting solution.

The resulting solution was stirred for 17 hours while the temperature of the solution was returned to room temperature. After a predetermined period of time, an aqueous solution of sodium thiosulfate was added to the mixture, and the resulting mixture was stirred for 1 hour. Then, an organic layer of the mixture was washed with water and dried with magnesium sulfate. The mixture was gravity-filtered to give a filtrate. The resulting filtrate was suction-filtered through Celite (Catalog No. 531-16855 produced by Wako Pure Chemical Industries, Ltd.), Florisil (Catalog No. 540-00135 produced by Wako Pure Chemical Industries, Ltd.), and alumina to give a filtrate. The resulting filtrate was concentrated to give a solid. The resulting solid was recrystallized from toluene to give 3.7 g (8.8 mmol) of a target white solid in 53% yield. A synthesis scheme of Step 3 is shown below.

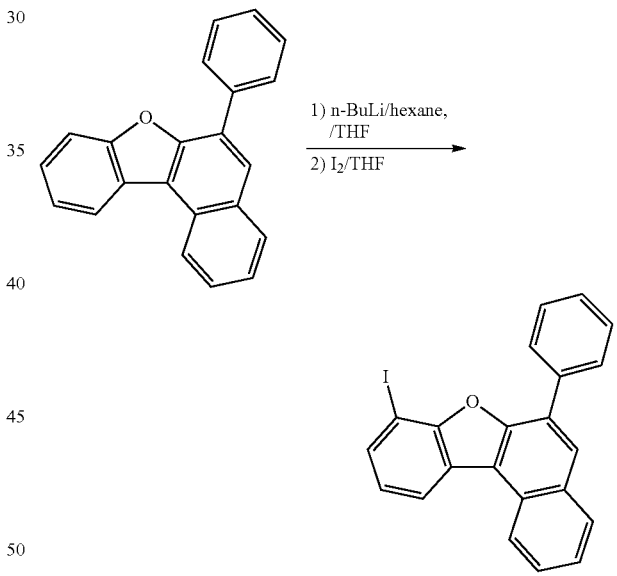

Step 4: Synthesis of 1,6BnfAPrn-03

Into a 100 mL three-neck flask were put 0.71 g (2.0 mmol) of 1,6-dibromopyrene, 1.0 g (10.4 mmol) of sodium-tert-butoxide, 10 mL of toluene, 0.36 mL (4.0 mmol) of aniline, and 0.3 mL of tri(tert-butyl)phosphine (a 10 wt % hexane solution), and the air in the flask was replaced with nitrogen. To this mixture was added 50 mg (85 μmol) of bis(dibenzylideneacetone)palladium(0), and the resulting mixture was stirred at 80° C. for 2 hours.

After a predetermined period of time, to the resulting mixture were added 1.7 g (4.0 mmol) of 8-iodo-6-phenylbenzo[b]naphtho[1,2,d]furan, 180 mg (0.44 mmol) of 2-dicyclohexylphosphino-2',6'-dimethoxybiphenyl (abbreviation: S-Phos), and 50 mg (85 μmol) of bis(dibenzylideneacetone)palladium(0), and the resulting mixture was stirred at 100° C. for 15 hours. After a predetermined period of time, the resulting mixture was filtered through Celite (Catalog No. 531-16855 produced by Wako Pure Chemical Industries, Ltd.) to give a filtrate. The resulting filtrate was concentrated to give a solid. The resulting solid was washed with ethanol and recrystallized from toluene to give 1.38 g (1.4 mmol) of a yellow solid of the target substance in 71% yield.

By a train sublimation method, 1.37 mg (1.4 mmol) of the resulting yellow solid was purified by sublimation. The purification by sublimation was conducted by heating the yellow solid at 370° C. at an argon flow rate of 10 mL/min under a pressure of under a pressure of 2.3 Pa. As a result of the purification by sublimation, 0.68 g (0.70 mmol) of the yellow solid was recovered at a collection rate of 50%. A synthesis scheme of Step 4 is shown below.

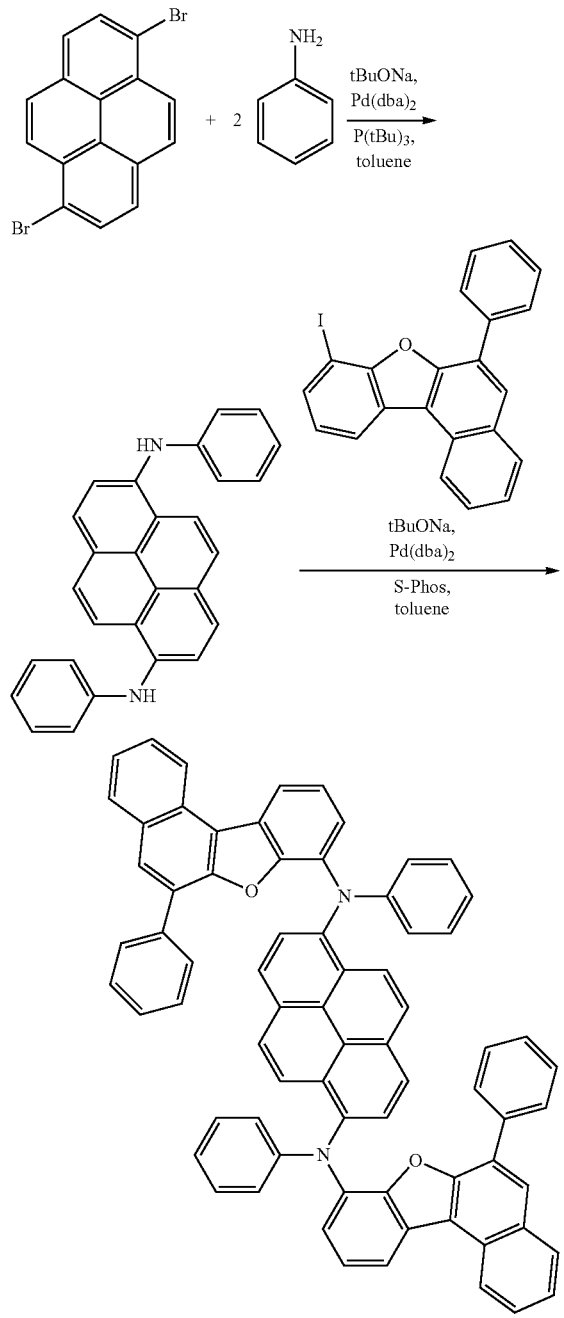

Analysis results by nuclear magnetic resonance ($^1$H-NMR) spectroscopy of the yellow solid obtained in Step 4 are described below. The results revealed that 1,6BnfAPrn-03 was obtained.

$^1$H NMR (dichloromethane-d2, 500 MHz): δ=6.88 (t, J=7.7 Hz, 4H), 7.03-7.06 (m, 6H), 7.11 (t, J=7.5 Hz, 2H), 7.13 (d, J=8.0 Hz, 2H), 7.28-7.32 (m, 8H), 7.37 (t, J=8.0 Hz, 2H), 7.59 (t, J=7.2 Hz, 2H), 7.75 (t, J=7.7 Hz, 2H), 7.84 (d, J=9.0 Hz, 2H), 7.88 (d, J=8.0 Hz, 2H), 8.01 (s, 2H), 8.07 (d, J=8.0 Hz, 4H), 8.14 (d, J=9.0 Hz, 2H), 8.21 (d, J=8.0 Hz, 2H), 8.69 (d, J=8.5 Hz, 2H).

REFERENCE NUMERALS

101: first electrode, 102: second electrode, 103a: EL layer, 103b: EL layer, 104a: hole-injection layer, 104b: hole-injection layer, 105a: hole-transport layer, 105b: hole-transport layer, 106: light-emitting layer, 106a: light-emitting layer, 106b: light-emitting layer, 107a: electron-transport layer, 107b: electron-transport layer, 108a: electron-injection layer, 108b: electron-injection layer, 109: charge-generation layer, 113: first light-emitting layer, 114: second light-emitting layer, 121: guest material (fluorescent material), 122: host material, 131: guest material (phosphorescent material), 132: first organic compound, 133: second organic compound, 134: exciplex, 501: substrate, 502: FET, 503: first electrode, 504: partition, 505: EL layer, 506R: light-emitting region, 506G: light-emitting region, 506B: light-emitting region, 506W: light-emitting region, 506Y: light-emitting region, 507R: light-emitting element, 507G: light-emitting element, 507B: light-emitting element, 507W: light-emitting element, 507Y: light-emitting element, 508R: coloring layer, 508G: coloring layer, 508B: coloring layer, 508Y: coloring layer, 509: black layer (black matrix), 510: second electrode, 511: sealing substrate, 601: element substrate, 602: pixel portion, 603: driver circuit portion (source line driver circuit), 604a: driver circuit portion (gate line driver circuit), 604b: driver circuit portion (gate line driver circuit), 605: sealant, 606: sealing substrate, 607: wiring, 608: FPC (flexible printed circuit), 609: FET, 610: FET, 611: switching FET, 612: current control FET, 613: first electrode (anode), 614: insulator, 615: EL layer, 616: second electrode (cathode), 617: light-emitting element, 618: space, 1100: substrate, 1102B: first electrode, 1102G: first electrode, 1102Y: first electrode, 1102R: first electrode, 1103d: blue light-emitting layer, 1103e: hole-injection layer and hole-transport layer, 1103f: yellow light-emitting layer, 1103h: electron-transport layer and electron-injection layer, 1104: second electrode, 1105: black matrix, 1106B: color filter, 1106G: color filter, 1106Y: color filter, 1106R: color filter, 1101: sealing substrate, 2000: touch panel, 2001: touch panel, 2501: display portion, 2502R: pixel, 2502t: transistor, 2503c: capacitor, 2503g: scan line driver circuit, 2503t: transistor, 2509: FPC, 2510: substrate, 2511: wiring, 2519: terminal, 2521: insulating layer, 2528: partition, 2550R: light-emitting element, 2560: sealing layer, 2567BM: light-blocking layer, 2567p: anti-reflective layer, 2567R: coloring layer, 2570: substrate, 2580R: light-emitting module, 2590: substrate, 2591: electrode, 2592: electrode, 2593: insulating layer, 2594: wiring, 2595: touch sensor, 2597: adhesive layer, 2598: wiring, 2599: connection layer, 2601: pulse voltage output circuit, 2602: current sensing circuit, 2603: capacitor, 2611: transistor, 2612: transistor, 2613: transistor, 2621: electrode, 2622: electrode, 7100: television device, 7101: housing, 7103: display portion, 7105: stand, 7107: display portion, 7109: operation key, 7110: remote controller, 7201: main body, 7202: housing, 7203: display portion, 7204: keyboard, 7205: external connection port, 7206: pointing device, 7302: housing, 7304: display panel, 7305: icon indicating time, 7306: another icon, 7311: operation button, 7312: operation button, 7313: connection terminal, 7321: band, 7322: clasp, 7400: mobile phone, 7401: housing, 7402: display portion, 7403: operation button, 7404: external connection portion, 7405: speaker, 7406: microphone, 7407: camera, 7500(1): housing, 7500(2): housing, 7501(1): display portion, 7501(2): display portion, 7502(1): display portion, 7502(2): display portion, 8001: lighting device, 8002: lighting device, 8003: lighting device, 8004: lighting device, 9310: portable information terminal, 9311: display panel, 9312: display region, 9313: hinge, and 9315: housing This application is based on Japanese Patent Application serial no. 2014-162532 filed with Japan Patent Office on Aug. 8, 2014, Japanese Patent Application serial no. 2014-162576 filed with Japan Patent Office on Aug. 8, 2014, Japanese Patent Application serial no. 2014-241188 filed with Japan Patent Office on Nov. 28, 2014, and Japanese Patent Application serial no. 2015-131156 filed with Japan Patent Office on Jun. 30, 2015, the entire contents of which are hereby incorporated by reference.

The invention claimed is:

1. A light-emitting device with a bottom emission structure, comprising:
   a substrate;
   a transistor comprising:
      a first insulating layer over the substrate;
      an oxide semiconductor layer over the first insulating layer;
      a source electrode, a drain electrode, and a gate electrode over the oxide semiconductor layer; and
      a second insulating layer over the oxide semiconductor layer, the source electrode, and the drain electrode;
   an anode over the transistor;
   a first light-emitting element configured to emit light through a first coloring layer so that blue light is extracted to an outside of the light-emitting device;
   a second light-emitting element configured to emit light through a second coloring layer so that green light is extracted to the outside of the light-emitting device;
   a third light-emitting element configured to emit light through a third coloring layer so that green light is extracted to the outside of the light-emitting device; and
   a fourth light-emitting element,
   wherein:
   one of the source electrode and the drain electrode is electrically connected to the anode,
   the anode is configured to function as a first electrode of one of the first to fourth light-emitting elements,
   the first to fourth light-emitting elements comprise the same structure of a first EL layer and a second EL layer with a charge-generation layer therebetween,
   the first EL layer includes a fluorescent substance configured to emit blue light, and
   the second EL layer includes a phosphorescent substance configured to emit yellow light.

2. A light-emitting device with a bottom emission structure, comprising:
   a substrate;
   a transistor comprising:
      a first insulating layer over the substrate;
      an oxide semiconductor layer over the first insulating layer;
      a source electrode, a drain electrode, and a gate electrode over the oxide semiconductor layer; and
      a second insulating layer over the oxide semiconductor layer, the source electrode, and the drain electrode;
   an anode over the transistor;
   a first light-emitting element configured to emit light through a first coloring layer so that blue light is extracted to an outside of the light-emitting device;
   a second light-emitting element configured to emit light through a second coloring layer so that green light is extracted to the outside of the light-emitting device;
   a third light-emitting element configured to emit light through a third coloring layer so that red light is extracted to the outside of the light-emitting device; and
   a fourth light-emitting element,
   wherein:
   one of the source electrode and the drain electrode is electrically connected to the anode,
   the anode is configured to function as a first electrode of one of the first to fourth light-emitting elements,
   the first light-emitting element comprises a first EL layer and a second EL layer with a charge-generation layer therebetween,
   the second to fourth light-emitting elements comprise the first EL layer and the second EL layer with the charge-generation layer therebetween,
   the first EL layer includes a first light-emitting layer configured to emit blue light, and
   the second EL layer includes a second light-emitting layer configured to emit yellow light.

3. A light-emitting device with a bottom emission structure, comprising:
   a plurality of pixels, one of the plurality of pixels comprising:
   a transistor over a substrate, the transistor comprising:
      an oxide semiconductor layer over a first insulating layer;
      a gate electrode over the oxide semiconductor layer;
      a source electrode and a drain electrode electrically connected to the oxide semiconductor layer; and
      a second insulating layer over the oxide semiconductor layer, the source electrode, and the drain electrode;
   an anode over the transistor;
   a first EL layer configured to emit one of blue light and yellow light;
   a second EL layer configured to emit the other one of blue light and yellow light; and
   a charge-generation layer between the first EL layer and the second EL layer,
   wherein:
   a first light-emitting element comprising the first EL layer, the charge-generation layer, and the second EL layer is configured to emit light through a first coloring layer so that blue light is extracted to an outside of the light-emitting device,
   a second light-emitting element comprising the first EL layer, the charge-generation layer, and the second EL layer is configured to emit light through a second coloring layer so that green light is extracted to an outside of the light-emitting device,
   a third light-emitting element comprising the first EL layer, the charge-generation layer, and the second EL layer is configured to emit light through a third coloring layer so that red light is extracted to an outside of the light-emitting device, a fourth light-emitting element comprising the first EL layer, the charge-generation layer, and the second EL layer is configured to emit light to the outside of the light-emitting device, the light emitted to the outside of the light-emitting device by the fourth light-emitting element is obtained by combining the one of blue light and yellow light emitted from the first EL layer and the other one of blue light and yellow light emitted from the second EL layer, one of the source electrode and the drain electrode is electrically connected to the anode, and the anode is configured to function as a first electrode of one of the first to fourth light-emitting elements.

4. The light-emitting device according to claim 1,
wherein a peak wavelength of the blue light extracted to the outside of a light-emitting device is 400 nm to 480 nm inclusive,
wherein a peak wavelength of the green light extracted to the outside of a light-emitting device is 500 nm to 560 nm inclusive,
wherein a peak wavelength of the red light extracted to the outside of a light-emitting device is 580 nm to 680 nm, and
wherein the one of the first to fourth light-emitting elements overlaps with the transistor.

5. The light-emitting device according to claim 2,
wherein a peak wavelength of the blue light extracted to the outside of a light-emitting device is 400 nm to 480 nm inclusive,
wherein a peak wavelength of the green light extracted to the outside of a light-emitting device is 500 nm to 560 nm inclusive,
wherein a peak wavelength of the red light extracted to the outside of a light-emitting device is 580 nm to 680 nm, and
wherein the one of the first to fourth light-emitting elements overlaps with the transistor.

6. The light-emitting device according to claim 3,
wherein a peak wavelength of the blue light extracted to the outside of a light-emitting device is 400 nm to 480 nm inclusive,
wherein a peak wavelength of the green light extracted to the outside of a light-emitting device is 500 nm to 560 nm inclusive,
wherein a peak wavelength of the red light extracted to the outside of a light-emitting device is 580 nm to 680 nm, and
wherein the one of the first to fourth light-emitting elements overlaps with the transistor.

7. The light-emitting device according to claim 1, wherein:
the fourth light-emitting element is configured to emit yellow light, and
a peak wavelength of the yellow light emitted from the fourth light-emitting element is 555 nm to 590 nm inclusive.

8. The light-emitting device according to claim 2, wherein:
the fourth light-emitting element is configured to emit yellow light, and
a peak wavelength of the yellow light emitted from the fourth light-emitting element is 555 nm to 590 nm inclusive.

9. The light-emitting device according to claim 1, wherein the fluorescent substance has a pyrene skeleton with two benzo[b]naphtho[1,2-d]furanylamine skeletons.

10. The light-emitting device according to claim 2,
wherein the first EL layer includes a fluorescent substance, and
wherein the fluorescent substance has a pyrene skeleton with two benzo[b]naphtho[1,2-d]furanylamine skeletons.

11. The light-emitting device according to claim 3,
wherein the first EL layer includes a fluorescent substance, and
wherein the fluorescent substance has a pyrene skeleton with two benzo[b]naphtho[1,2-d]furanylamine skeletons.

12. The light-emitting device according to claim 9, wherein, in the pyrene skeleton, the two benzo[b]naphtho[1,2-d]furanylamine skeletons are bonded to the 1- and 6-positions.

13. The light-emitting device according to claim 10, wherein, in the pyrene skeleton, the two benzo[b]naphtho[1,2-d]furanylamine skeletons are bonded to the 1- and 6-positions.

14. The light-emitting device according to claim 11, wherein, in the pyrene skeleton, the two benzo[b]naphtho[1,2-d]furanylamine skeletons are bonded to the 1- and 6-positions.

15. The light-emitting device according to claim 1, wherein the fluorescent substance has an aromatic diamine skeleton or a pyrenediamine skeleton.

16. The light-emitting device according to claim 2,
wherein the first EL layer includes a fluorescent substance, and
wherein the fluorescent substance has an aromatic diamine skeleton or a pyrenediamine skeleton.

17. The light-emitting device according to claim 3,
wherein the first EL layer includes a fluorescent substance,
wherein the fluorescent substance has an aromatic diamine skeleton or a pyrenediamine skeleton,
wherein the first to fourth light-emitting elements share a cathode, and
wherein each of the first to fourth light-emitting elements further comprises a hole-injection layer, a hole-transport layer, an electron-transport layer, and an electron-injection layer.

18. The light-emitting device according to claim 1,
wherein one of the first EL layer and the second EL layer comprises a first organic compound and a second organic compound,
wherein the first organic compound and the second organic compound form an exciplex,
wherein the first to fourth light-emitting elements share a cathode, and
wherein each of the first to fourth light-emitting elements further comprises a hole-injection layer, a hole-transport layer, an electron-transport layer, and an electron-injection layer.

19. The light-emitting device according to claim 2,
wherein one of the first EL layer and the second EL layer comprises a first organic compound and a second organic compound,
wherein the first organic compound and the second organic compound form an exciplex,
wherein the first to fourth light-emitting elements share a cathode, and
wherein each of the first to fourth light-emitting elements further comprises a hole-injection layer, a hole-transport layer, an electron-transport layer, and an electron-injection layer.

* * * * *